(12) United States Patent
Williams et al.

(10) Patent No.: US 11,419,596 B2
(45) Date of Patent: Aug. 23, 2022

(54) GUARD DEVICE FOR A TISSUE CONTAINMENT SYSTEM

(71) Applicant: Atropolos Limited, Bray (IE)

(72) Inventors: Stephen Williams, Blackrock (IE); Lucy Dolores Halpin, Rathfarnham (IE); Frank Bonadio, Bray (IE); Shane J. Macnally, Delgany (IE); Robert Michael Boland, Enniskerry (IE)

(73) Assignee: Atropos Limited, Bray (IE)

( * ) Notice: Subject to any disclaimer, the term of this patent is extended or adjusted under 35 U.S.C. 154(b) by 0 days.

(21) Appl. No.: 17/049,284

(22) PCT Filed: Mar. 22, 2019

(86) PCT No.: PCT/EP2019/057290
§ 371 (c)(1),
(2) Date: Oct. 20, 2020

(87) PCT Pub. No.: WO2019/206537
PCT Pub. Date: Oct. 31, 2019

(65) Prior Publication Data
US 2021/0236110 A1    Aug. 5, 2021

(30) Foreign Application Priority Data

Apr. 23, 2018 (EP) .................... 18168839
Jun. 14, 2018 (EP) .................... 18177716
(Continued)

(51) Int. Cl.
*A61B 17/02* (2006.01)
*A61B 1/32* (2006.01)
(Continued)

(52) U.S. Cl.
CPC ............ *A61B 17/0293* (2013.01); *A61B 1/32* (2013.01); *A61B 2017/00287* (2013.01); *A61B 2090/08021* (2016.02)

(58) Field of Classification Search
CPC ................ A61B 17/02; A61B 17/0218; A61B 2017/0225; A61B 17/3421; A61B 17/3423; A61B 17/3431; A61B 2017/3429
See application file for complete search history.

(56) References Cited

U.S. PATENT DOCUMENTS

2011/0054260 A1*  3/2011  Albrecht ............ A61B 17/0218
                                                600/208
2012/0130183 A1*  5/2012  Barnes ............... A61B 17/3423
                                                600/206
(Continued)

FOREIGN PATENT DOCUMENTS

WO    WO 2014/116889 A1    7/2014
WO    WO 2014/207077 A1   12/2014

*Primary Examiner* — Eduardo C Robert
*Assistant Examiner* — Michelle C Eckman
(74) *Attorney, Agent, or Firm* — Bookoff McAndrews, PLLC

(57) ABSTRACT

Apparatus for placement in an incision or a natural body opening comprises a retractor having a sleeve (655, 656, 657) and a guard device comprising overlapping petals (662) depending from a mounting ring (661). The guard device is movable by the retractor from an insertion configuration to a deployed configuration as the retractor sleeve is moved to the retracting configuration.

18 Claims, 64 Drawing Sheets

(30) Foreign Application Priority Data

Sep. 25, 2018 (EP) .................................... 18196560
Oct. 12, 2018 (EP) .................................... 18200252
Feb. 13, 2019 (EP) .................................... 19156867

(51) Int. Cl.
*A61B 90/00* (2016.01)
*A61B 17/00* (2006.01)

(56) References Cited

U.S. PATENT DOCUMENTS

| | | |
|---|---|---|
| 2016/0262794 A1 | 9/2016 | Wachli et al. |
| 2017/0056065 A1* | 3/2017 | Do .................... A61B 17/0293 |
| 2017/0224321 A1* | 8/2017 | Kessler ............. A61B 17/3417 |
| 2017/0325800 A1 | 11/2017 | Prior |
| 2017/0340866 A1 | 11/2017 | Richard |

* cited by examiner

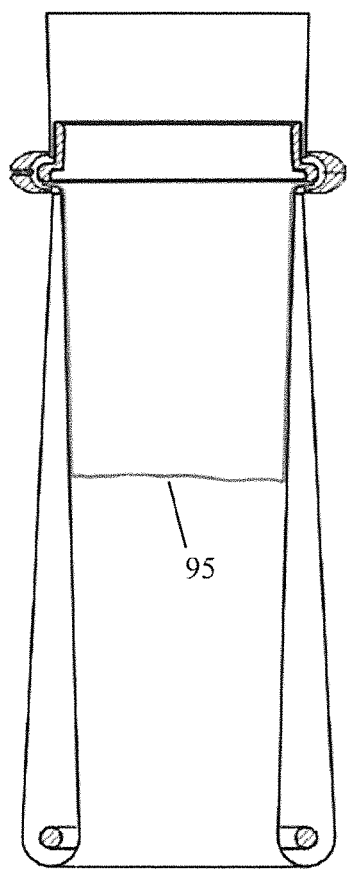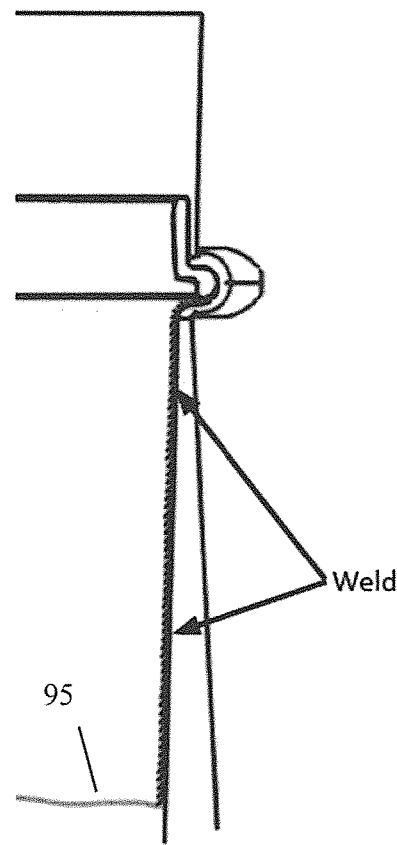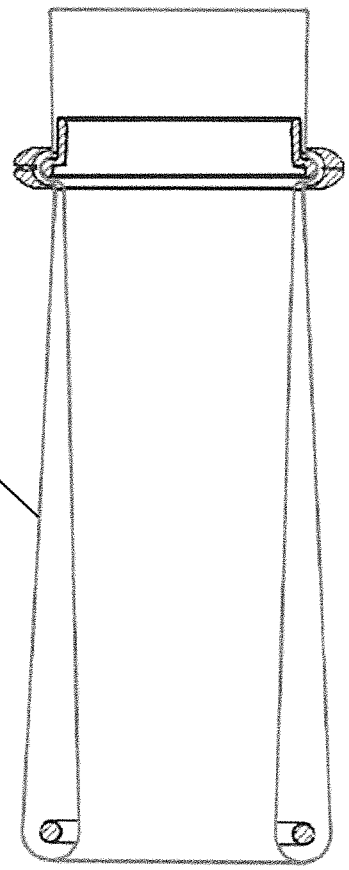
Fig. 50    Fig. 51
Fig. 52

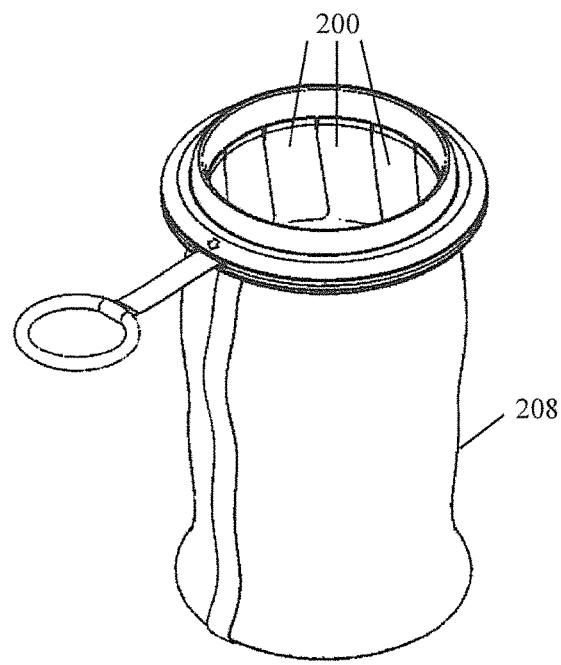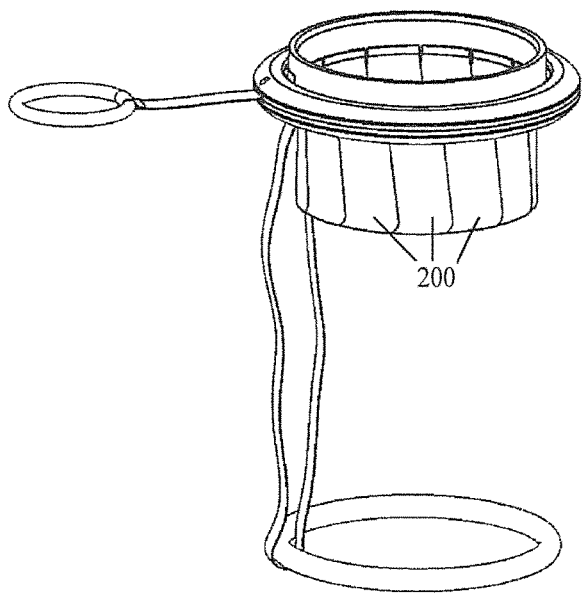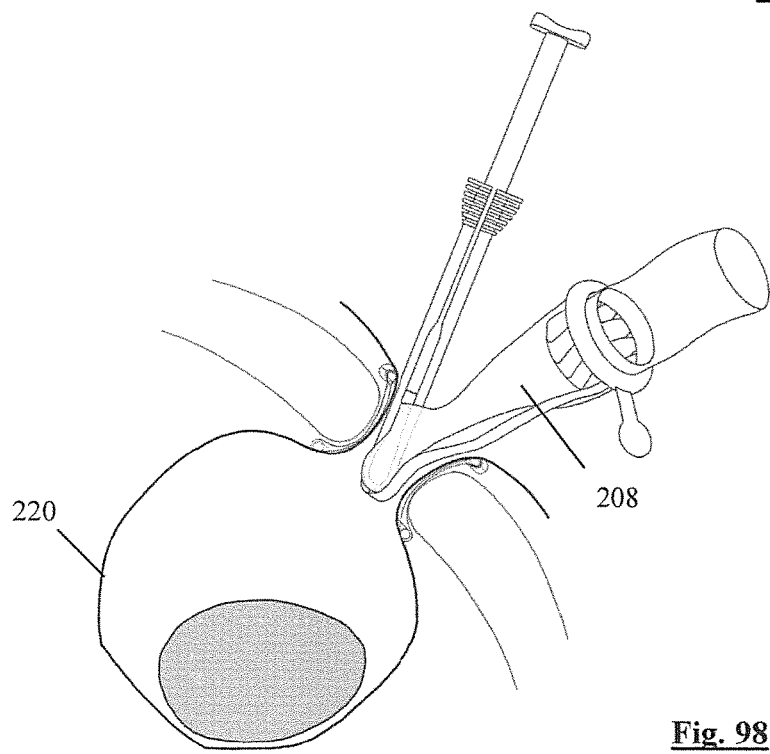
Fig. 96
Fig. 97
Fig. 98

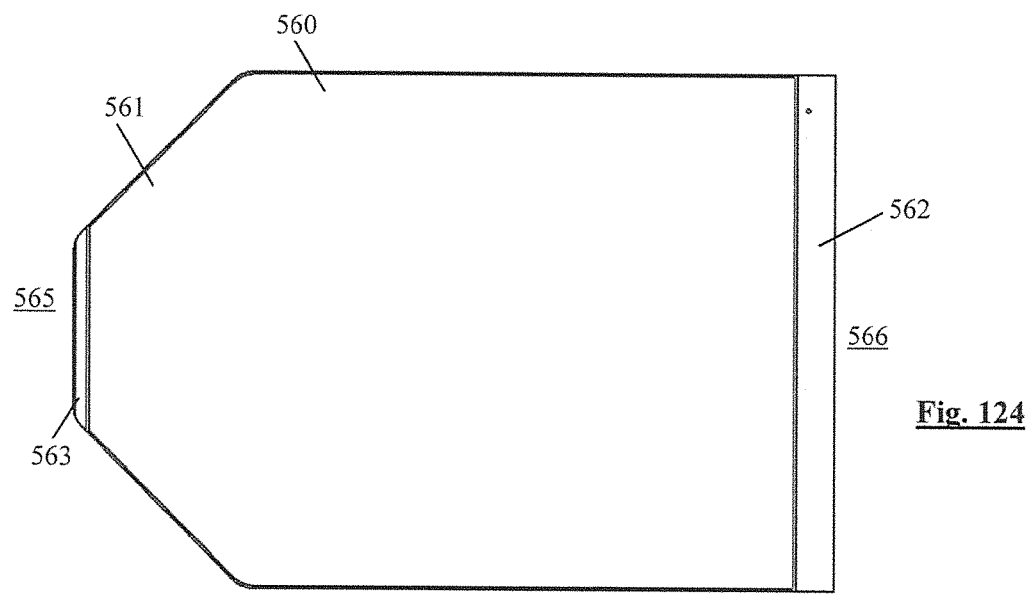
Fig. 124
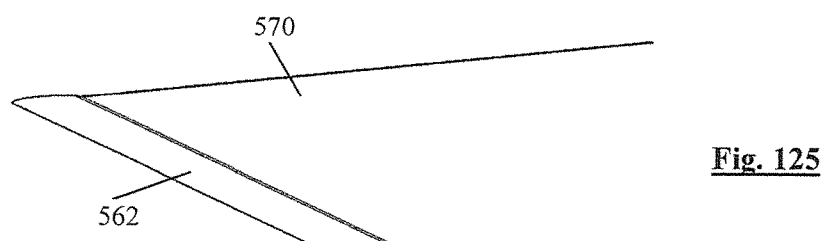
Fig. 125
Fig. 126
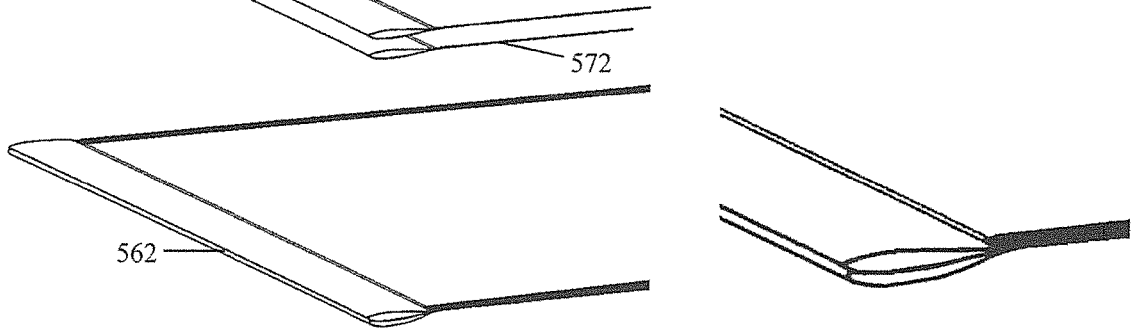
Fig. 127
Fig. 128

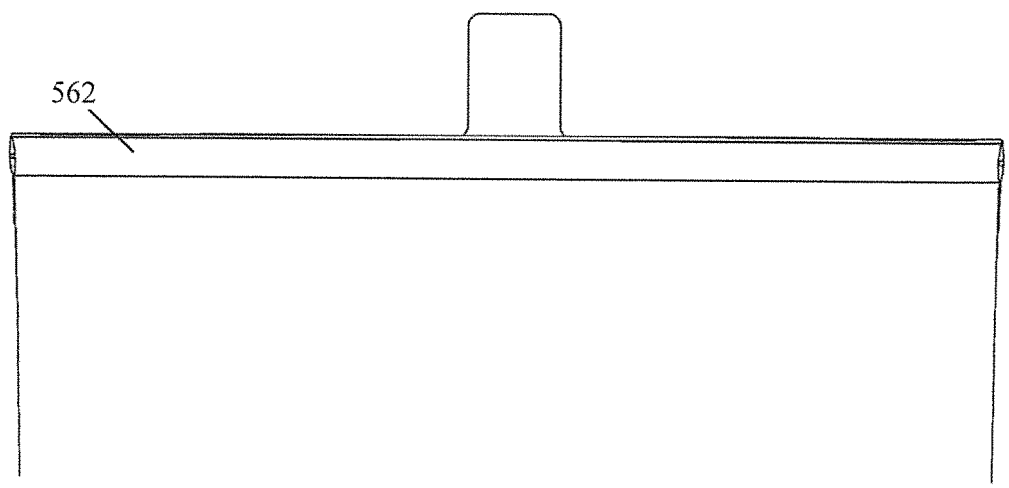
Fig. 129
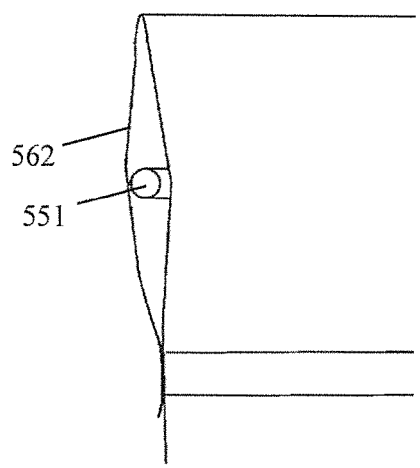
Fig. 130
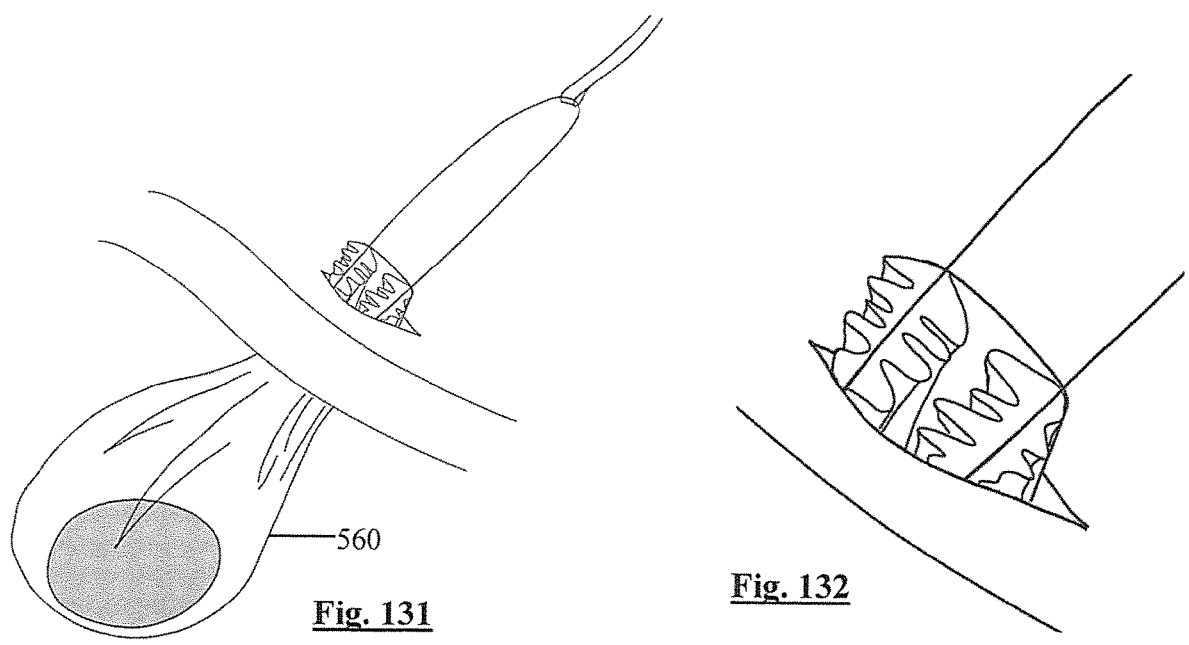
Fig. 131
Fig. 132

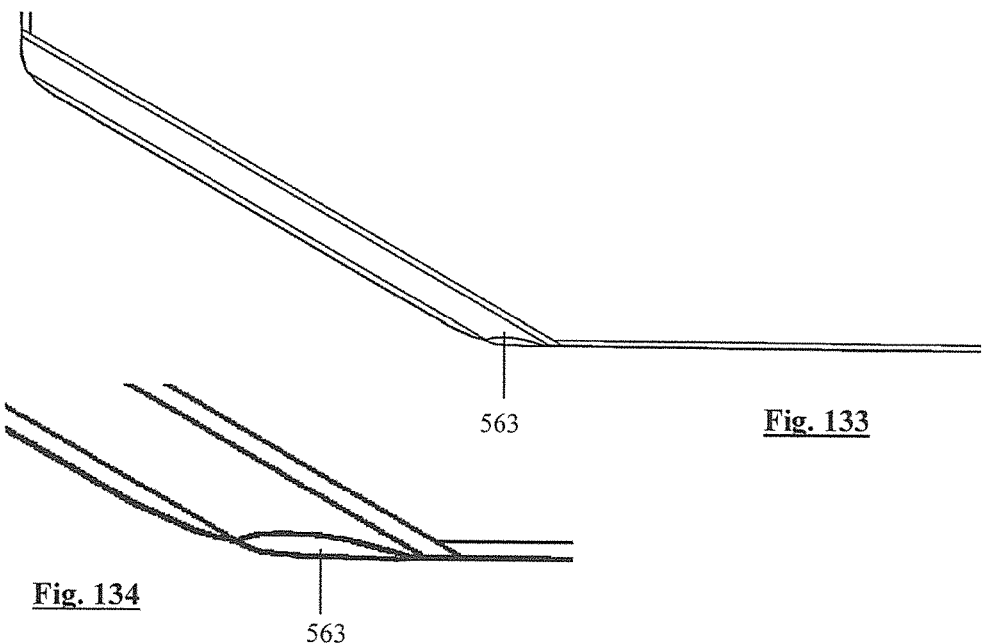
Fig. 133
Fig. 134
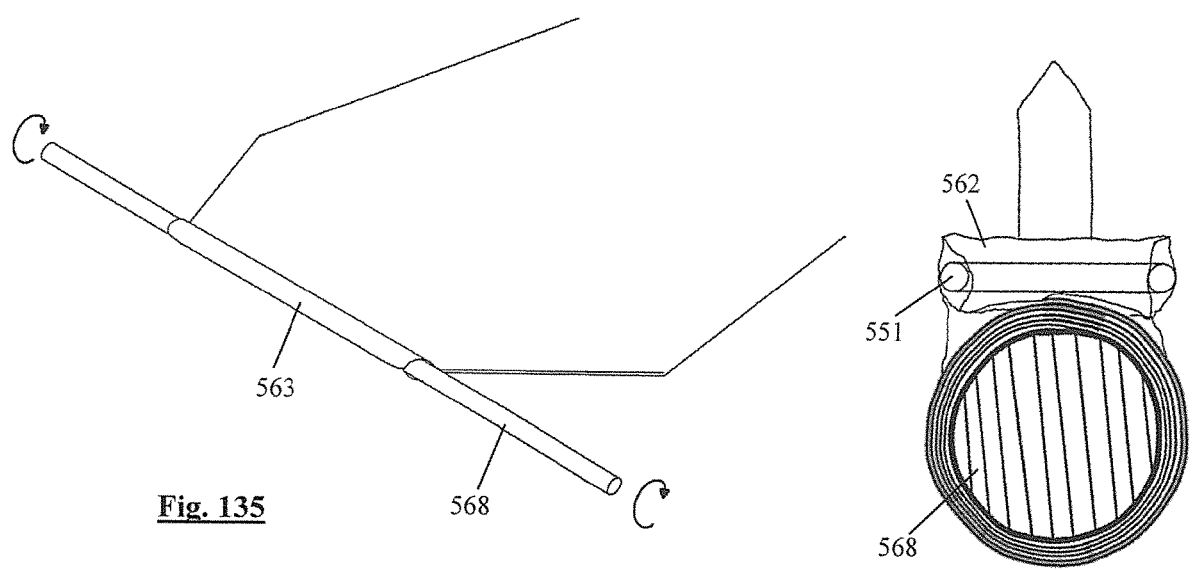
Fig. 135
Fig. 136

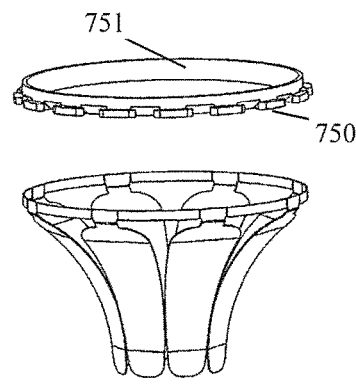
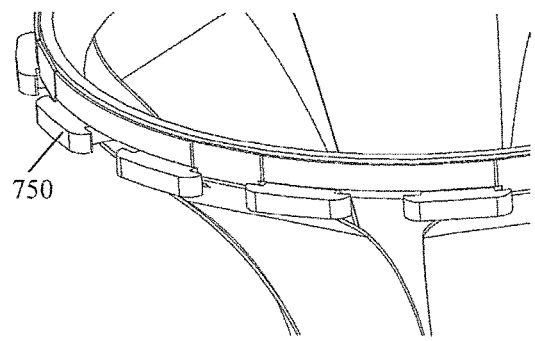
Fig. 177    Fig. 178
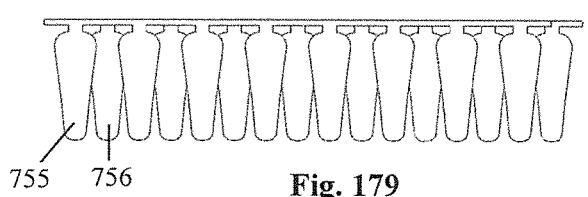
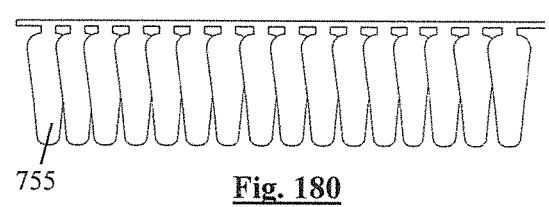
Fig. 179    Fig. 180
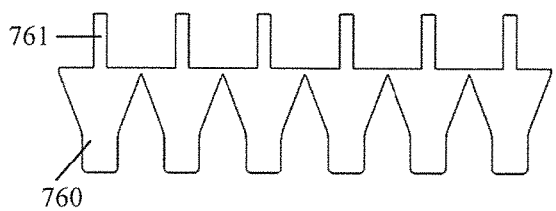
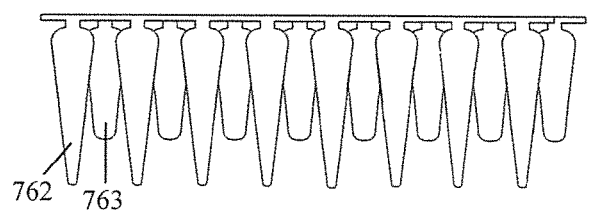
Fig. 181    Fig. 182
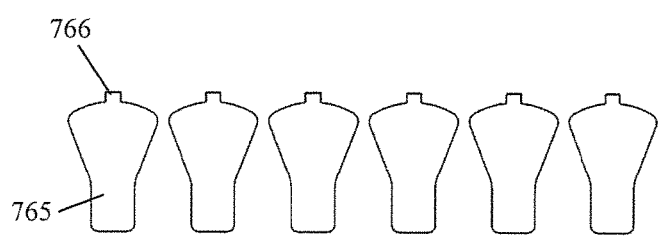
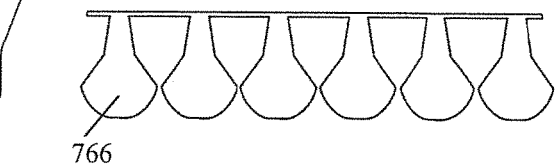
Fig. 183    Fig. 184

767  768

770

771  771

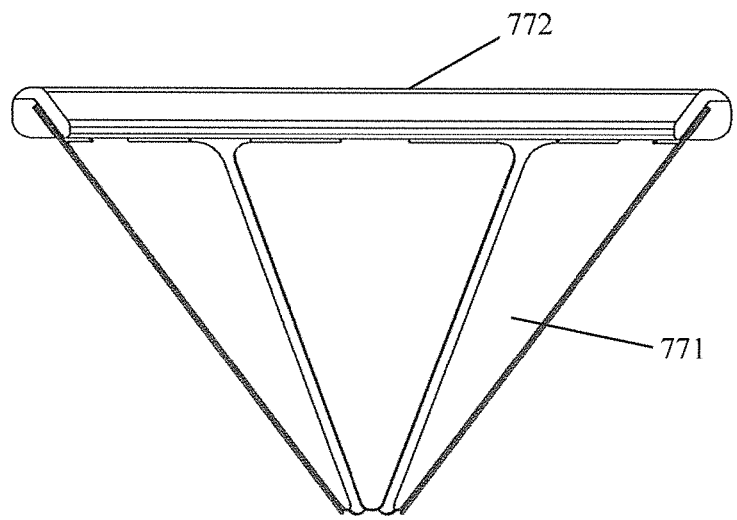
Fig. 189
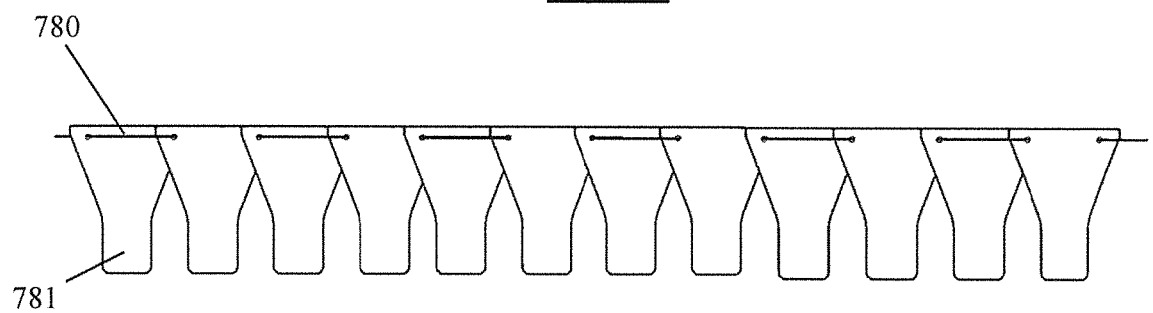
Fig. 190
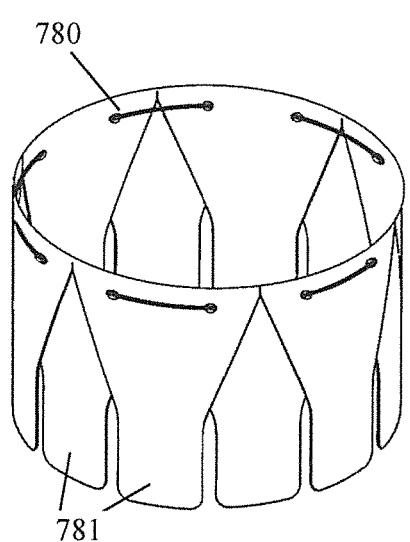 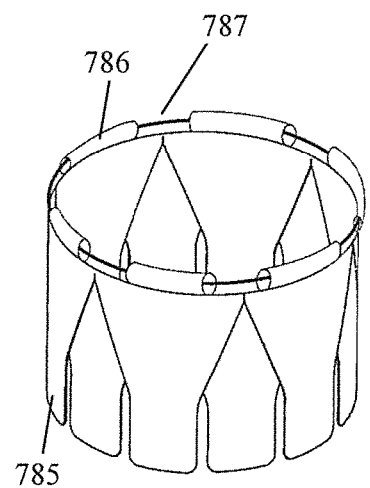
Fig. 191      Fig. 192

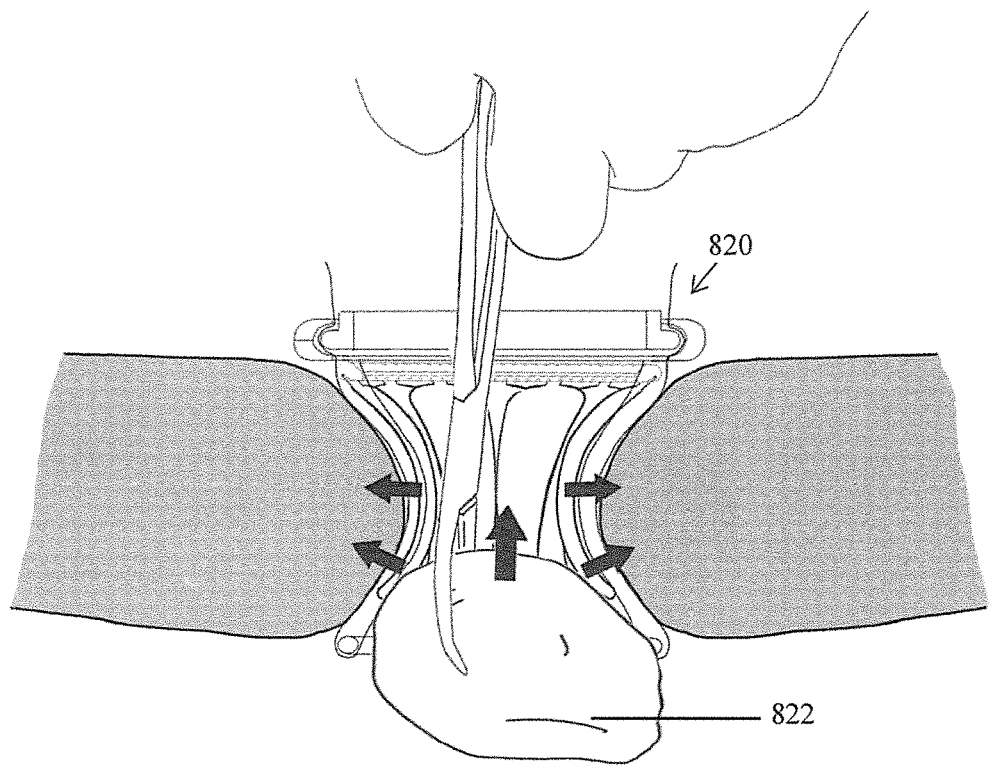
Fig. 220
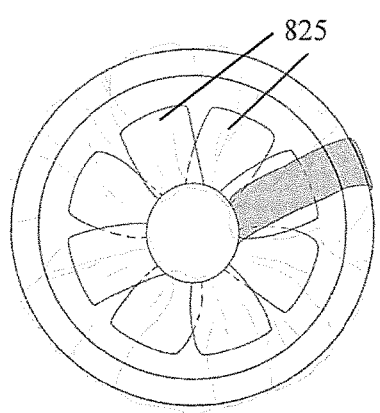 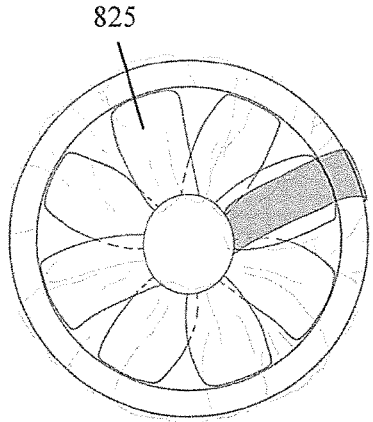 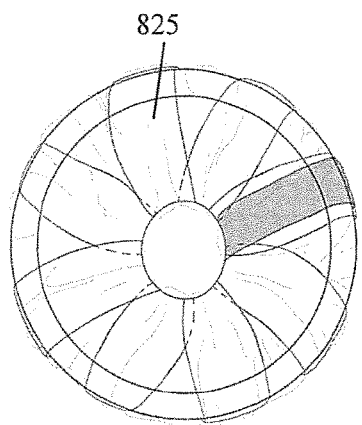
Fig. 221　　　　　　　　Fig. 222　　　　　　　　Fig. 223

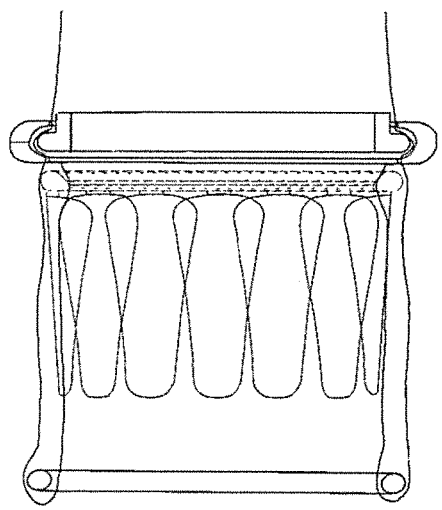
Fig. 232
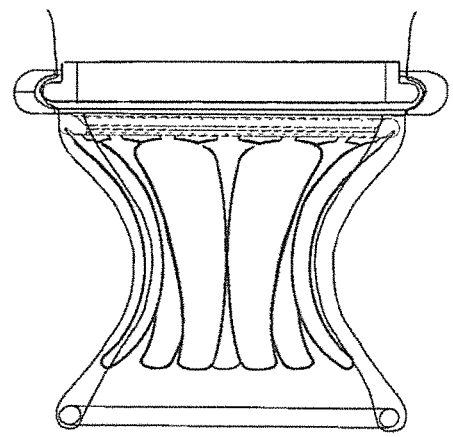
Fig. 233
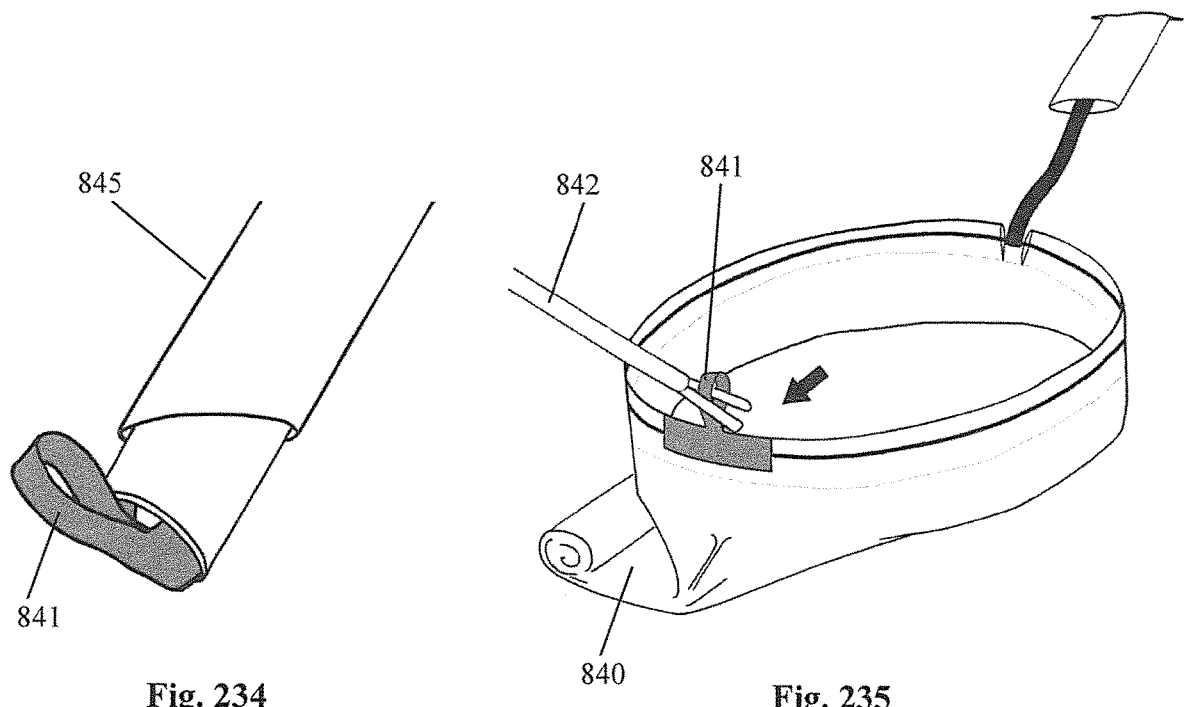
Fig. 234
Fig. 235

GUARD DEVICE FOR A TISSUE CONTAINMENT SYSTEM

CROSS-REFERENCE TO RELATED APPLICATION(S)

This application is the U.S. national phase entry under 35 U.S.C. § 371 of International Application No. PCT/EP2019/057290, filed on Mar. 22, 2019, which claims priority to each of European Patent Application 18168839.1, filed Apr. 23, 2018, European Patent Application 18177716.0, filed Jun. 14, 2018, European Patent Application 18196560.9, filed Sep. 25, 2018, European Patent Application 18200252.7, filed Oct. 12, 2018, and European Patent Application 19156867.4, filed Feb. 13, 2019, the contents of each of which is incorporated herein in its entirety.

This invention relates to a guard device and in particular to a guard device for a tissue containment system. In one case the invention relates to a guard device or shield to protect a tissue containment bag from damage during manual morcellation.

STATEMENTS OF INVENTION

According to the invention there is provided an apparatus for placement in an opening such as an incision or a natural body opening comprising:
  a retractor having an insertion configuration and a retracting configuration; and
  a guard device having an insertion configuration and a deployed configuration, the guard device being movable by the retractor from the insertion configuration to the deployed configuration as the retractor is moved to the retracting configuration.

In one case the retractor comprises a distal retractor member and a proximal retractor member and wherein the guard device in the deployed configuration is located between the distal retractor member and the proximal retractor member.

The guard device may be axially movable relative to the distal retractor member and/or the proximal retractor member on movement towards the deployed configuration.

In one case the retractor comprises a retracting sleeve.

In some cases the sleeve extends in two layers between the distal retractor member and the proximal retractor member and wherein the guard is located between the two layers of the sleeve. The sleeve may be wrapped around the distal retractor member.

The invention also provides a guard device for placement in an opening such as an incision or a natural body opening, the guard device comprising a plurality of individual petals, each petal having a proximal end, a distal end and a pair of side edges.

At least a portion of the side edges of adjacent petals may be overlapped.

The device may comprise a layer of petals for extending circumferentially around an opening.

In one case the guard device comprises a first layer of petals and at least one additional layer of petals. The petals of one layer may be overlapped with the petals of another layer.

In one case at least some of the petals are movable from a partially overlapped resting configuration to an increased overlapped configuration in response to a circumferential force applied to the petals.

At least some of the petals may comprise a proximal neck. The proximal neck may be configured to provide an inflection region to facilitate radial movement of the petal.

In some cases the guard device comprises a proximal mounting to which the petals are mounted. The mounting may comprise a proximal ring. The proximal ring may comprise mounting features for mounting the petals.

The invention also provides a tissue containment system comprising:
  a tissue containment bag, including:
    an open end,
    a closed end opposite to the open end,
    a wall extending from the open end to the closed end, wherein the wall has an interior surface, and
    a tissue containment chamber defined by the wall and the closed end;
  a guard for protecting at least part of the wall of the tissue containment bag;
  the guard having an exterior for engaging the interior surface of the wall; and
  an interior defining a passageway for receiving an instrument.

In one embodiment the guard is configured for anchoring the guard proximally. In one case the guard is configured for anchoring the guard to a proximal member.

In some cases the guard comprises a projection that extends radially outwardly of the exterior of the guard. The projection may extend circumferentially around the exterior of the guard. The projection may be movable from a retracted insertion configuration to an extended engagement configuration.

In some cases the projection is at a distal end of the guard. Alternatively, the projection is located intermediate the proximal and distal ends of the guard.

In one case the projection is integral with the guard. In another case the projection is a separate element from the guard.

In some embodiments the projection comprises a plurality of circumferentially spaced-apart elements.

In one case the guard comprises a tapered proximal portion at a proximal end of the guard. The proximal portion of the guard may be tapered outwardly in a proximal direction.

In some embodiments the guard comprises a distal skirt at a distal end of the guard. The skirt may be tapered outwardly in a distal direction. In some cases the skirt is mounted to the guard. The skirt may be releasably mounted to the guard.

The skirt may be movable from a retracted insertion configuration to an extended deployed configuration. In one case, the skirt is of a flexible material to facilitate movement between the retracted and deployed configurations.

In some embodiments the guard comprises a sheath of a flexible cut resistant material. The sheath may be mounted to a proximal member.

In one case the sheath is attached to a retractor sleeve.

At least a portion of the guard may be adjustable in length and/or in diameter and/or in circumference.

In one embodiment the guard comprises a plurality of individual petals which are at least partially radially overlapped. At least some of the petals may be movable from a partially overlapped resting configuration to an increased overlapped configuration in response to a circumferential force applied to the petals.

In some cases the guard is configured to retract an incision.

The invention also provides a tissue containment system which comprises a retractor. In some cases the guard comprises a part of the retractor.

The retractor may comprise an outer proximal ring and an inner proximal ring which is releasably engageable with the outer proximal ring.

The guard may comprise the inner proximal ring. The inner proximal ring may be integral with the guard.

The tissue containment system may comprise a releasable mounting for mounting the guard to a proximal member. The mounting may comprise snap fit projections.

The guard may comprise a sheath of a flexible and/or malleable cut resistant material.

The invention also provides a device for placement in an incision comprising a plurality of circumferentially extending individual petals which are at least partially radially overlapped. At least some of the petals may be movable from a partially overlapped resting configuration to an increased overlapping configuration in response to a circumferential force applied to the petals.

Also provided is a tissue guard comprising a device of the invention.

The invention also provides a retractor comprising a device of the invention.

The invention also provides a device comprising a first blank comprising a first sheet having a plurality of first petals and a second blank comprising a second sheet having a plurality of second petals wherein the first and second sheets are arranged such that at least some of the second petals at least partially overlap at least some of the first petals.

A proximal end of the first sheet may be attached to a ring.

A proximal end of the second sheet may be attached to a ring.

In one case the first and second sheets are attached to a common ring.

In some cases the petal comprises a region having a narrowed width. The narrowed width region may be towards a distal end of the petal.

Also provided is a blank for forming a tissue guard comprising a sheet having a plurality of petals.

The invention provides a tissue guard for placement in an incision comprising a plurality of petals which are at least partially overlapped.

At least some of the petals may be movable from a resting configuration to an overlapping configuration in response to a circumferential force applied to the petals. In some cases at least some of the petals are overlapped in the resting configuration and the overlap is increased in response to a circumferential force applied to the petals.

The tissue guard may comprise a mounting ring from which the petals extend. The petals may be attached to the mounting ring. In one case he mounting ring is a proximal mounting ring.

The mounting ring may be substantially rigid or semi-rigid.

The petals may comprise a proximal end and a distal end and a region of increased width. The region of increased width may be intermediate the proximal and distal ends. In one case the petal comprises a narrowed width region. The narrowed width region may be towards the distal end of the petal and/or the narrowed width region is towards the proximal end of the petal.

In some embodiments the petals are of arcuate shape in plan view. The petals may be preformed into the arcuate shape.

In some cases the petals have a length of from 15 to 60 mm, usually length of from 25 to 45 mm.

In some cases the diameter of the mounting ring is from 40 to 80 mm, usually from 50 to 70 mm.

The petals may have a thickness of from 0.1 to 1.5 mm, optionally from 0.2 to 0.5 mm.

The invention also provides a tissue containment system comprising a tissue guard of the invention and a tissue containment bag.

In some cases the tissue containment bag includes:
an open end,
a closed end,
a closed end opposite to the open end,
a wall extending from the open end to the closed end wherein the wall has an interior surface, and
a tissue containment chamber defined by the wall and the closed end;
the petals of the tissue guard being adapted to protect at least part of the wall of the tissue containment bag, the tissue guard having an exterior to protect the interior surface defining a passage for receiving an instrument such as a scalpel.

The tissue containment bag in some cases is generally cylindrical having a length in the range of from 250 to 500 mm and a diameter in the range of from 50 to 250 mm.

The tissue containment bag may comprise a proximal cuff and a biasing element to bias the cuff into an open configuration. The biasing element may be undersized with respect to the cuff.

The tissue containment bag may comprise a distal cuff for receiving an element around which the bag is wrapped into a reduced diameter introduction configuration.

Also provided is a tissue containment system of the invention and a retractor.

In some cases the retractor comprises:
a distal member;
a proximal member;
a sleeve extending at least between the distal member and the proximal member;
a guide member for a proximal portion of the sleeve;
a first sleeve portion extending distally from the proximal member to the distal member; and
a second sleeve portion extending proximally from the distal member to the guide member.

The tissue guard may comprise a mounting ring which is located between the first and second sleeve portions.

The sleeve may comprise a proximal portion for pulling the sleeve upwardly to shorten an axial extent between the distal member and the proximal member. The guard mounting ring may be movable upwardly as the sleeve is pulled upwardly.

In some cases the guide member comprises a proximal guide ring and the proximal member comprises a proximal ring member.

The guard mounting ring may have a diameter of the proximal ring member of the retractor.

The guide member may be adapted to accommodate and retain the proximal member. The guide member may comprise a proximal guide ring and the proximal member comprises a proximal ring member.

In some cases the sleeve comprises a longitudinally extending line of weakness or a tear line to convert a portion of the sleeve extending proximally of the proximal member into a split sleeve. The line of weakness may comprise perforations.

The invention further provides a retractor system comprising a retractor and a tissue guard of the invention. The tissue guard may comprise a mounting ring to which the petals of the tissue guard are attached. The retractor may comprise:
- a distal member;
- a proximal member;
- a sleeve extending at least between the distal member and the proximal member;
- a guide member for a proximal portion of the sleeve;
- a first sleeve portion extending distally from the proximal member to the distal member;
- a second sleeve portion extending proximally from the distal member to the guide member;
- the guard mounting ring being located between the first and second sleeve portions.

In one case the sleeve comprises a proximal portion for pulling the sleeve upwardly to shorten an axial extent between the distal member and the proximal member. The guard mounting ring may move automatically upwardly as the sleeve is pulled upwardly.

The guide member may be adapted to accommodate and retain the proximal member. The guide member may comprise a proximal guide member and the proximal member comprises a proximal ring member. The guard mounting ring may have a diameter which is less than the diameter of the proximal ring member.

In some cases the sleeve comprises a longitudinally extending line of weakness or a tear line to convert a portion of the sleeve extending proximally of the proximal member into a split sleeve.

According to the invention there is provided a guard device for placement in an opening such as an incision or a natural body opening, the guard device comprising a plurality of individual petals, each petal having a proximal end, a distal end and a pair of side edges.

At least a portion of the side edges of adjacent petals may be overlapped.

The guard device in one case comprises a layer of petals for extending circumferentially around an opening. There may be a first layer of petals and at least one additional layer of petals. In some cases the petals of one layer are overlapped with the petals of another layer.

In one case at least some of the petals are movable from a partially overlapped resting configuration to an increased overlapped configuration in response to a circumferential force applied to the petals.

At least some of the petals may comprise a proximal neck. The proximal neck may be configured to provide an inflection region to facilitate radial movement of the petal.

In some cases the guard device comprises a proximal mounting to which the petals are mounted.

The mounting in one case comprises a proximal ring. The proximal ring may comprise mounting features for mounting the petals.

In one case there are a plurality of mounting features which are circumferentially spaced-apart. The mounting features may extend radially inwardly and/or outwardly of the proximal ring.

In one case the mounting features are adapted for engagement with the petals. For example, the mounting features are adapted for engagement with a proximal linking element from which the petals extend.

In one case the proximal mounting comprises a first proximal ring and a second proximal ring. The first and second rings in some cases are engaged to secure the proximal ends of the petals.

In some cases the guard device comprises a proximal linking element extending between the petals. The linking element may be mounted to the proximal mounting.

In another case the mounting comprises a wire. The wire may be threaded through overlapped petals.

The wire may be a proximal wire towards the proximal end of the petals and/or the wire is a distal wire towards the distal end of the petals.

In some cases the petals are mounted on clips which are mounted to the mounting ring.

The mounting may comprise a mounting ring to which the petals are directly attached. The mounting ring may comprise a groove or slot for reception of petals. In some cases the groove is angled radially inwardly to direct the petals inwardly.

In some cases the petals are of a flexible cut resistant material.

Typically, the petals have a length of from 15 to 60 mm, such as a length of from 25 to 45 mm.

Typically, the petals have a thickness of from 0.1 to 1.5 mm, such as a thickness of from 0.2 to 0.5 mm.

The invention also provides a tissue containment system comprising a guard device of the invention and a tissue containment bag.
- the tissue containment bag may include:
- an open end,
- a closed end opposite to the open end,
- a wall extending from the open end to the closed end wherein the wall has an interior surface, and
- a tissue containment chamber defined by the wall and the closed end;
- the petals of the guard device being adapted to protect at least part of the wall of the tissue containment bag, the guard device having an exterior to protect the interior surface defining a passage for receiving an instrument such as a scalpel.

The tissue containment bag may be generally cylindrical having a length in the range of from 250 to 500 mm and a diameter in the range of from 50 to 250 mm.

The tissue containment bag may comprise a proximal cuff and a biasing element to bias into an open configuration. In one case the biasing element is undersized with respect to the cuff.

In one case the tissue containment bag comprises a distal cuff for receiving an element around which the bag is wrapped into a reduced diameter introduction configuration.

The bag may comprise a taper adjacent to the proximal opening of the bag.

The bag may comprise pull ring attached to the biasing element to aid retrieval of the bag into the mouth of a trocar.

The tissue containment system in some cases also comprise and a retractor.

In one case the retractor comprises:
- a distal member;
- a proximal member;
- a sleeve extending at least between the distal member and the proximal member;
- a guide member for a proximal portion of the sleeve;
- a first sleeve portion extending distally from the proximal member to the distal member; and
- a second sleeve portion extending proximally from the distal member to the guide member.

The guard device may comprise a mounting ring which is located between the first and second sleeve portions. The sleeve may comprise a proximal portion for pulling the sleeve upwardly to shorten an axial extent between the distal member and the proximal member. The guard mounting ring may be movable upwardly as the sleeve is pulled upwardly.

In another case the guard device further comprises a sleeve to which the petals are mounted. The sleeve may be a retracting sleeve. The petals may be mounted to the inner face of the sleeve. The sleeve may be a single layer retracting sleeve.

Also provided is a retractor comprising a guard device of the invention.

The invention also provides a blank for forming a guard device, the blank comprising a sheet comprising a plurality of petals.

The sheet may comprise a proximal linking portion extending between the petals.

In one case the blank comprises a first array of petals and a second array of petals and wherein there is an enlarged gap between the first array and the second array to facilitate overlap of the petals.

BRIEF DESCRIPTION OF THE DRAWINGS

The invention will be more clearly understood from the following description thereof, given by way of example only, in which:

FIGS. 50 to 51 illustrate another sheath guard mounted to an inner proximal ring and a retractor sleeve;

FIG. 52 is a cross sectional view of a retractor in which a sleeve of the retractor forms a guard;

FIG. 96 is a view of the guard of FIGS. 81 to 91 mounted to a retractor;

FIG. 97 is another view of the guard and a retractor in which a retractor sleeve is omitted;

FIG. 98 illustrates the guard and a retractor being delivered through an incision;

FIG. 124 is an elevational view of the bag;

FIGS. 125 to 128 illustrate formation of the containment bag;

FIG. 129 is a sectional view through the upper end of a containment bag;

FIG. 130 is an enlarged view of an upper end detail of the bag;

FIGS. 131 and 132 illustrate the containment bag, in use;

FIGS. 133 and 134 show a bottom end of the bag;

FIG. 135 illustrates a rod inserted through a loop at the bottom end of the bag;

FIG. 136 illustrates a containment bag rolled tightly, for introduction;

FIGS. 176 to 178 illustrate features of a mounting ring to which the guard is mounted;

FIG. 179 illustrates overlapping of guard petals;

FIG. 180 illustrates another overlapping arrangement;

FIG. 181 illustrates petals with elongated necks;

FIG. 182 illustrates petals of varying lengths;

FIGS. 183 to 186 illustrate various alternative petals;

FIG. 189 shows the petal arrangement of FIGS. 187 to 188 mounted to a mounting ring;

FIGS. 190 and 191 illustrate the mounting of petals to a wire;

FIG. 192 shows alternative petals mounted to a wire;

FIGS. 217 to 220 illustrate a guard, a retractor and a tissue containment bag, in use;

FIGS. 221 to 224 are views taken from within the bag looking upward within different sized abdomens;

FIGS. 225 and 226 illustrate a guard of the invention in use in a natural body orifice;

FIG. 227 illustrates a tissue containment bag in use with the guard in a natural body orifice;

FIGS. 228 to 231 show a guard of the invention in use without a tissue collecting bag;

FIGS. 232 and 233 illustrate a tissue guard of the invention in use within a retractor;

FIGS. 234 and 235 show a tissue collection bag with a distal tab loop;

FIGS. 236 and 237 is a view of a tissue collection bag with a taper;

FIGS. 238 to 243 illustrates a feature of a tissue collection bag to facilitate closing laparoscopically; and FIG. 244 illustrates an array of different features in which the length, inner diameter and location of tether and wire holes are varied.

DETAILED DESCRIPTION

A tissue containment bag is used to safely reduce and remove resected tissue from within the abdomen via small incisions. An example of such a tissue containment bag is described in WO2014/207077A, the entire contents of which are incorporated herein by reference.

Figure 1:
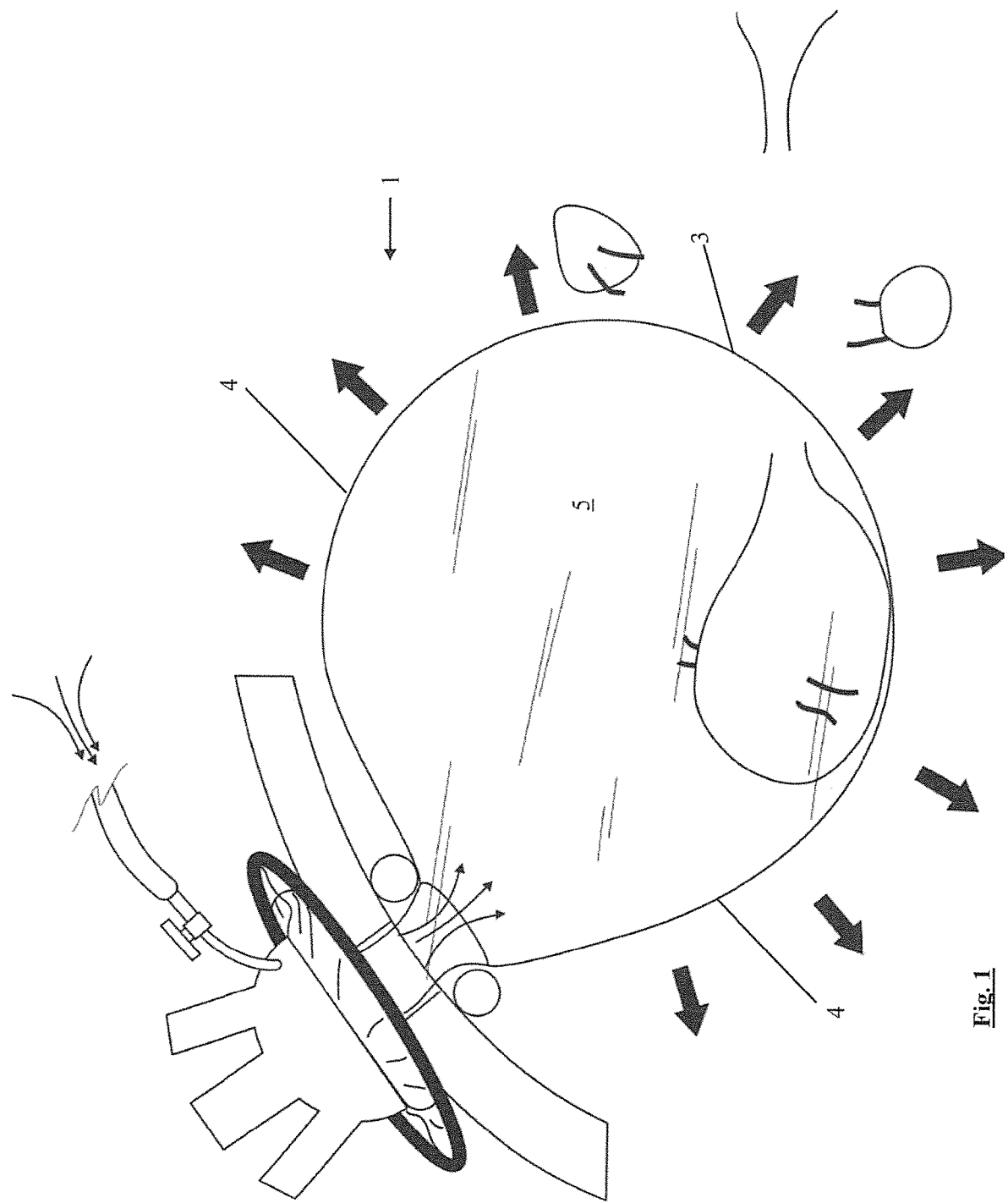
FIG. 1 is a diagram of a known tissue containment bag, in use.
Figure 2:
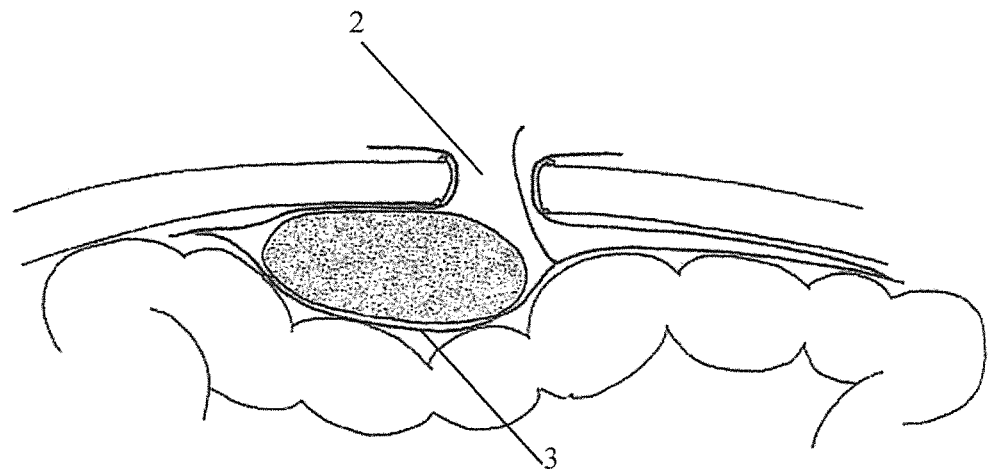
FIGS. 2 and 3 are illustrations of the containment bag of FIG. 1 in different stages of use.
Figure 3:
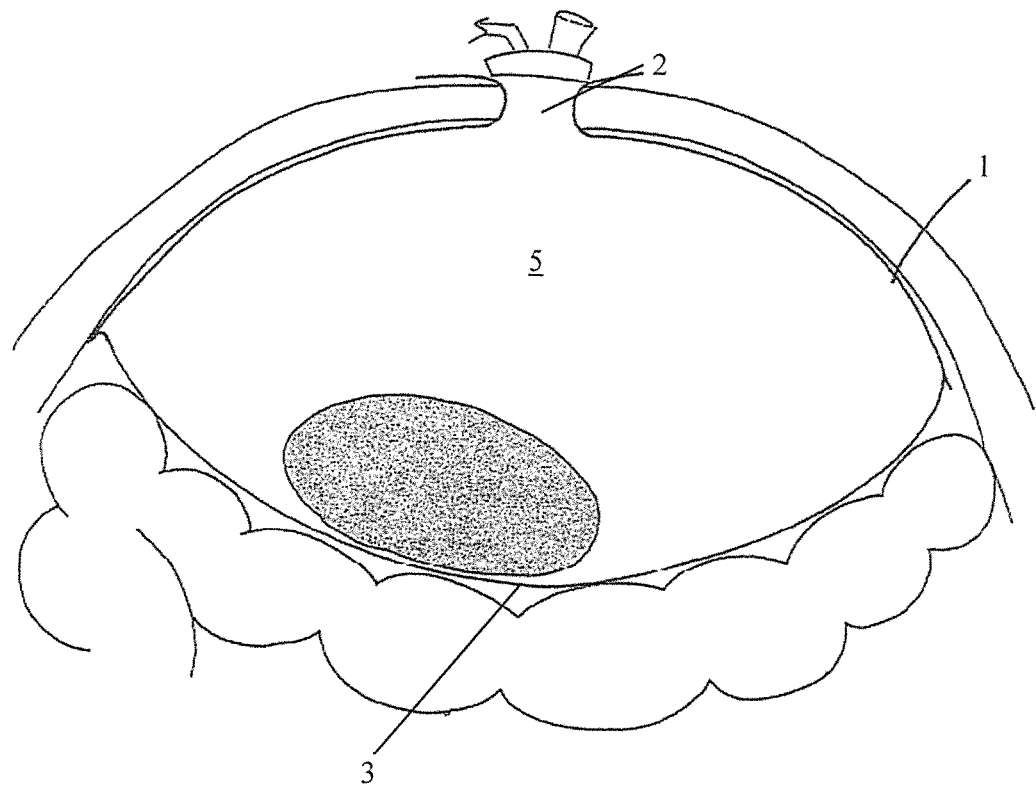

One example of such a containment bag is illustrated in FIGS. 1 to 3.

In general, a tissue containment bag 1 includes an open end 2, a closed end 3 opposite to the open end, a wall 4 extending from the open end to the closed end, and a tissue containment chamber 5 defined by the wall and the closed end.

In some cases the tissue containment bag 1 may be mounted to a retractor. An exemplar retractor is described in US2005/0090717A, the entire contents of which are incorporated herein by reference.

Figure 4:
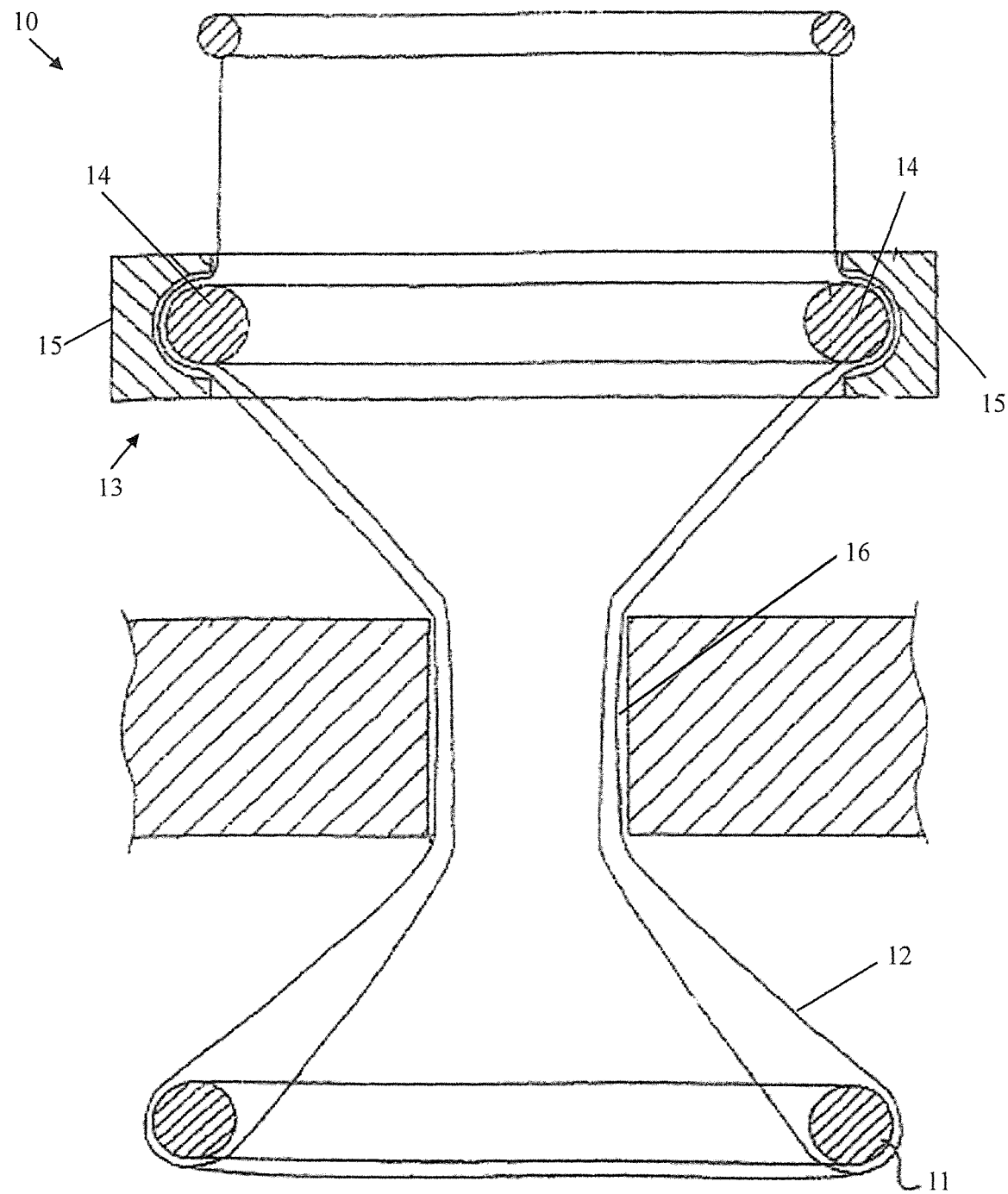
FIG. 4 is a cross sectional view of a known retractor.

One example of such a retractor is illustrated in FIG. 4. The illustrated retractor 10 comprises a distal anchoring ring 11, a retractor member such as a sleeve 12, and a proximal ring assembly 13 which in this case comprises an inner proximal ring 14 and an outer proximal ring 15. The retractor may be employed to retract laterally the side of a wound opening.

The tissue containment bag may be used with an access port. An exemplar access port is described in US2009/0036745A, the entire contents of which are incorporated herein by reference.

Figure 5:
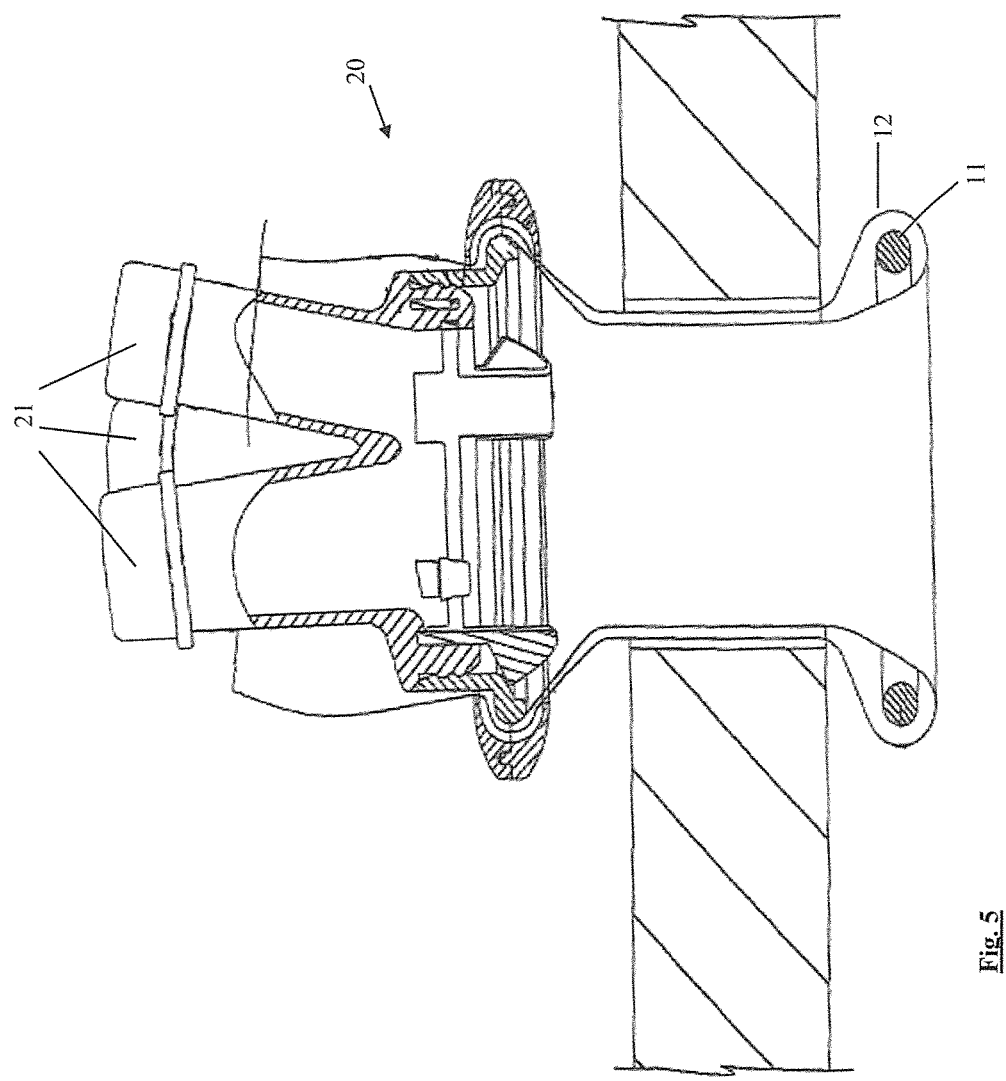
FIG. 5 is a cross sectional view of a known access port mounted to a retractor.

Referring to FIG. 5, in some cases the proximal end of a retractor 10 may be closable by a cap which in some cases comprises an instrument access device 20. The access device 20 may be releasably mountable to the proximal ring assembly 13 of the retractor. The access device may have a number of access ports 21 which may provide a seal around an instrument extended through the access device.

The invention provides a guard or shield to protect a tissue containment bag from damage/perforation during manual morcellation, whereby tissue is reduced/morcellated manually within the incision using a scalpel blade in a cutting motion. The guard protects the portions of the bag most vulnerable during manual morcellation by providing a tougher portion of material or cut resistance surface between the cutting blade and the tissue containment bag.

In some cases the guard has an exterior 25 for engaging the interior surface of the wall of a bag and an interior 26 defining a passageway for receiving an instrument.

Figure 6:
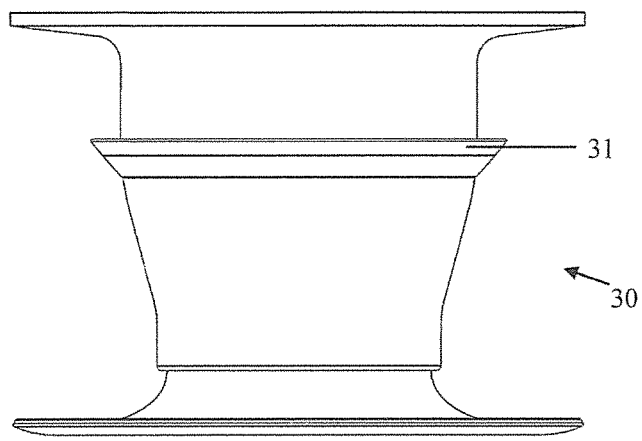
FIG. 6 is a view of a guard for a tissue containment system of the invention.
Figure 7:
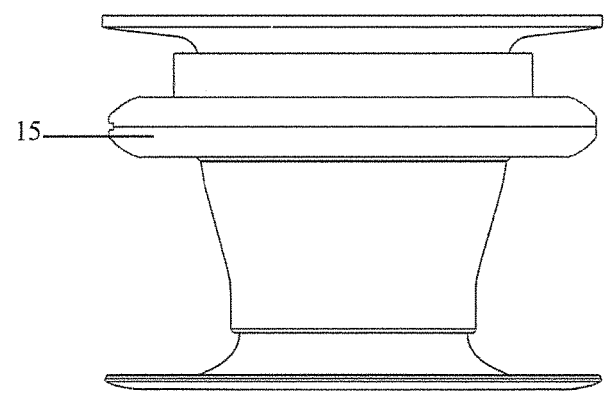
FIG. 7 is a view of the guard of FIG. 6 mounted to a proximal member.
Figure 8:
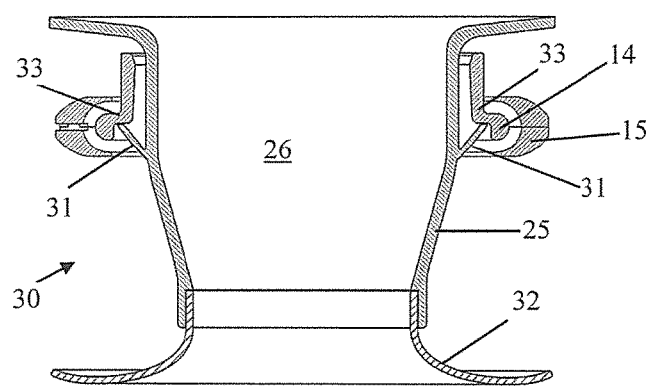
FIG. 8 is a cross sectional view of FIG. 7.

FIGS. 6 to 8 illustrate a snap in manual morcellation shield 30 that is rigid or semi-rigid and can be made from one or more different materials. The shield has a circumferential barb 31 that engages with the inner proximal ring 14 of a base retractor so it does not slip out during use. The shield may be in varying opening sizes to fit a single size base retractor or can be made in varying sizes to suit different size base retractors for the same opening size, or a combination of both. The shield also has a distal feature comprising a skirt-like component 32 that opens out. When pressed into the base retractor, the barb 31 locks on the underside of the inner proximal ring 14 or similar proximal component. FIG. 8 shows the barb 31 engaged with the inner proximal ring 14 of the base retractor. However, the barb may be engaged with any suitable proximal component. The barb 31 is biased in one direction like a snap fit feature so that it flexes as the device is being inserted. When the barb 31 passes a projection 33, it locks underneath the inner proximal ring 14 as shown. In order to remove the shield again, the barb 31 is manipulated or flexed to release the lock.

Figure 9:
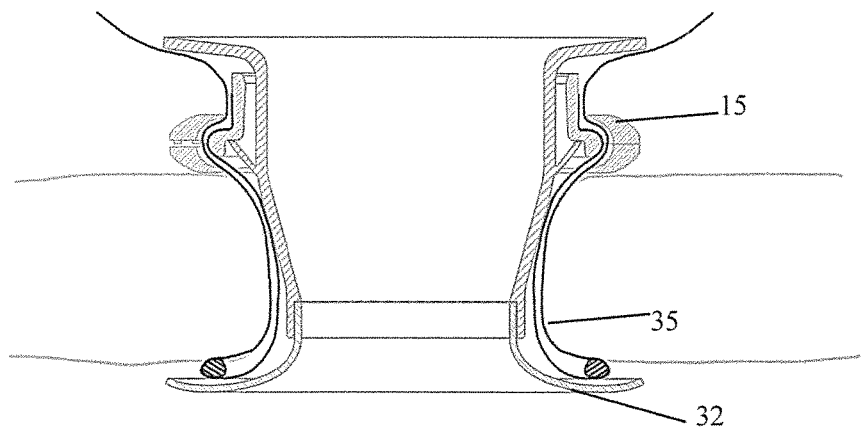
FIG. 9 is a cross sectional view of the guard and a retractor.

FIG. 9 illustrates the use of the shield with a base retractor having a sleeve 35. The sleeve 35 is stretched around the upper portion of the shield or split to avoid obstructing the proximal opening.

Figure 10:
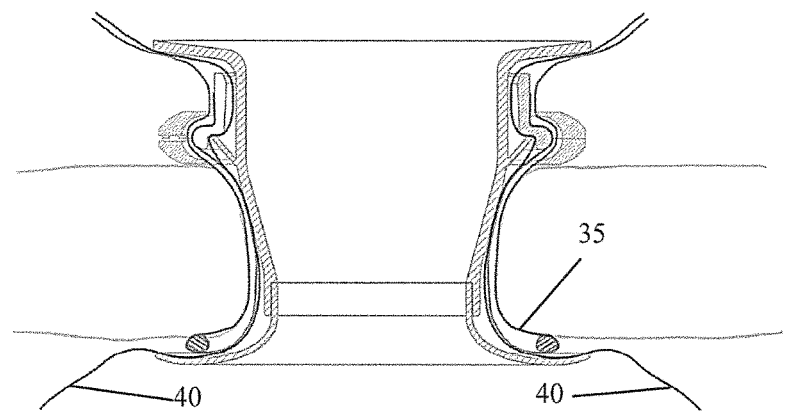
FIG. 10 is a cross sectional view of the guard, a retractor and portion of a tissue containment bag in one configuration.

FIG. 10 shows the inclusion of a tissue containment bag 40. In this image the tissue containment bag 40 is inside the base retractor and therefore between the shield and base retractor.

Figure 11:
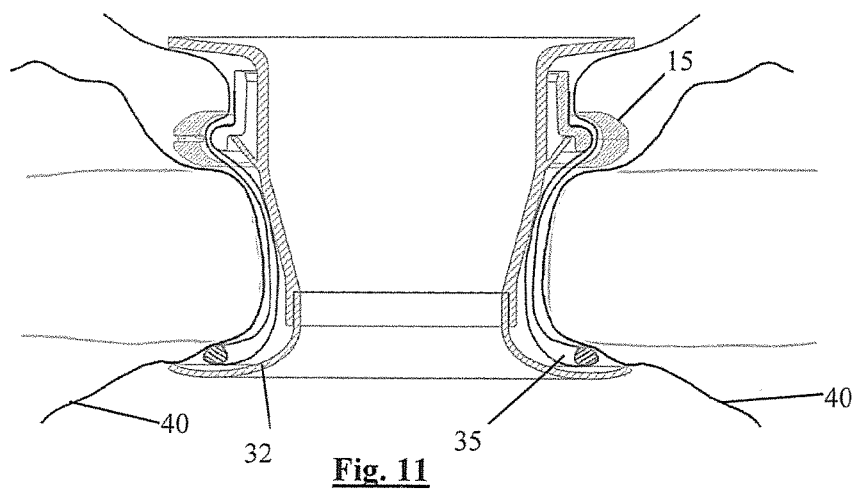
FIG. 11 is a cross sectional view of the guard, a retractor and portion of a tissue containment bag in another configuration.

FIG. 11 also illustrates the inclusion of a tissue containment bag 40. In this image the tissue containment bag 40 is outside the base retractor and therefore between the base retractor and the abdomen. It will be apparent that the distal skirt feature 32 is configured to push bag material away for the incision opening. This assists in protecting the bag material encroaching into the path of a cutting blade during manipulation of the tissue.

Figure 12:
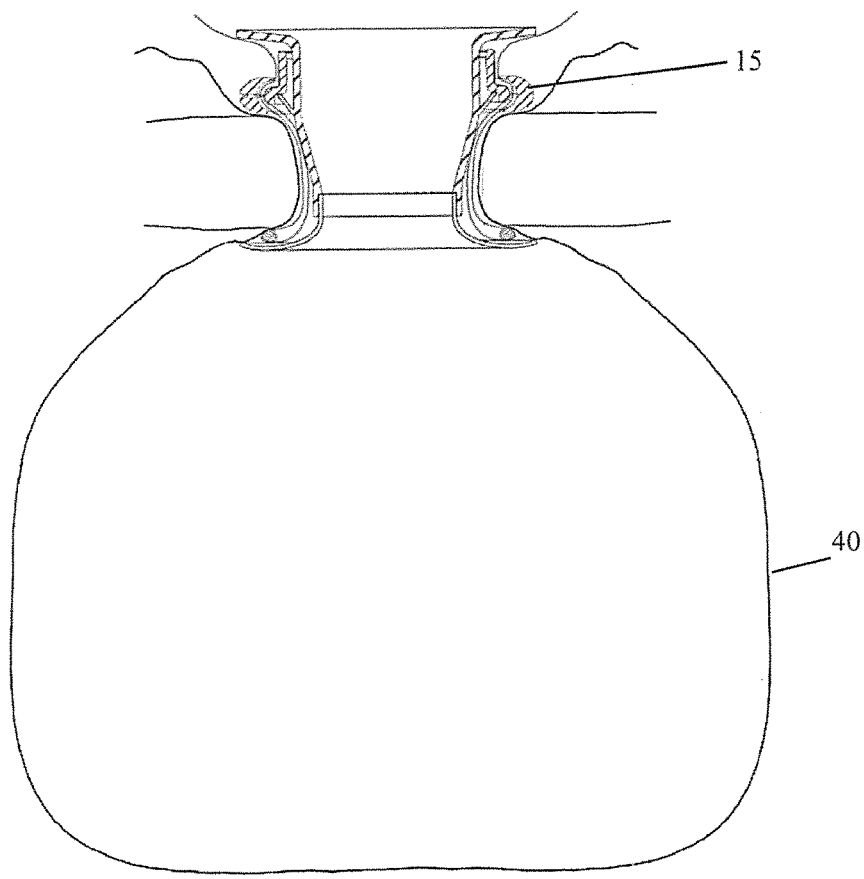
FIG. 12 is another view similar to FIG. 11 showing the full tissue containment bag.

FIG. 12 is a full view of the tissue containment bag 40. In this image tissue containment bag 40 is outside the base retractor and therefore between the base retractor and the abdomen.

Figure 13:
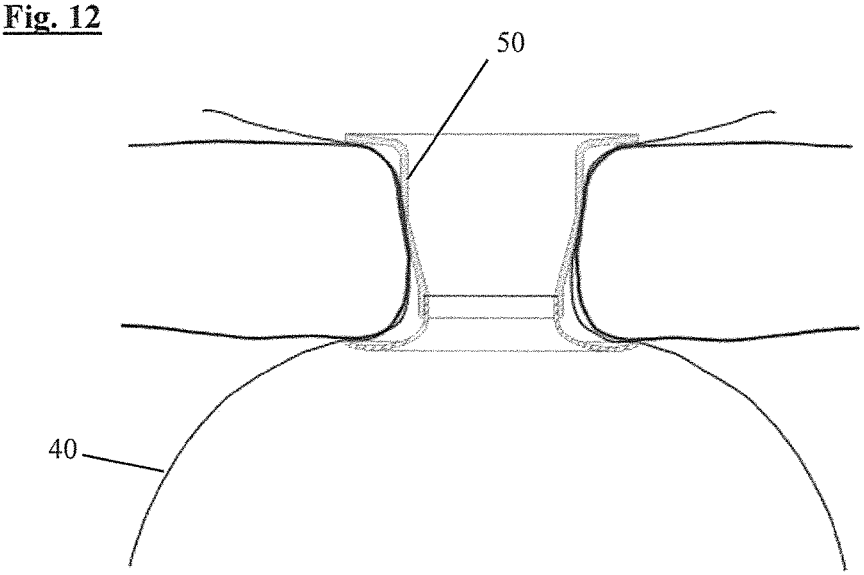
FIG. 13 is a cross sectional view of another guard according to the invention.

FIG. 13 illustrates a shield 50 in use without a separate base retractor and provides a combined shield and wound retractor.

Figure 14:
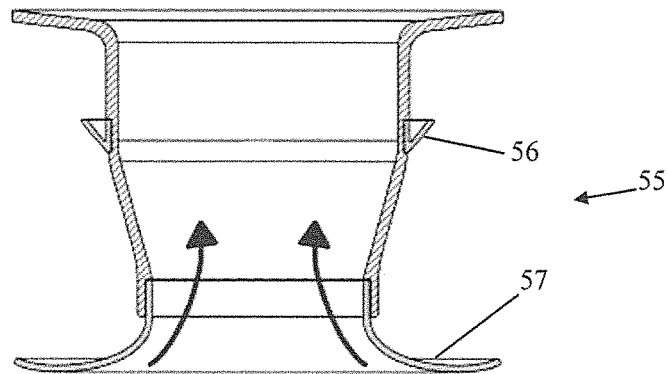
FIG. 14 is a cross sectional view of another guard according to the invention.

FIG. 14 illustrates another shield 55 with a locking barb 56 and a distal skirt 57. The distal shirt may be releasably mounted to the main body of the shield.

Figure 15:
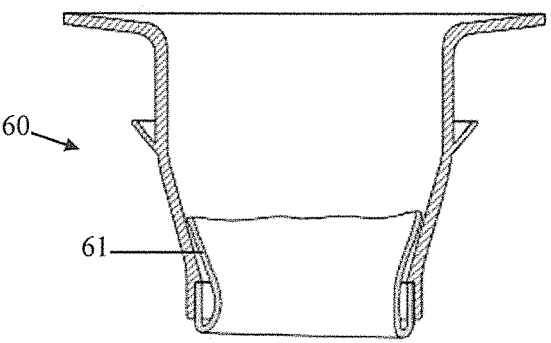
FIGS. 15 to 17 are cross sectional views of a further guard in different configurations of use.
Figure 16:
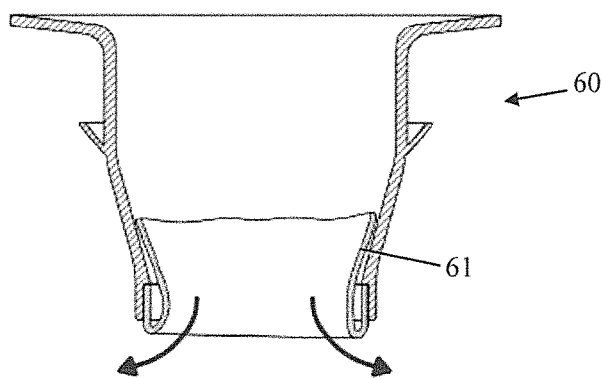

FIGS. 15 and 16 illustrate a shield 60 having a distal skirt 61 which may be more flexible than the main body of the shield and therefore can be tucked up in to the main body of the shield during insertion to make insertion easier. Once inserted into place, the more flexible skirt 61 can be deployed in order to protect the bag at the distal side.

Figure 17:
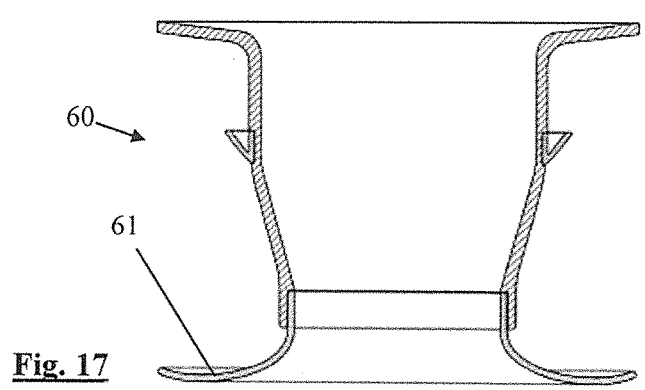

Referring to FIG. 17, the skirt feature 61 may serve to lock the shield into place in the incision in some cases.

Figure 18:
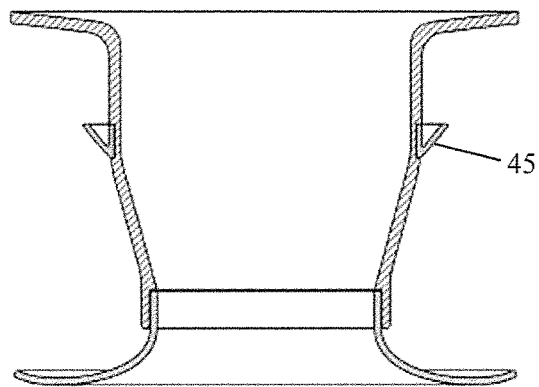
FIG. 18 is a cross sectional view of another guard according to the invention.
Figure 20:
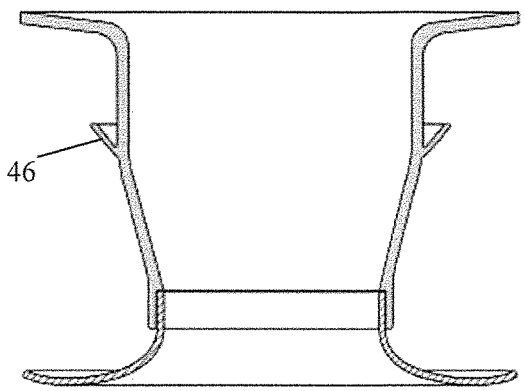
FIG. 20 is a cross sectional view of a further guard of the invention.
Figure 19:
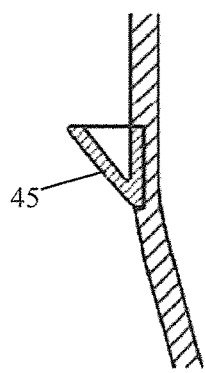
FIG. 19 is an enlarged view of a detail of the guard of FIG. 18.
Figure 21:
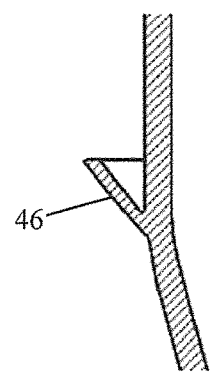
FIG. 21 is an enlarged view of a detail of FIG. 20.
Figure 22:
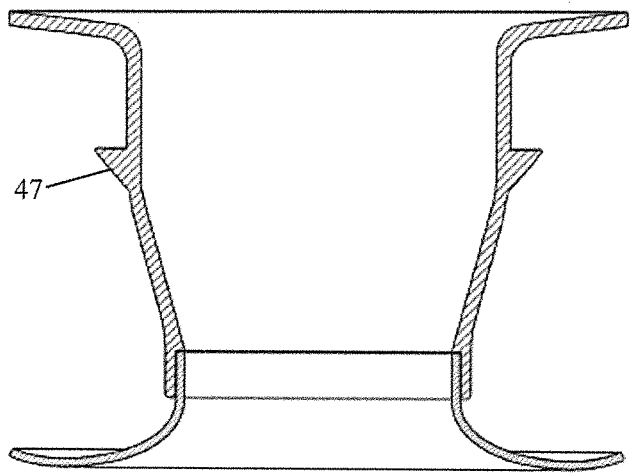
FIG. 22 is a cross sectional view of another guard of the invention.

FIGS. 18 to 33 illustrate different barb configurations. FIGS. 18 and 19 illustrate a barb 45 made from the same or different material as that of the main body of the shield but as a separate component attached to the main body. FIGS. 20 and 21 illustrate a barb 46 made from the same material as the main body of the shield and is part of the main body itself. FIG. 22 illustrates a more rigid barb 47 rather than a thin flexible arm.

Figure 23:
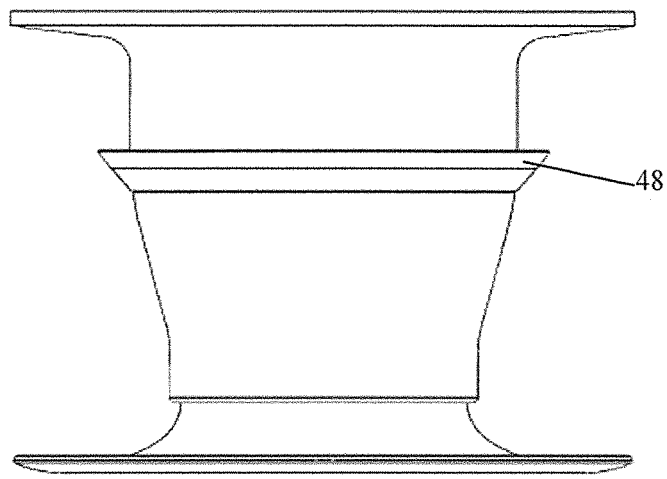
FIG. 23 is a view of a guard with a projection that extends circumferentially fully around the periphery of the barb.

FIG. 23 illustrates a barb 48 that extends fully circumferentially.

Figure 24:
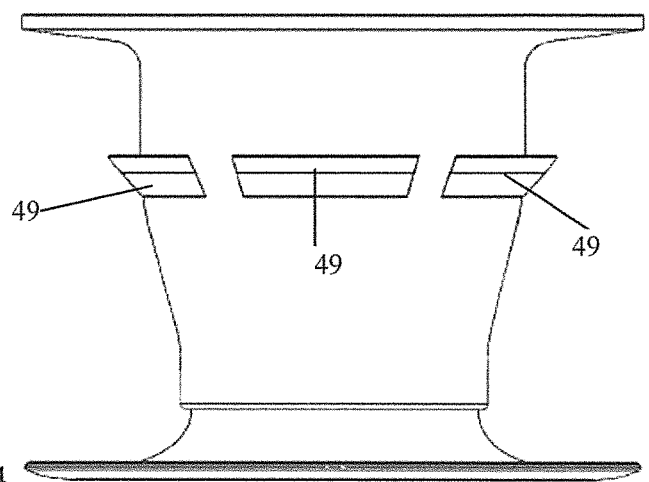
FIGS. 24 to 26 are views of another guard comprising a number of circumferentially spaced-apart projections.
Figure 25:
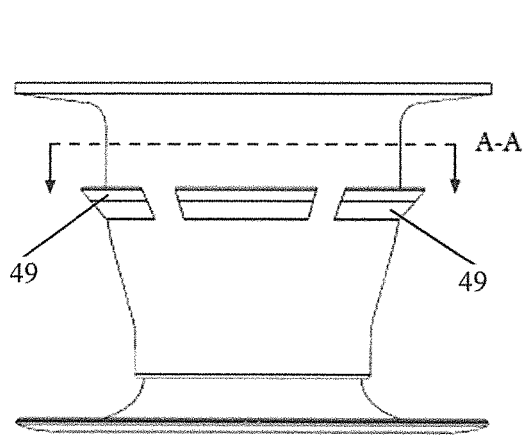
Figure 26:
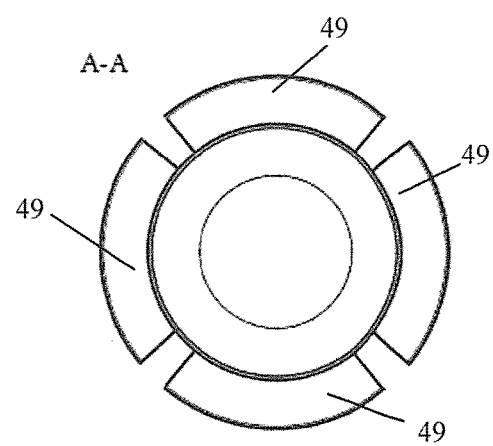

FIGS. 24 to 26 illustrate a plurality of spaced-apart separate barb segments 49 rather than one continuous element. The sectional view of FIG. 26 from above shows a configuration with four barb segments. The gaps between barb segments can vary in size, as can the number of individual barb segments.

Figure 27:
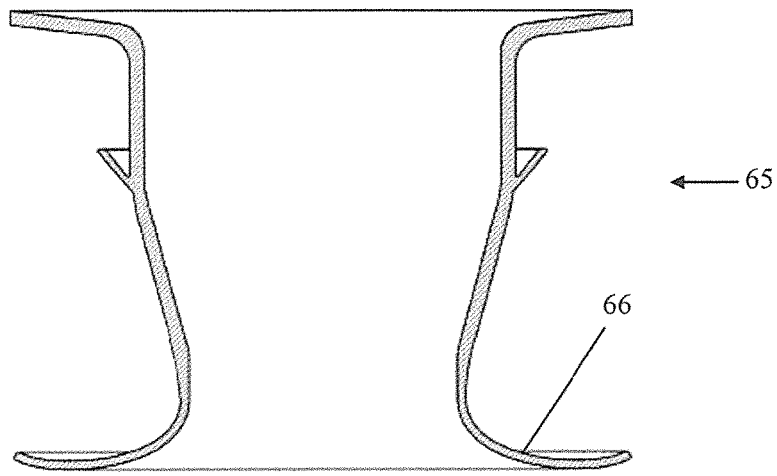
FIG. 27 is a cross sectional view of another guard with an integral distal skirt.

FIG. 27 illustrates another shield 65 having a skirt 66 at a distal part of shield which in this case is of the same material and part of the shield.

Figure 28:
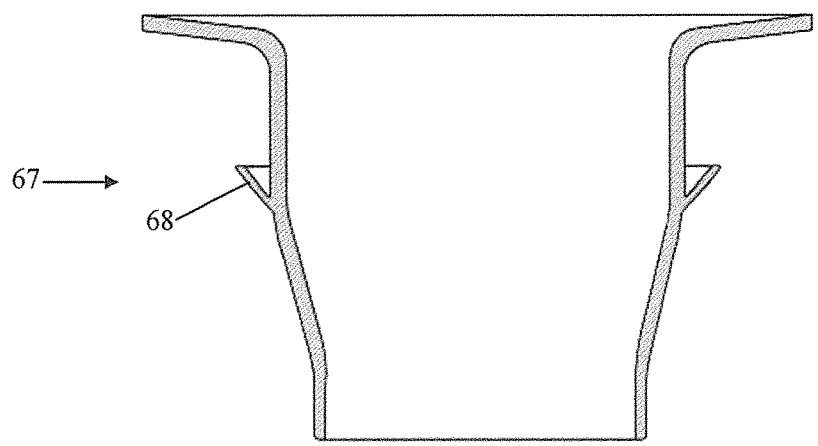
FIGS. 28 and 29 are cross sectional views of guards which do not have a distal skirt.

FIG. 28 illustrates a shield 67 with a thin walled barb 68. In this case the shield has no skirt feature at its distal end.

Figure 29:
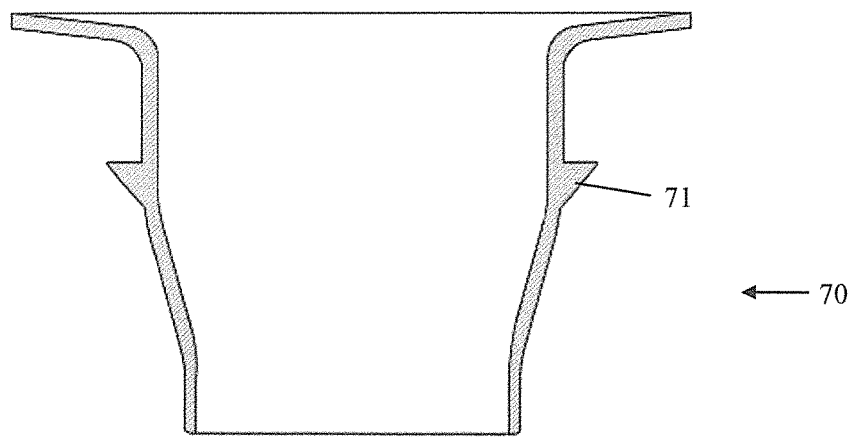
Figure 30:
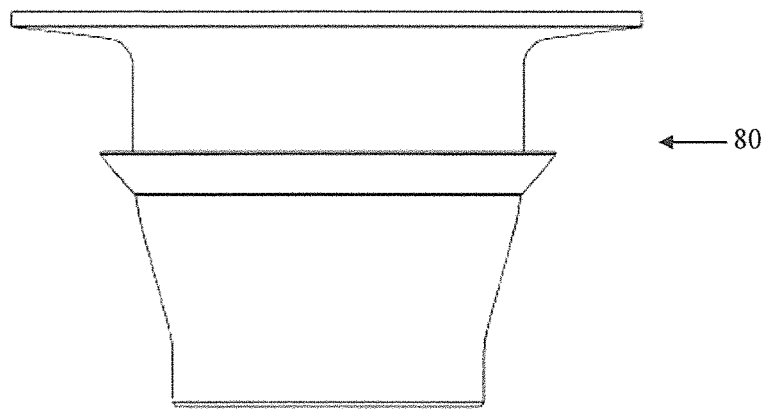
FIG. 30 illustrates another guard.
Figure 31:
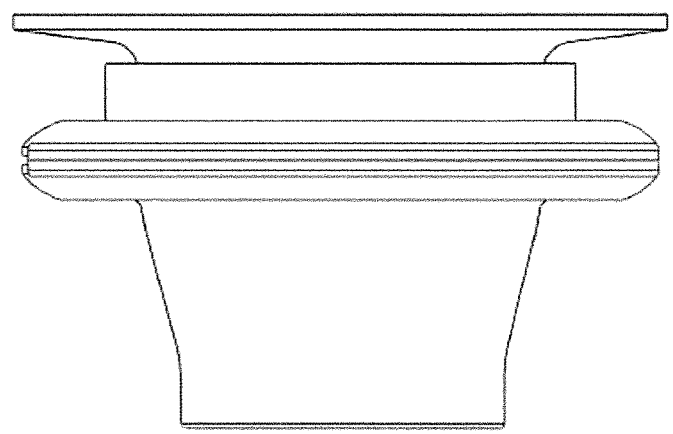
FIGS. 31 to 33 are views of the guard of FIG. 30 mounted to a base retractor.
Figure 32:
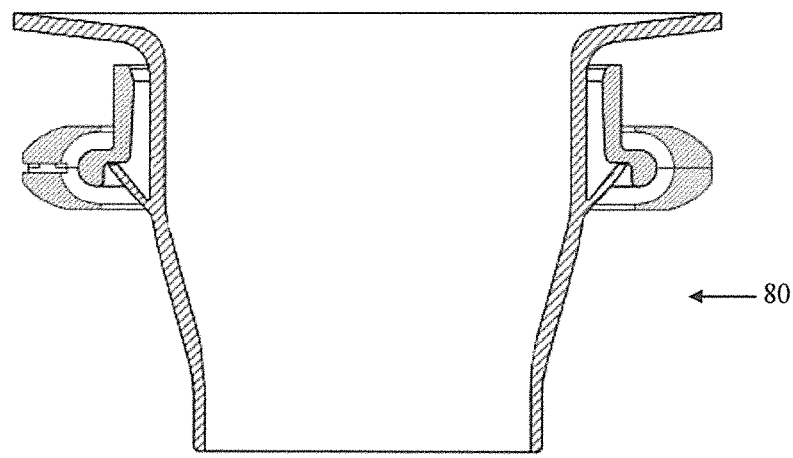

FIG. 29 illustrates a shield 70 with a solid or rigid barb 71. In this case the shield has no skirt feature at its distal end.

Figure 33:
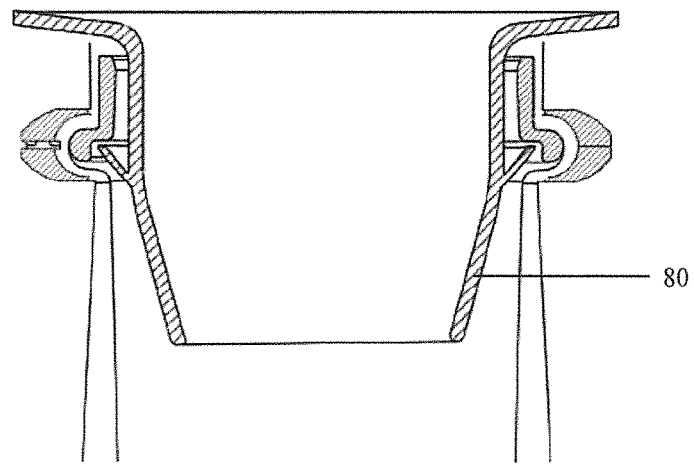

FIGS. 30 to 33 illustrate a snap-in shield 80 which does not have a distal skirt. FIG. 33 shows the locking of the shield to a base retractor.

Figure 34:
FIG. 34 is a cross sectional view of an inner proximal ring.
Figure 35:
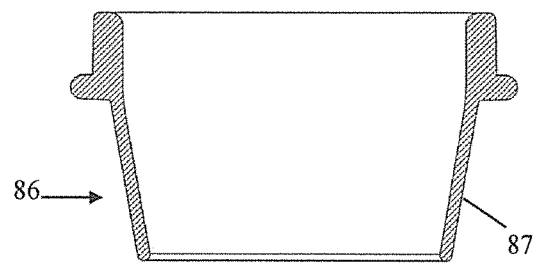
FIG. 35 is a cross sectional view of an inner proximal ring and retractor.

FIGS. 34 and 35 illustrate a modified inner proximal ring of a base retractor. FIG. 34 shows an inner proximal ring 85 and FIG. 35 illustrates a modified inner proximal ring 86 which incorporates a shield/guard 87 so that the morcellation shield may also function as a base retractor.

Figure 36:
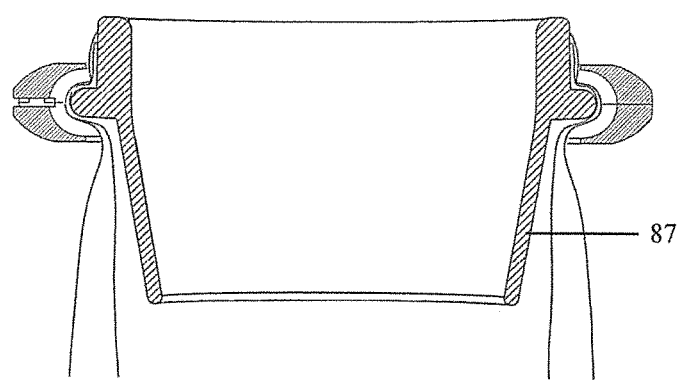
FIG. 36 is a cross sectional view of a base retractor.
Figure 37:
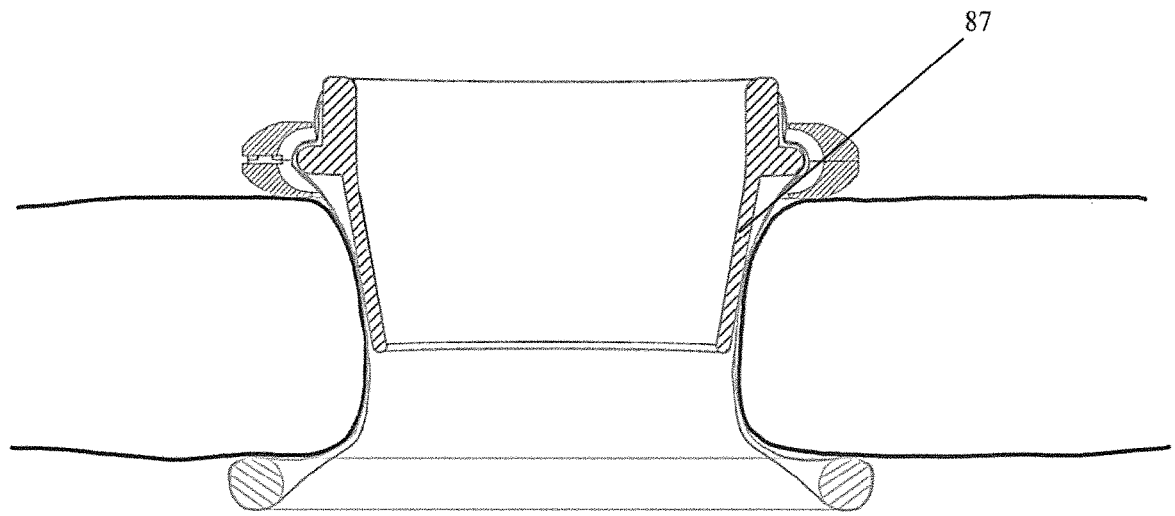
FIG. 37 is a cross sectional view of the base retractor of FIG. 36 in use.

FIG. 36 shows the assembled base retractor with the modified inner proximal ring 86 which acts as the shield for manual morcellation. FIG. 37 shows the shield in situ in an abdomen, retracted as normal and in place in the incision to act as protection.

Figure 38:
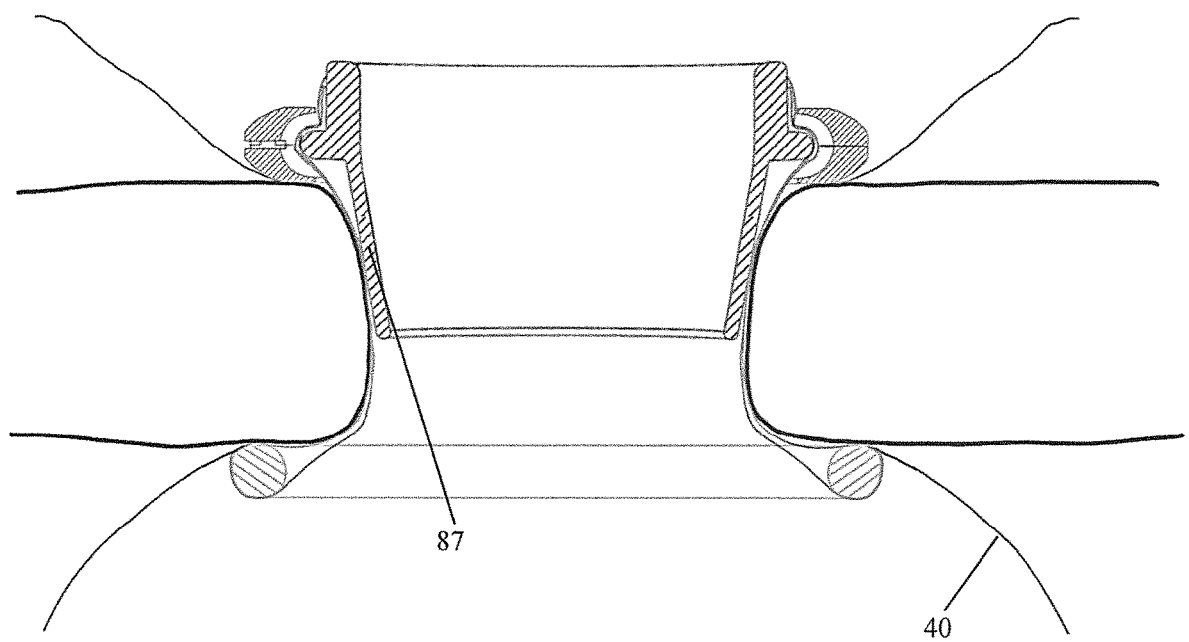
FIGS. 38 and 39 are cross sectional views of the base retractor of FIGS. 36 and 37 with a tissue containment bag in place.
Figure 39:
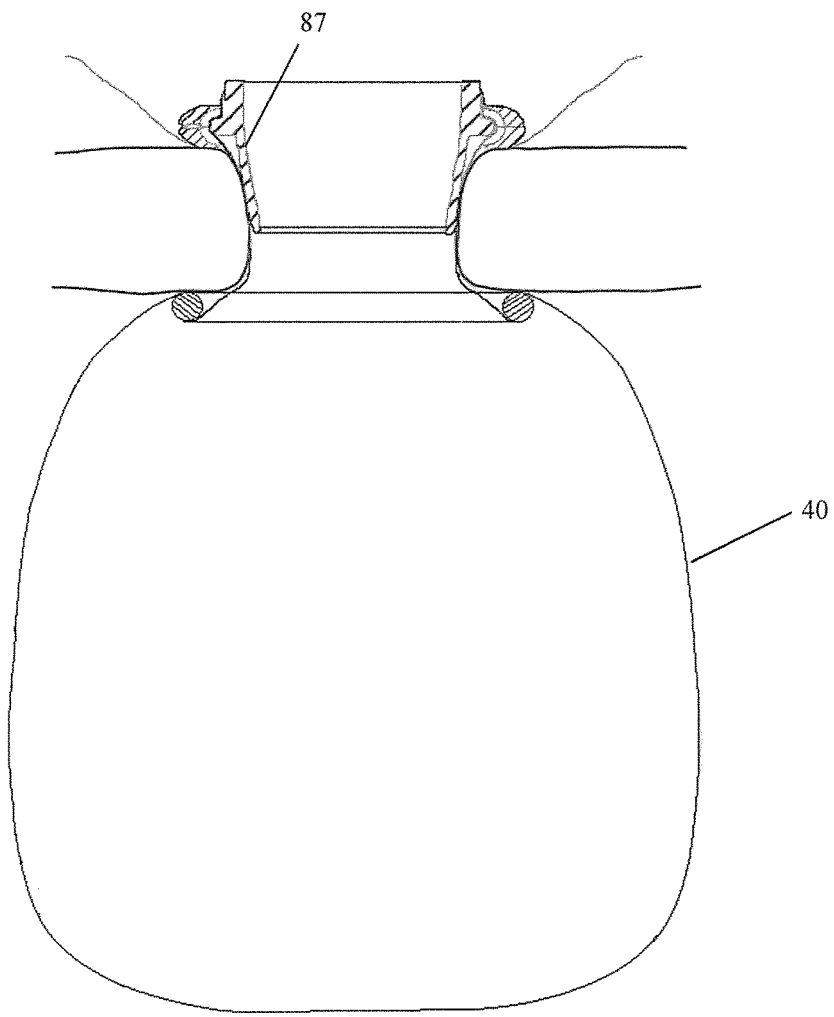

FIGS. 38 and 39 are images that include the tissue containment bag 40 and illustrates the rigid modified guard would protect the vulnerable upper part of the incision and bag material from any scalpel blade introduced. In this case the tissue containment bag 40 is located outside of the retractor guard. In FIG. 39, it can be seen how the distal ring component of the base retractor shield serves to push the material of the tissue containment bag 40 clear from the distal portion of the incision.

Figure 40:
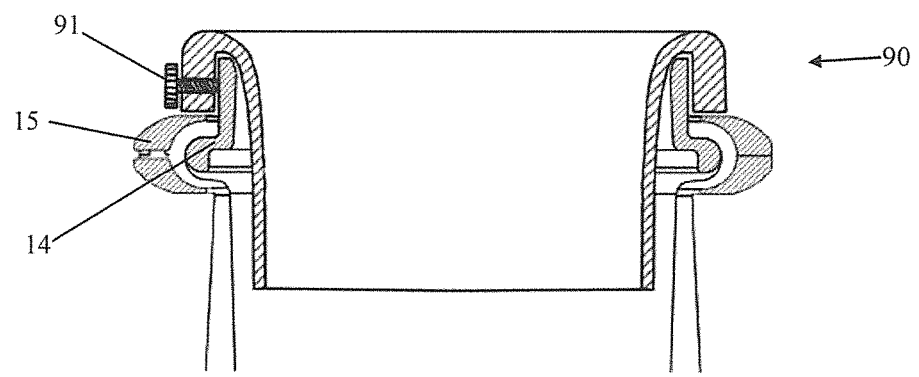
FIG. 40 is a cross sectional view of a guard mounted to a base retractor.

FIG. 40 illustrates a guard 90, an auxiliary component which is inserted through the base retractor opening and locked in place via a grub screw 91, or similar clamping mechanism. In this example it is locked to the inner proximal ring 14, but it could also be locked to the outer proximal ring 15.

Figure 41:
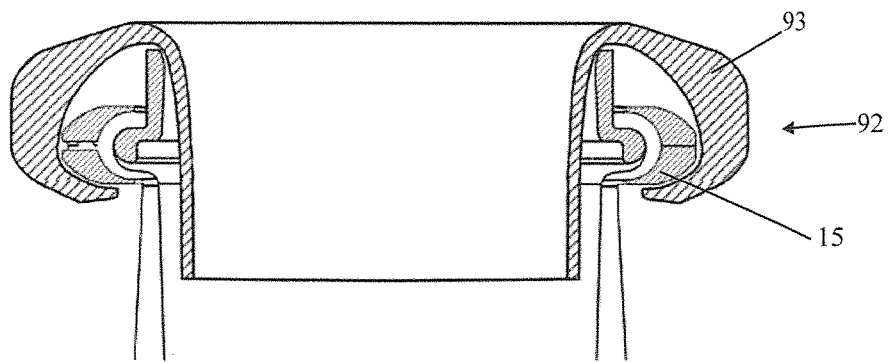
FIG. 41 is a cross sectional view of another guard mounted to a base retractor.

FIG. 41 illustrates a guard 92, an auxiliary component which is inserted through the base retractor opening and locked in place via a snap fit 93 over the outer proximal ring 15. The larger outer wings of the shield would displace slightly to push over the outer proximal ring and to snap to the underside in order to secure the guard. The guard can later be pried off using a lever or handle or by gripping and pulling one side only.

FIGS. 42 to 45 illustrate another means of attachment to the inner proximal ring. In this case, the guard 95 comprises a flexible but cut resistant material which serves as a malleable and dynamic manual morcellation guard without disturbing the continuity of a standard base retractor. The flexible guard material 95 can be made of a single material or multiple binded or interwoven materials in which the prevailing property is to resist cutting from a scalpel blade during manual morcellation. The flexible sheath guard material 95 is bonded to the inner proximal ring 14 in this embodiment and lies inside, and independent of, the retractor sleeve. The shield may be provided in a number of lengths or can be provided in extra length in order to be trimmed to suitable length by the surgeon.

Figure 44:
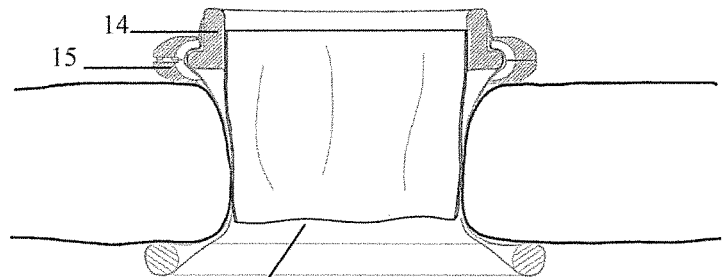
Figure 45:
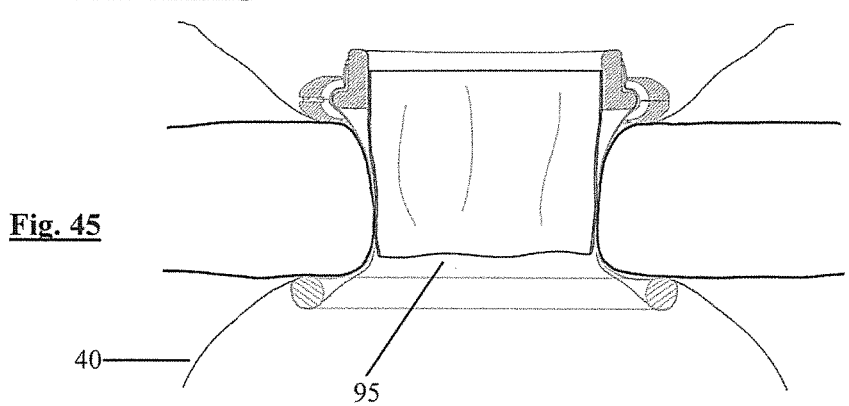

FIGS. 44 and 45 show the sheath guard 95 in situ in the incision and within the tissue containment bag 40. Having a flexible and possibly stretchy sheath guard 95 allows for varying size incision sizes as well as varying abdomen thicknesses. The sheath guard can be configured in many different ways.

Figures 42, 43:
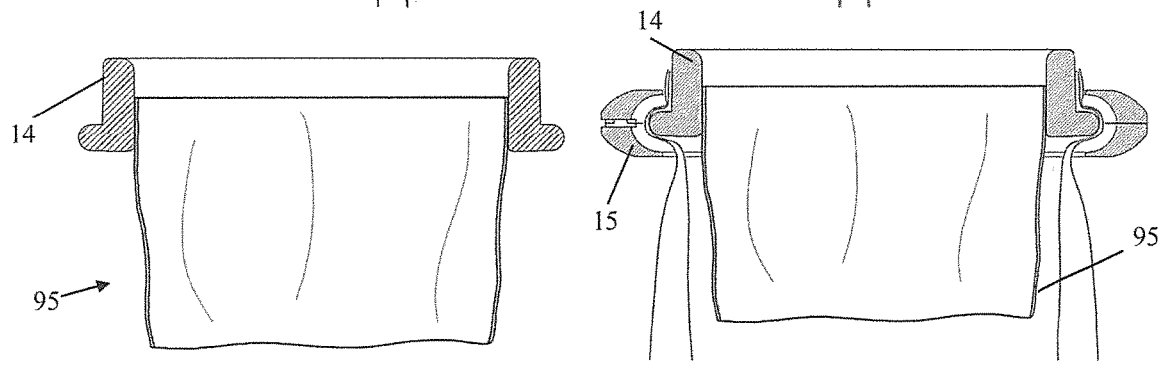
FIGS. 42 to 45 are cross sectional views of a sheath guard according to the invention.

FIGS. 43 to 45 illustrate the guard attached only to the inner proximal ring and nowhere else to provide a particularly simple construction.

Figure 46:
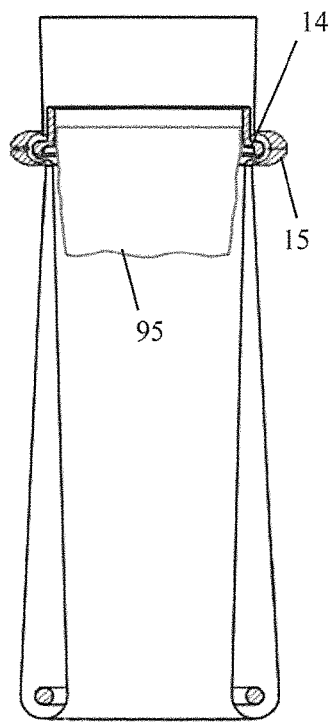
FIGS. 46 to 47 illustrate mounting of a sheath guard to an inner proximal ring.
Figure 47:
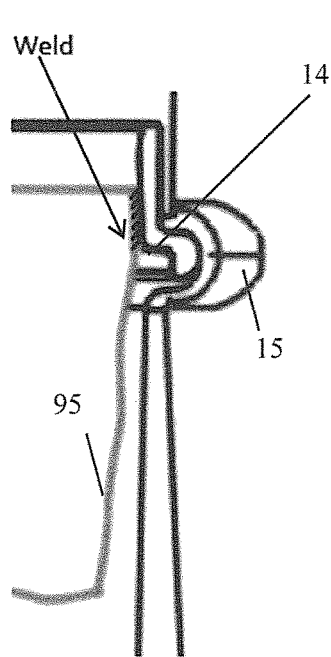

Referring to FIGS. 46 and 47, the sheath guard material 95 may be welded to the solid inner proximal member via a ring weld as shown or intermittent spot welds. The weld is not limited to the inner surface of the inner proximal ring.

Figure 48:
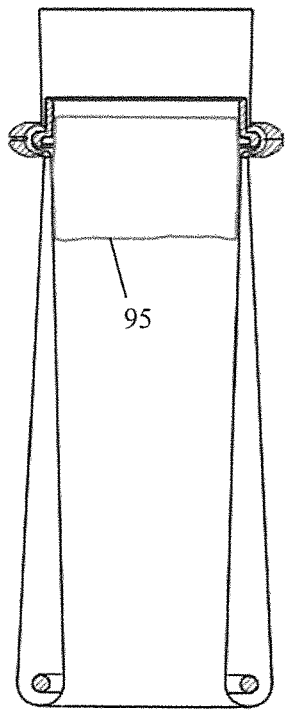
FIGS. 48 to 49 illustrate mounting of a sheath guard to an inner proximal ring and to a sleeve of a retractor.
Figure 49:
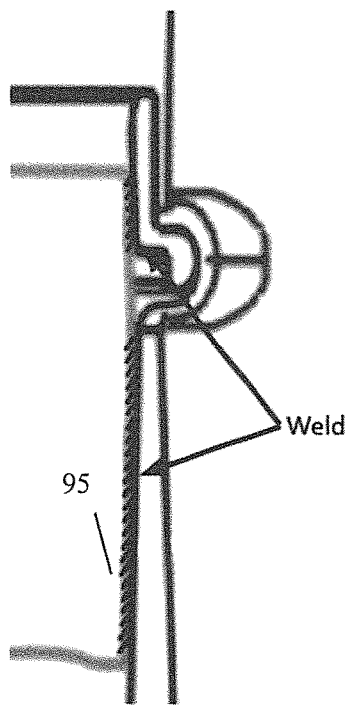

Alternatively, as illustrated in FIGS. 48 and 49, the guard 95 may be attached to the inner proximal ring and to the base retractor sleeve in spots or across its entire length and surface area. The sheath guard material could be welded to both the rigid inner proximal ring and flexible sleeve. The sheath guard material could also be only welded to the sleeve and not to the inner proximal ring. The sheath guard material may only commence below or around the inner proximal ring.

Referring to FIGS. 50 and 51, the guard 95 may be bonded/welded to both inner proximal ring and the retractor sleeve. The guard is long in this instance, and the retraction of the incision would cause the sheath guard material to reach the distal end of the incision and extend around the distal ring. This image shows that the sheath guard material may also be bonded to the underside of the inner proximal ring. The guard 95 may only be welded to the flexible sleeve. Cases where a sheath guard 95 is only welded in the upper portion, the extra length of sheath 95 that is not directly welded could be trimmable by surgeon to facilitate different lengths for use.

FIG. 52 shows a base retractor in which the entire retractor sleeve 97 is made from a sheath guard material.

Figures 53, 54:
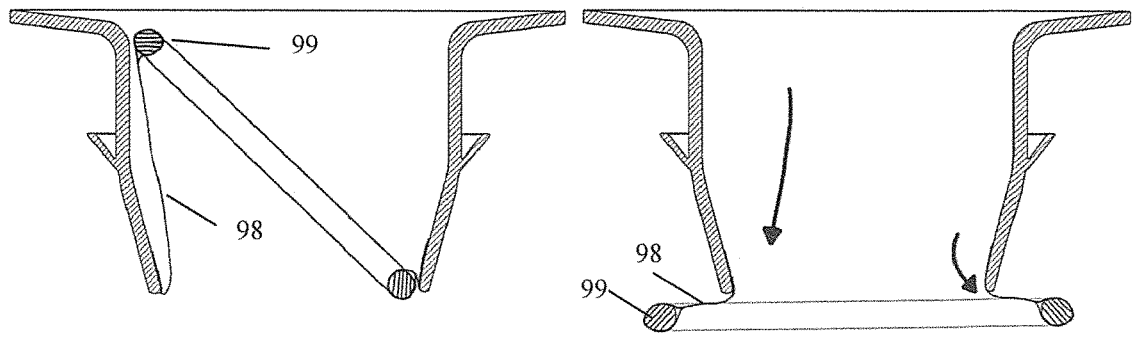
FIGS. 53 and 54 illustrate a guard with a distal sleeve portion.

FIGS. 53 and 54 includes a snap in shield, but instead of a rigid/semi-rigid skirt feature at the bottom, it has a sleeve portion 98 attached to the bottom of the shield, which in turn connects to a distal ring 99. The sleeve material 98 may be elasticated but would at least be highly flexible to allow the distal ring 99 to be stored within the main body during insertion as shown. The ring 99 would be popped out following insertion in order to protect the distal part of an incision and/or lock and to assist in securing the guard in place by anchoring.

Figures 55, 56:
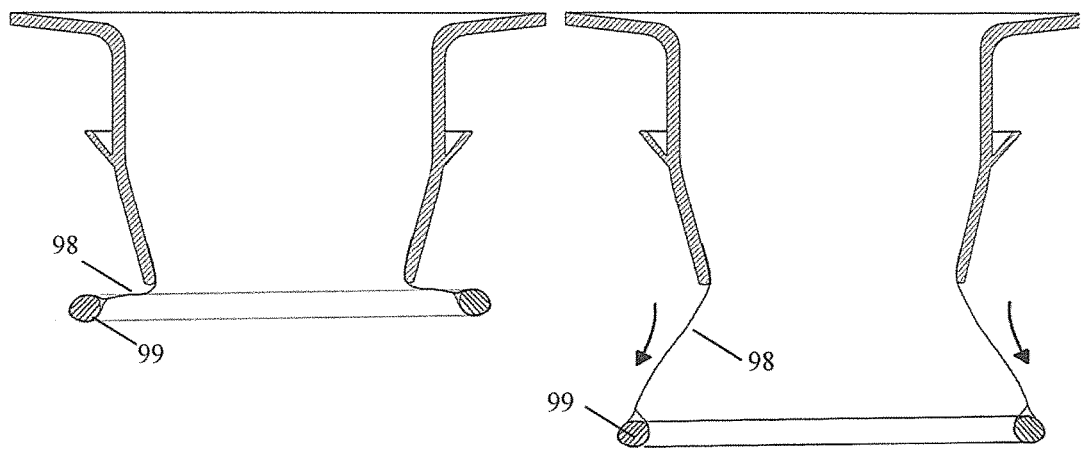
FIGS. 55 and 56 illustrate another guard with a distal sleeve portion.

FIGS. 55 and 56 illustrate a stretchy/elastic distal sleeve portion 98 which would facilitate varying abdomen thicknesses.

Figures 57, 58:
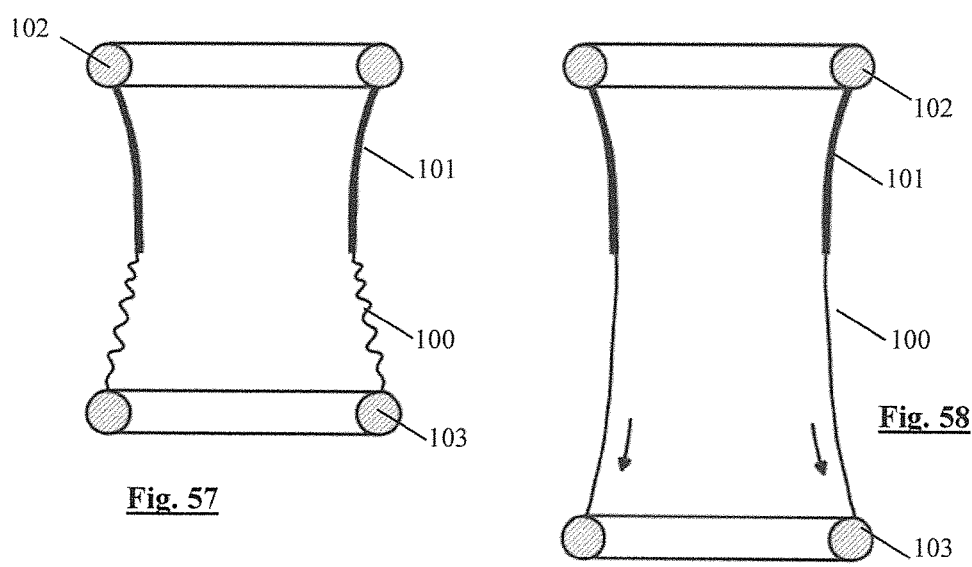
FIGS. 57 and 58 are images of a guard retractor with a distal sleeve section which is more flexible than a proximal sleeve section.

FIGS. 57 and 58 illustrate a guard retractor in which a lower portion comprises a flexible material 100 and an upper part 101 comprises a rigid, semi-rigid or flexible cut resistant portion and attached at either end to anchor rings 102, 103.

Figure 59:
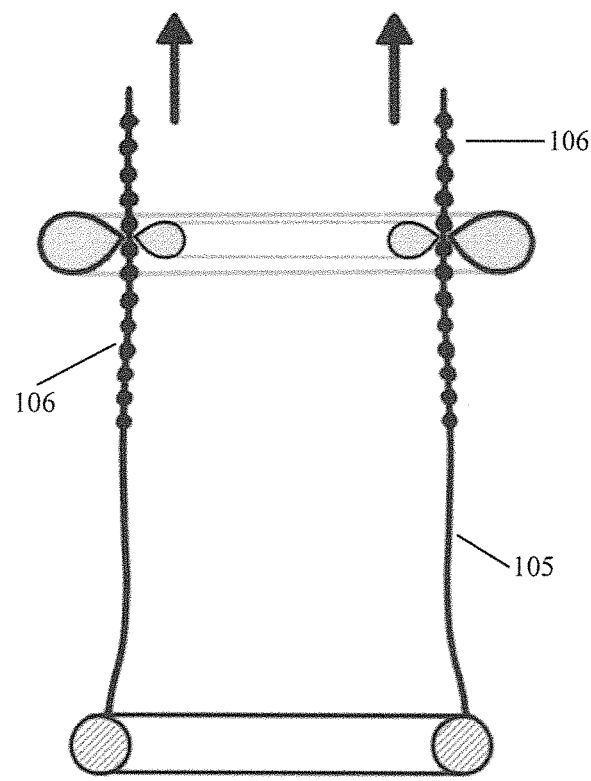
FIG. 59 is a cross sectional view of another guard retractor having a racket locking system.

FIG. 59 illustrates a single sleeve retractor 105 in which the locking of the retractor is achieved via a ratcheting system 106 built into the sleeve. The sleeve may incorporate shield material to protect against manual morcellation.

Figure 60:
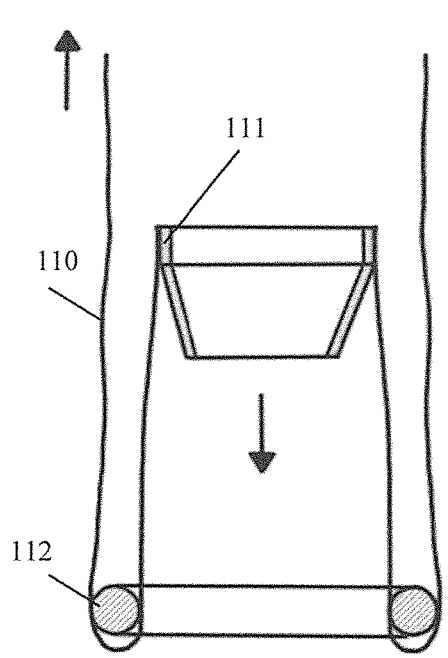
FIGS. 60 and 61 illustrate the operation of a guard and retractor sleeve.
Figure 61:
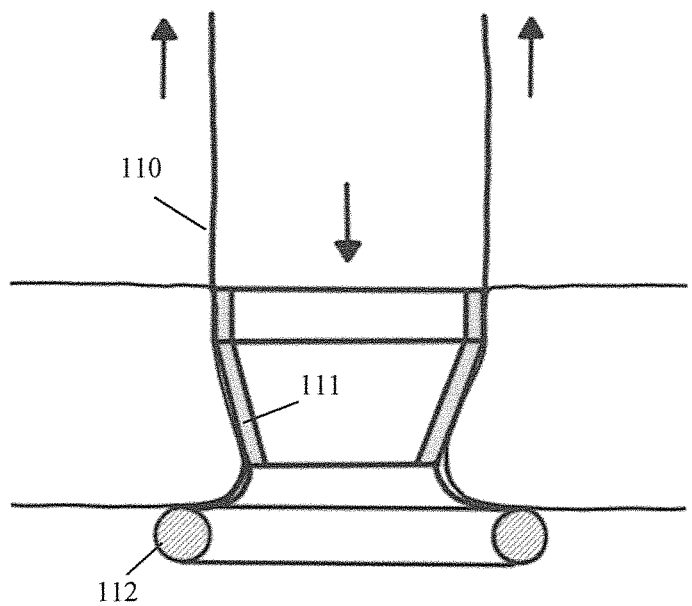

FIGS. 60 and 61 illustrate the attachment of a sleeve 110 to the rigid or semi-rigid guard component 111 around a single ring 112 in a pulley type arrangement. The distal ring 112 is inserted into the abdomen and anchored, then the sleeve 110 is pulled up in order to simultaneously pull the guard 111 into the incision.

Figure 62:
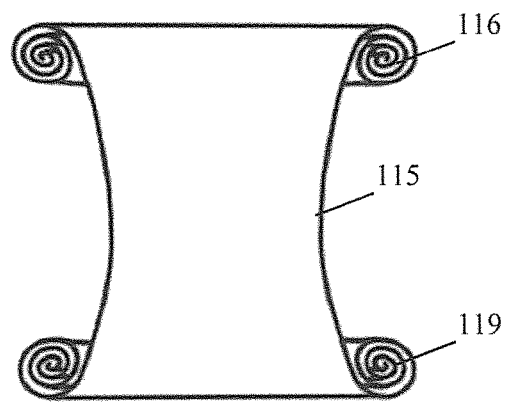
FIGS. 62 and 63 illustrate another guard retractor.
Figure 63:
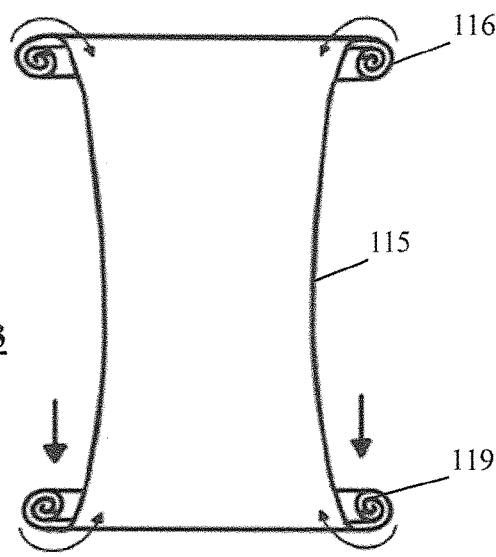
Figure 64:
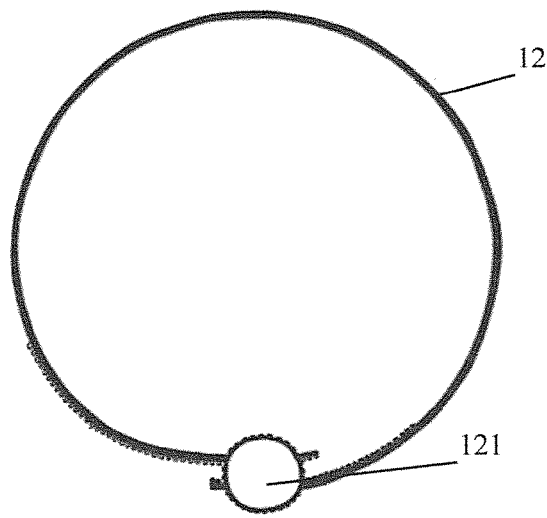
FIGS. 64 to 68 illustrate a guard with a variable diameter.
Figure 65:
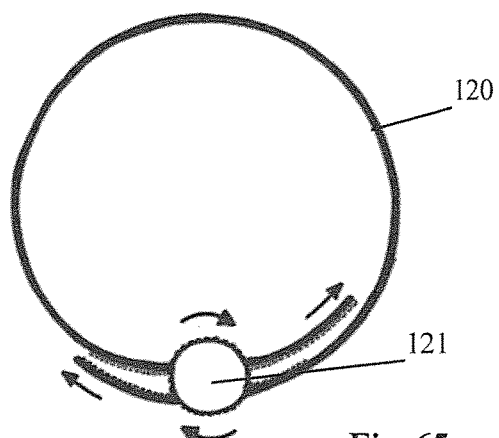
Figure 66:
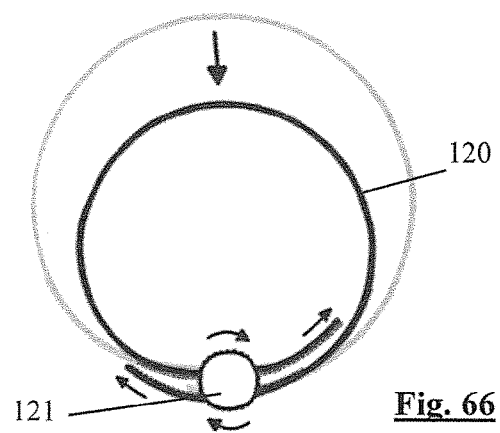

FIGS. 62 and 63 illustrate a retractor shield in which the sleeve 115 has rolled up portions 116,119 at either end that are biased to roll up like a sprung metal. The sleeve is of a rigid/semi-rigid material and may be forced to unroll to fit larger incisions then the roll up bias occurs and tightens the guard within the incision.

FIGS. 64 to 68 illustrate a retractor shield 120 in which the guard diameter in a rigid/semi-rigid guard is variable, for example by turning of a knob/screw 121 that brings each end of the guard further away from the other. It does this in a similar way to that of a hose clip. The two ends of the guard material have a toothed profile in order to engage fixedly with the screw 121 for controlling the diameter.

Figure 67:
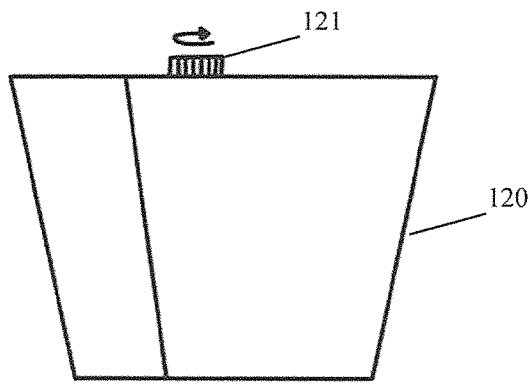
Figure 68:
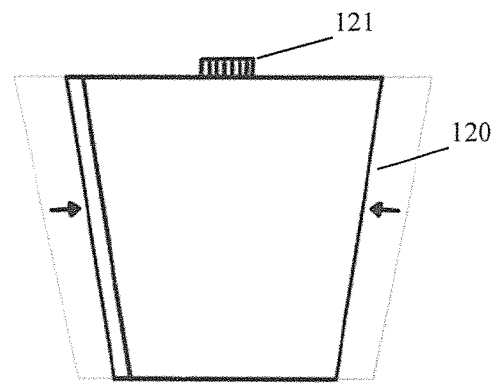
Figure 69:
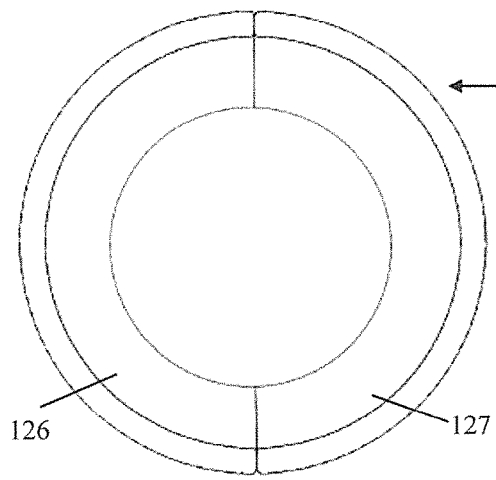
FIGS. 69 to 72 illustrate another variable diameter guard.

FIGS. 67 and 68 show the constriction of the overall guard 120 to a smaller incision size by turning the screw 121 at the top.

Figure 71:
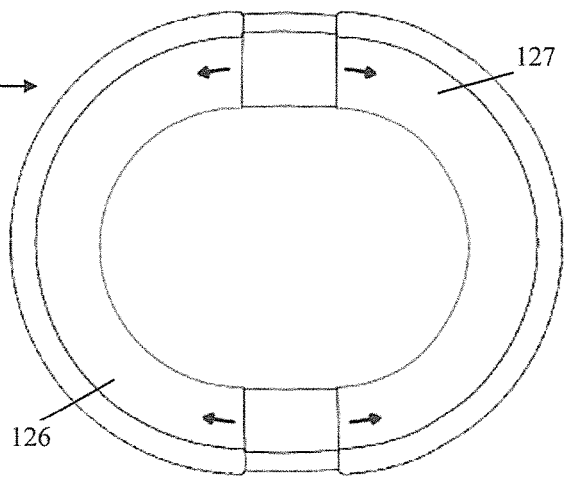
Figure 70:
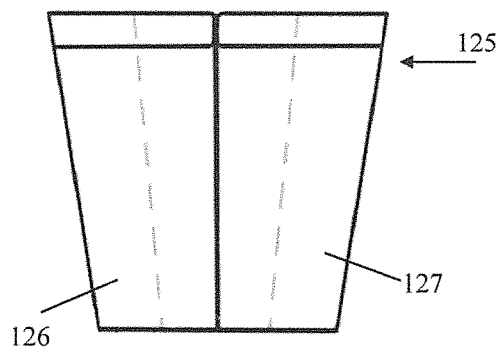
Figure 72:
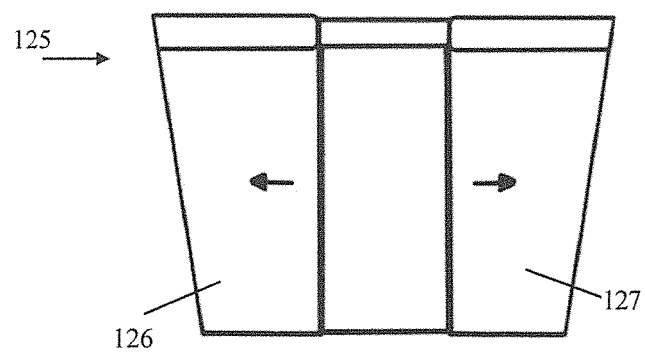

FIGS. 69 to 72 illustrate another variable diameter guard 125 in which the guard is enlarged by extending two portions 126, 127 away from each other via a third and fourth internal member in a telescopic manner. The two portions 126, 127 can extend and lock at varying sizes. FIGS. 71 and 72 show the guard 125 from the side.

Figure 73:
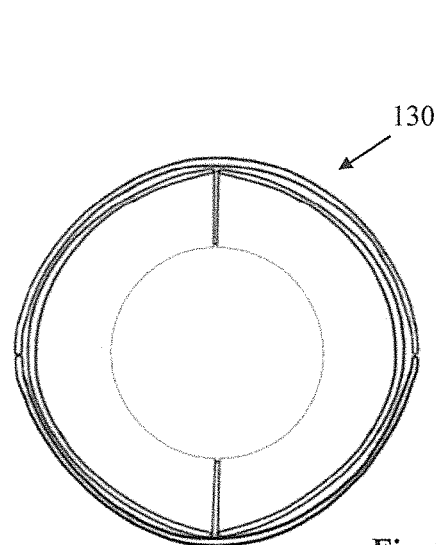
FIGS. 73 and 74 are images of a further variable diameter guard.
Figure 74:
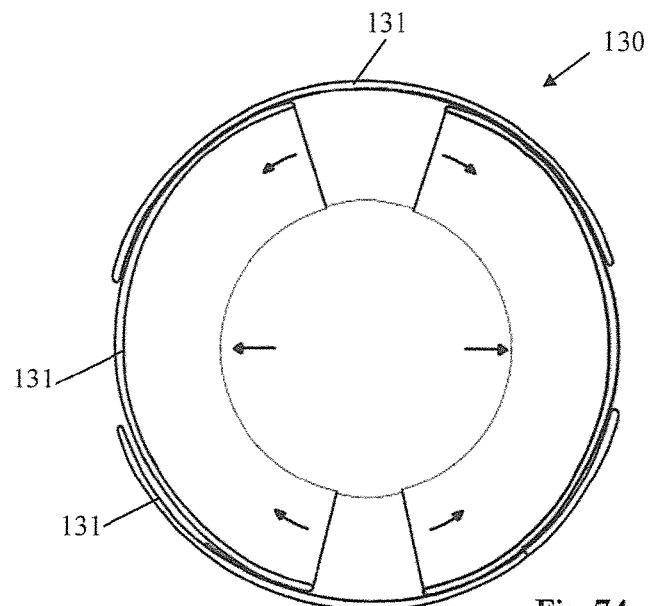

FIGS. 73 and 74 illustrate another variable diameter guard 130 in which the guard exhibits an armadillo type design comprising a number of inter-slidable sheets 131 of guard material (rigid/semi-rigid) while slide over one another to fit any size incision. Each plate/sheet 131 can be locked to its surrounding sheets 131 when correct size is achieved.

FIGS. 75 to 80 illustrate another embodiment in which a guard 140 comprises multiple plates 141 (in this case four but not limited to four), rather than sliding over one another to create an overlap. The plates include one or more plates that slide up and down (two in this example but not limited to two). The movable plate 141 is tapered as shown, whereby varying the height of the movable plate 141 changes the diameter of the guard 140. In this way the guard can adapt to varying incision diameters.

Figure 75:
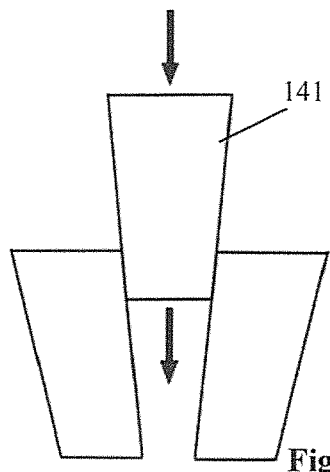
FIGS. 75 to 80 are images of a guard which comprises parts which are movable relative to one another.
Figure 76:
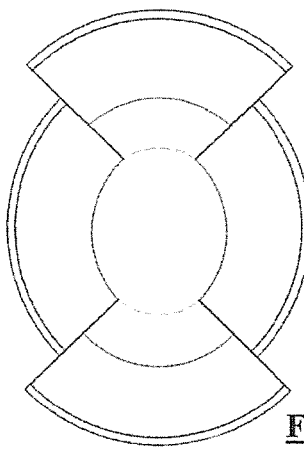

Referring to FIGS. 75 and 76, close to the moving plates maximum height the non-sliding plates can be forced inwards by an external inward pressure, resulting in a small opening.

Figure 77:
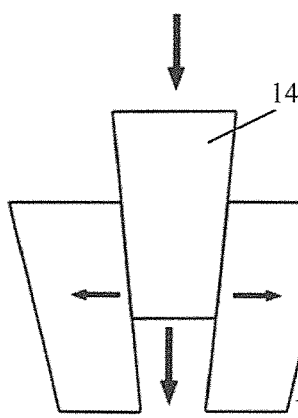
Figure 78:
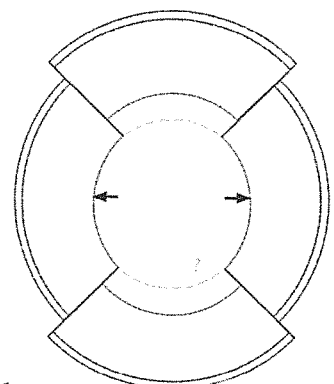

Referring to FIGS. 77 and 78 as the moving plates are depressed downwards, a force is exerted on the non-sliding plates laterally, forcing the overall opening to grow larger in diameter.

Figure 79:
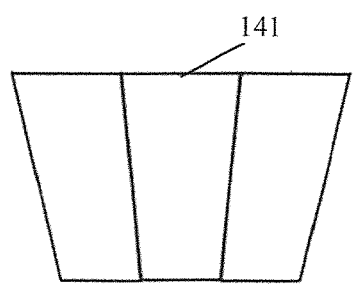
Figure 80:
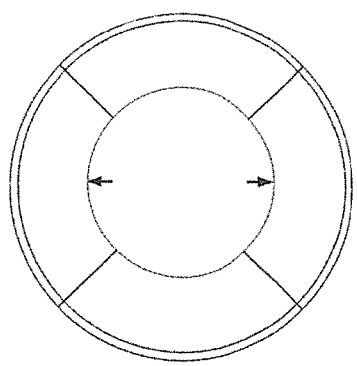
Figure 81:
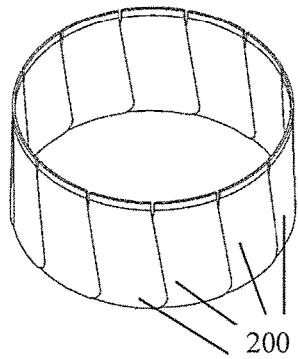
FIG. 81 is an isometric view of another guard according to the invention.
Figure 82:
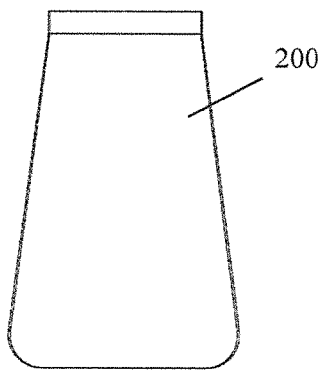
FIG. 82 is an enlarged view of one element of the guard of FIG. 81.
Figure 83:
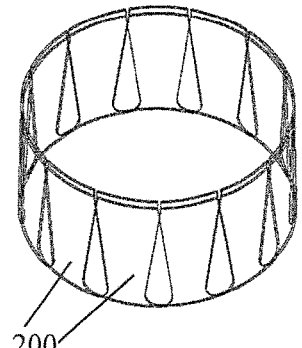
FIGS. 83 to 86 are views illustrating the overlap between elements of the guard.

FIGS. 79 and 80 illustrate fully depressing the slidable plates results in the maximum size opening.

The moving plates may or may not be the same height as the non-moving plates and may or may not be made from the same material. The moving plates may be locked in place using a ratcheting system or snap feature or other to fix the opening size at desired size. By varying the taper of the plates the difference between small and large opening sizes can be adjusted.

Referring to FIGS. 81 to 103 the guard in this case comprises a series of petals 200 circumferentially arranged in an overlapped manner. The guard may be mounted to or located within a base retractor.

The overlapped petals 200 are arranged in an overlapped fashion to allow either petal 200 to slide over its adjacent petal 200 in order to accommodate different sized incisions when met with a circumferential force from the outside from the incision.

There may be any number of petals 200. The petals 200 may be a range of shapes sizes and lengths. An array of petals can be stamped as one piece of material (referred to as a blank) or as individual petals.

The petals may be of any suitable material such as a semi-rigid plastic or a cut resistant flexible fabric material, rubber or the like.

Figure 84:
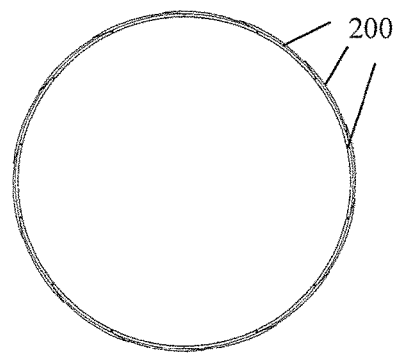

FIG. 84 shows petals 200 isolated from any assembly into a base retractor to help illustrate petal behaviour. FIG. 84 shows a straight resting position of petals 200 with a small starting overlap.

Figure 85:
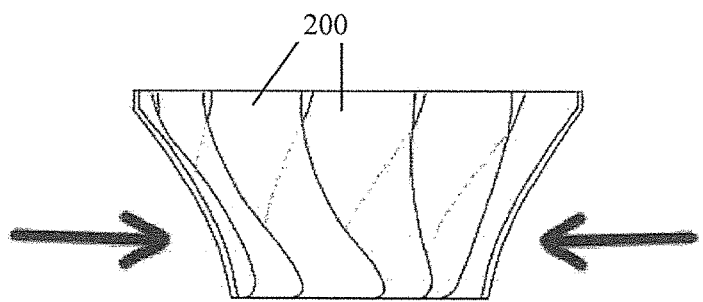
Figure 86:
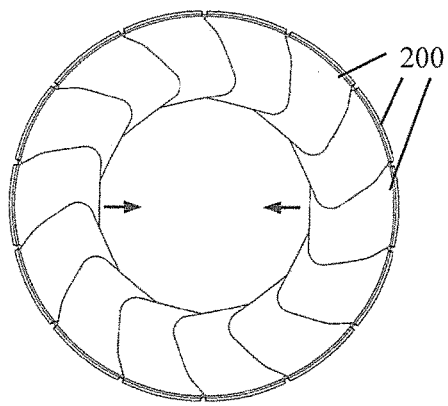

Referring to FIG. 85, when a force is placed on the outside of the petals 200 (e.g. by a circumferential base retractor sleeve and/or incision) the overlap between each petal 200 is increased to create a smaller diameter to fit smaller incisions while minimising encroachment in the incision. The petals 200 automatically vary to the size of the incision rather than having to be deliberately resized to fit.

Figure 87:
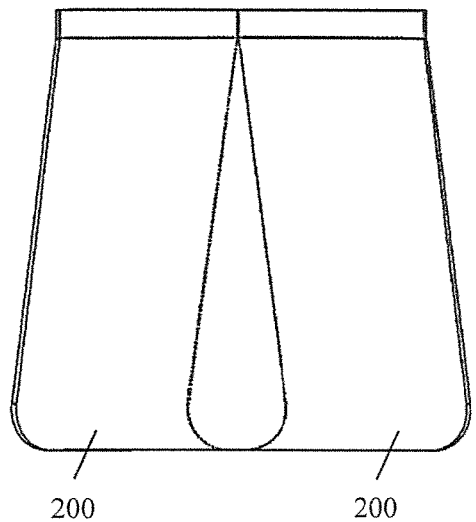
FIGS. 87 and 88 illustrate overlap between two petals.
Figure 88:
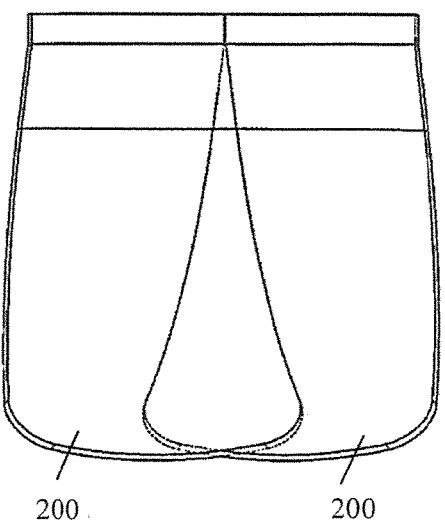

FIGS. 87 and 88 show a two petal 200 example section. FIG. 87 shows the original resting position with resting overlap and FIG. 88 shows an increasing overlap to accommodate diameter change.

Figure 89:
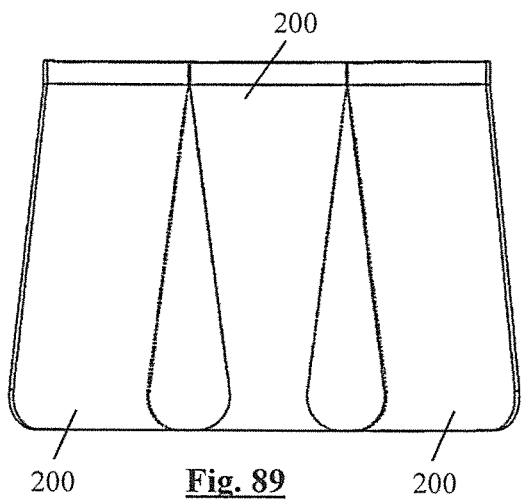
FIGS. 89 and 90 illustrate overlap between three petals.
Figure 90:
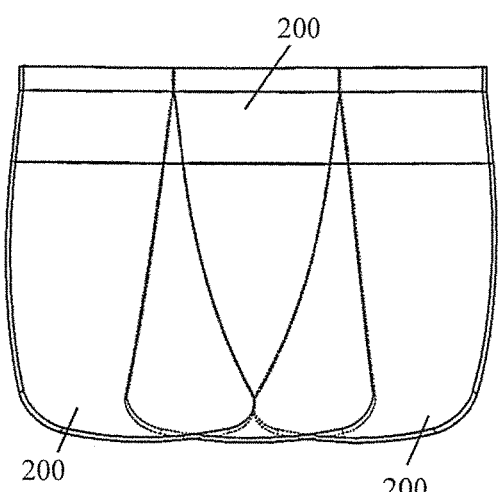

FIGS. 89 and 90 show a three petal 200 example section. FIG. 89 shows the original resting position with resting overlap and FIG. 90 shows an increasing overlap to accommodate diameter change.

By using multiple overlapped petals 200, the total overlap is spread across a multitude of overlap areas and thereby the total diameter change can be achieved with minimal effort.

The petal device provides a multitude of overlapped areas rather than one means of overlap (coiling). The petal device can also function as a full retractor system. The device may be configured to reach a minimum at the midpoint/narrowest point in the incision. The device accommodates full range of abdomen thickness. There is minimal encroachment into the cutting working diameter because the sleeve pushes the guard flush to the incision.

Figure 91:
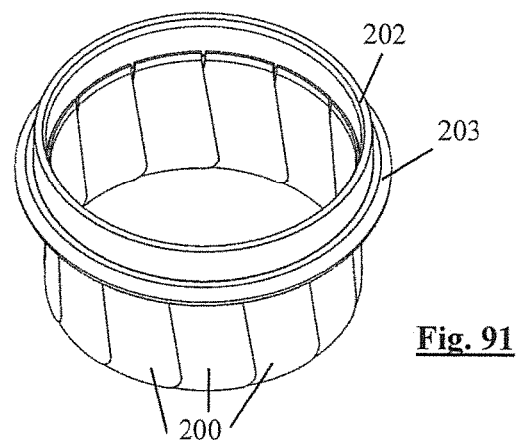
FIG. 91 is an isometric view of a guard comprising a ring to which a plurality of guard elements are mounted.
Figure 92:
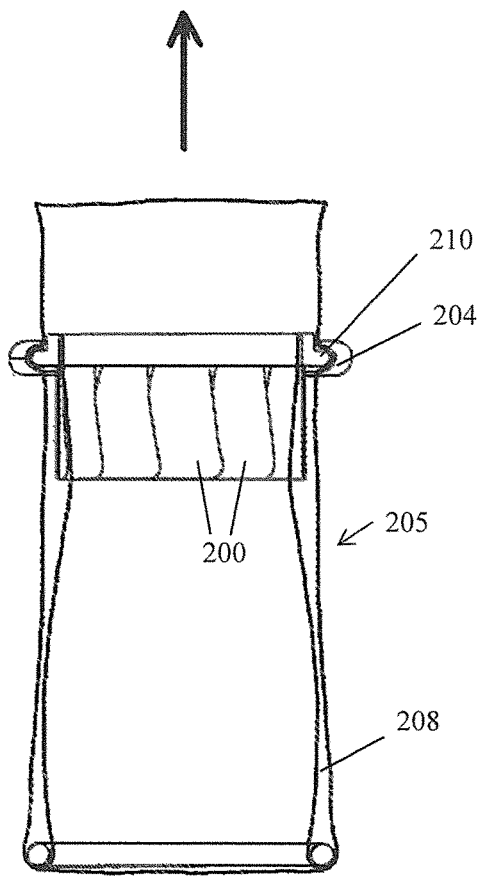
FIGS. 92 to 95 are views of the guard of FIG. 91 and a base retractor.

Referring in particular to FIG. 91, the petals 200 may be mounted to a ring 202. In some cases the ring 202 may have mounting features 203 for mounting to an outer proximal ring 204 of a base retractor 205. In some cases the inner ring 202 may be mounted to or integral with an inner proximal ring 210 of the base retractor.

Figure 93:
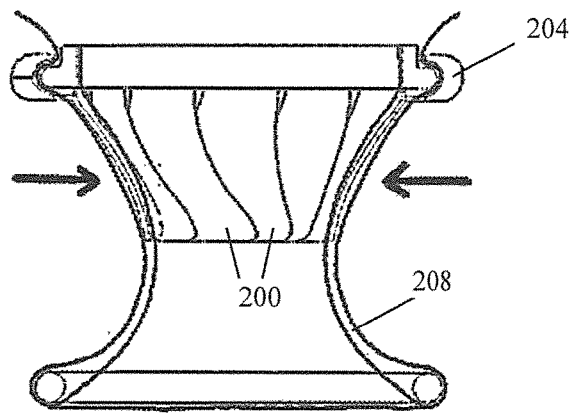
Figure 94:
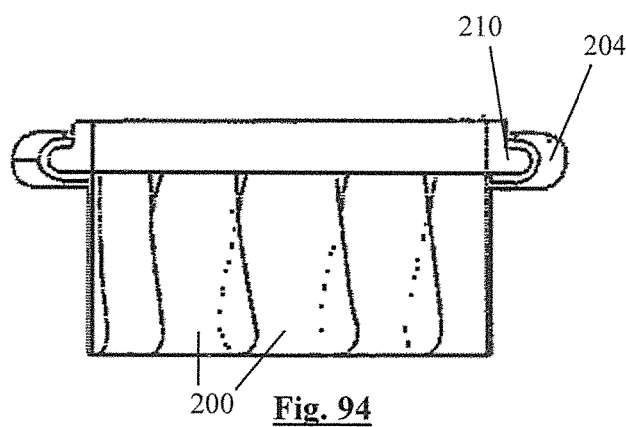
Figure 95:
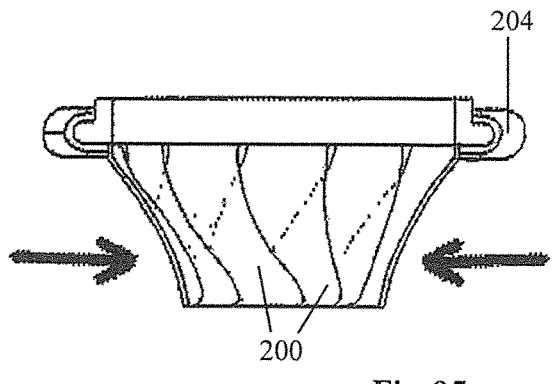

Referring in particular to FIGS. 93 to 95, when placed into a base retractor 205 the retractor sleeve resizes the petal guard automatically when retracting the incision. The sleeve and the incision 208 push circumferentially on the petals 200 and increase the overlap and resize the guard passively, with deliberate steps to resize.

As illustrated in FIGS. 96 and 97, the petals or guard plates 200 can be fixed in position between the two sleeves of the retracting sleeve 208 or inside the inner sleeve of a double sleeve retractor.

FIG. 97 shows the assembly of the guard to a retractor 205. Petals 200 are attached to inner proximal ring 210. In this case the retractor sleeve is omitted for clarity.

In this case, the petals 200 are configured and sized to extend from the inner proximal ring 210 to a minimum of the narrowest point of the incision.

Referring to FIG. 98, the base retractor 205 with the petal guard can be inserted into a containment bag and retracted as normal. The guard passively adjusts with retraction via the overlapping petals 200.

Figure 99:
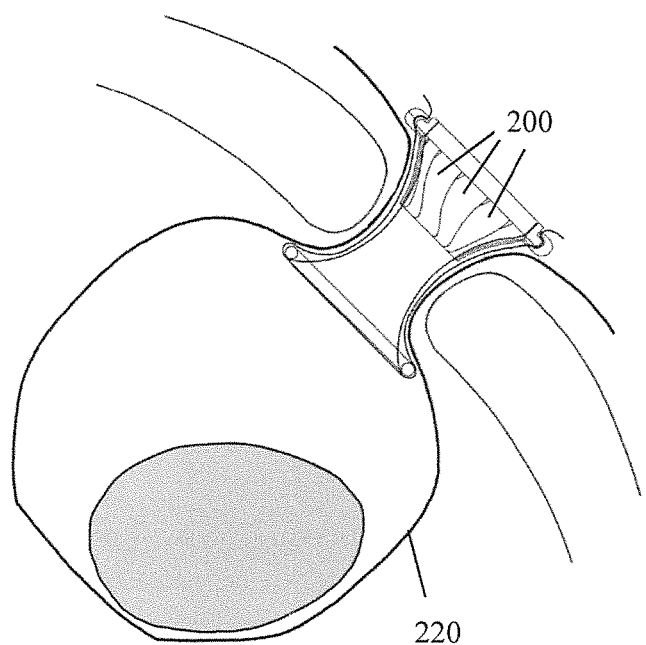
FIG. 99 shows the guard and retractor base.

FIG. 99 illustrates the petal guard adjusting to an incision within the retracting system by increasing the amount of overlap between adjacent petals 200, thus reducing to the diameter size of the incision.

Figure 100:
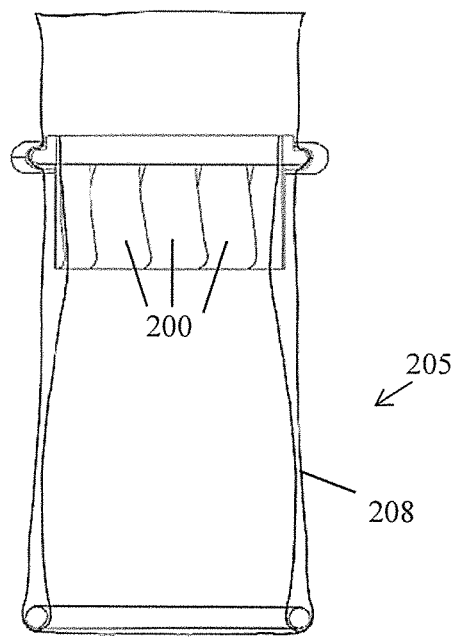
FIGS. 100 and 101 illustrates the guard in use with a retractor.
Figure 101:
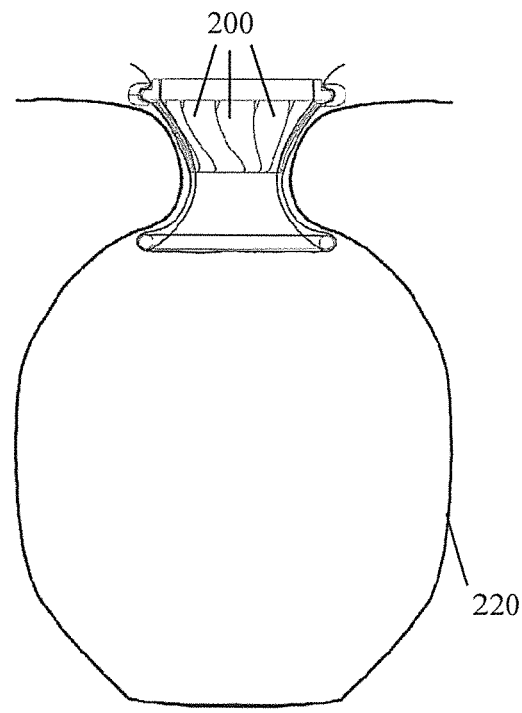

Referring to FIGS. 100 and 101 the petal guard is illustrated adjusting to an incision within the retracting system.

Figure 102:
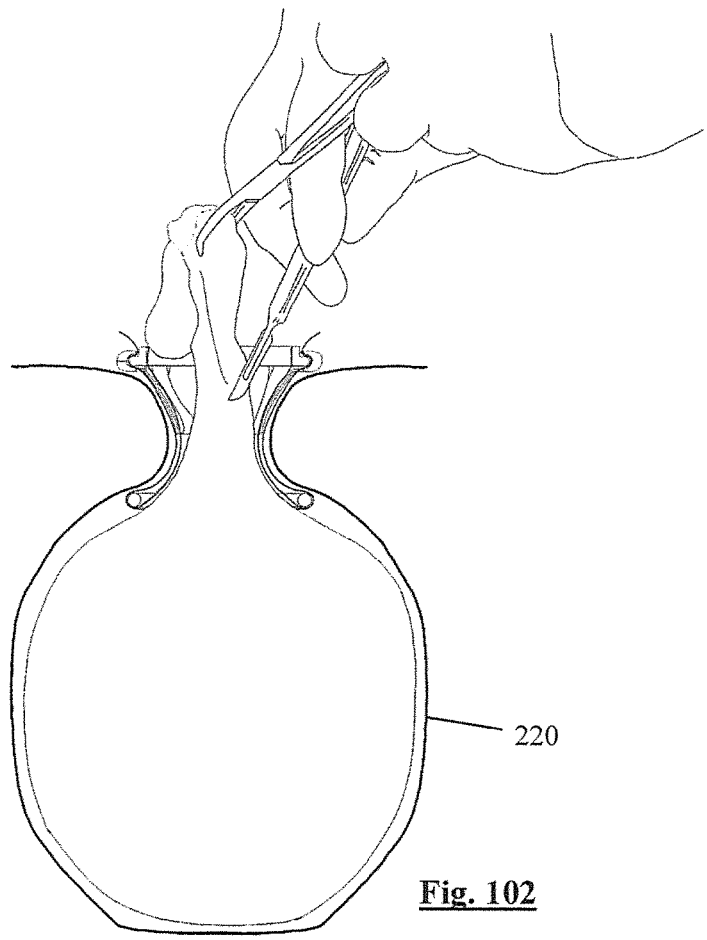
FIG. 102 is a diagram illustrating the guard in use protecting a containment bag during manual morcellation.

FIG. 102 shows the protection of any containment bag 220 from a manual morcellation procedure. The guard material reaches the narrowest part of the incision and is pushed out of the way by the retracting sleeve 208 during retraction. The distal end of the retractor serves to remove any excess bag material away from the incision and away from the scalpel during manual morcellation.

The petal guard ensures overlap is maintained to ensure fully circumferential protection.

Figure 103:
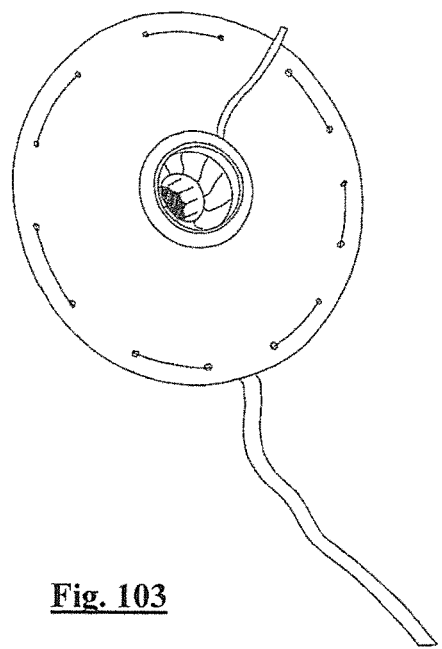
FIG. 103 is a view from above illustrating the vulnerable upper part of an incision.

FIG. 103 is a view from above of the setup within a containment bag whereby the guard is protecting the vulnerable upper part of the incision and the incision is maximized in size by the retraction elements of the device.

The invention provides a tissue guard which comprises a plurality of petals. The petals are at least partially overlapped. At least some of the petals are movable from a resting configuration to an overlapping configuration in response to a circumferential force applied to the petals. At least some of the petals may be overlapped in the resting configuration and the overlap is increased in response to a circumferential force applied to the petals. The tissue guard may comprise a ring from which the petals extend. The ring may be a mounting ring to which the petals are mounted.

Figure 106:
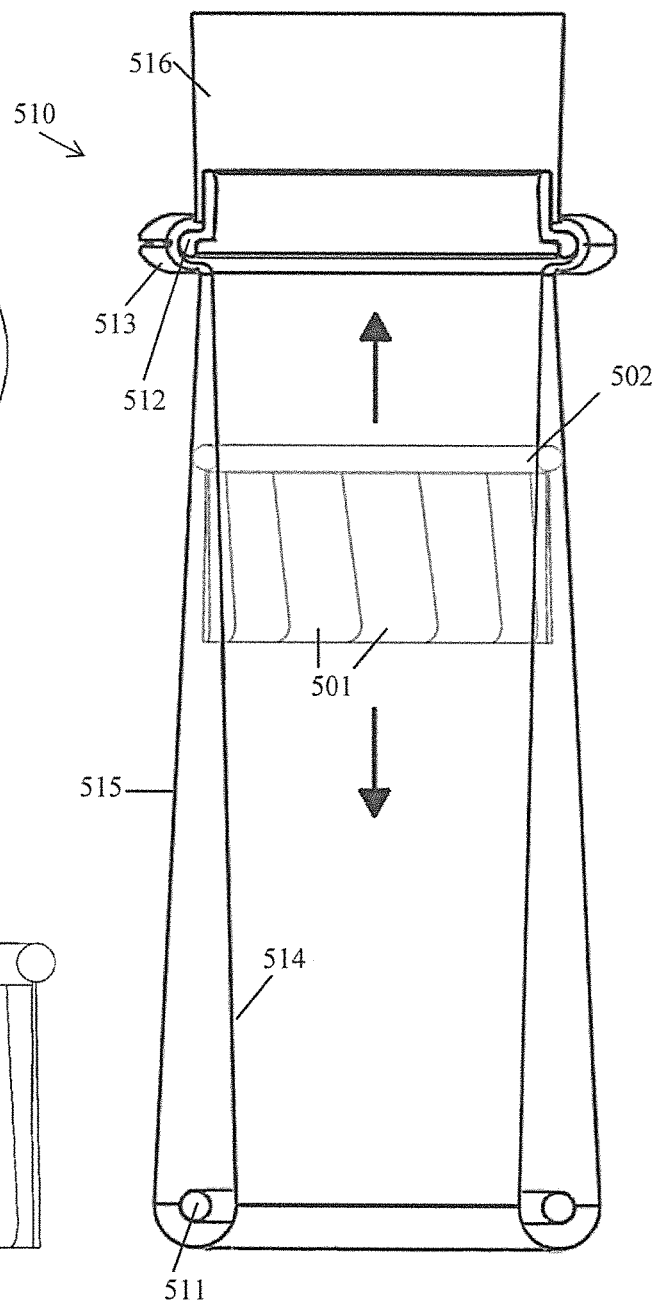
FIGS. 106 to 108 illustrate the guard of FIGS. 104 and 105, in use.

The tissue guard may be used in association with a retractor 510 such as the retractor illustrated in FIG. 106. The retractor comprises a distal member such as a ring 511 and a proximal member such as a proximal ring 512 which is engageable with a guide member 513. The retractor comprises a sleeve having a first sleeve portion 514 extending distally from the proximal ring 512 to the distal ring 511 and a second sleeve portion 515 which extends proximally from the distal ring 511 to the guide member 513. The sleeve also comprises a proximal portion 516 for pulling the sleeve upwardly to shorten an axial extent between the distal ring 511 and the proximal ring 512.

Figure 107:
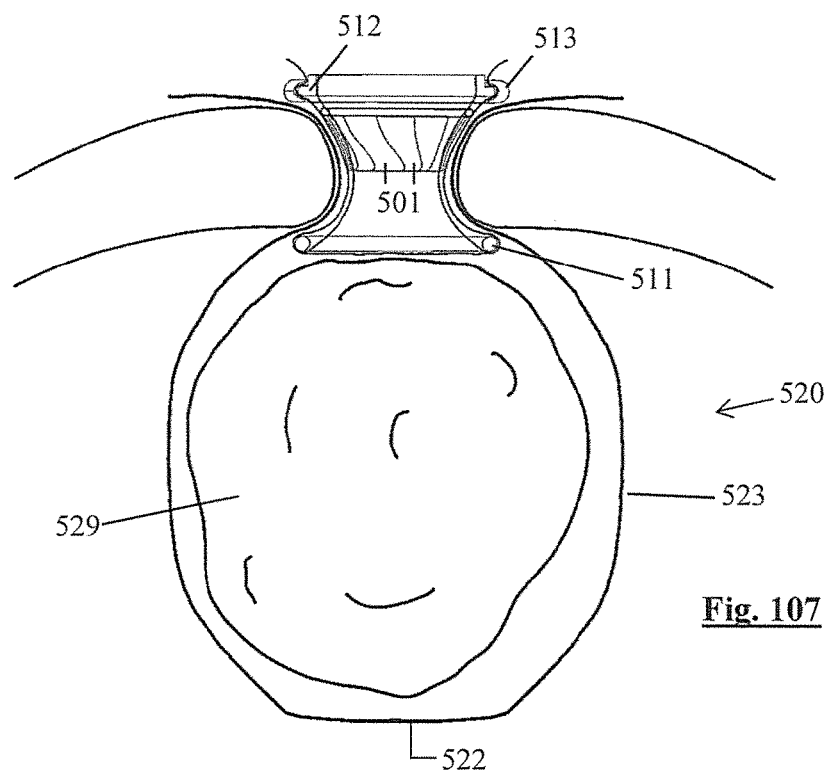
Figure 108:
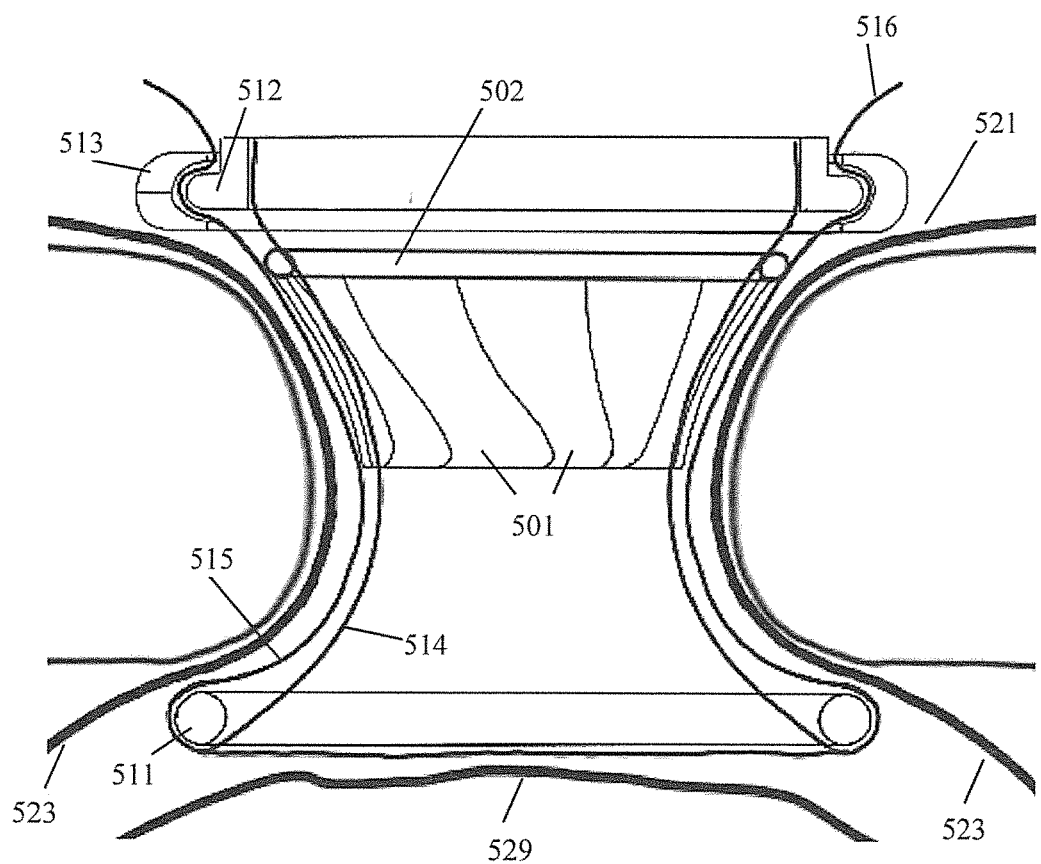
Figure 109:
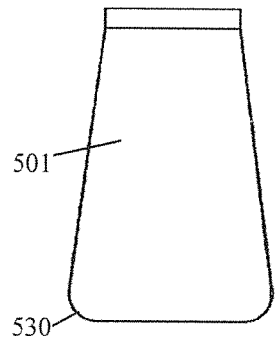
FIGS. 109 to 112 are views of petals of different shape.
Figure 110:
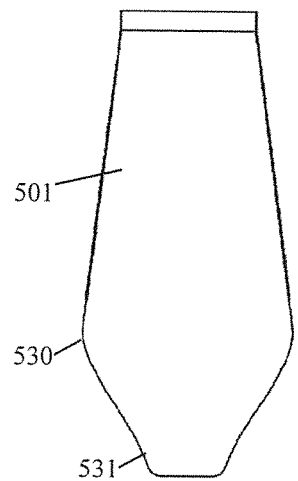
Figure 111:
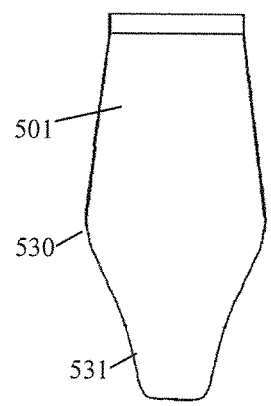
Figure 112:
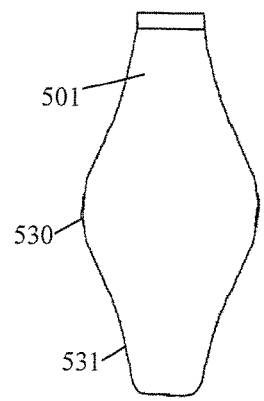

The tissue guard may also be used in association with a tissue containment bag such as the containment bag illustrated in FIGS. 107 and 108. The tissue containment bag 520 comprises an open top end 521 and a closed end 522 opposite to the open end 521. A wall 523 extends from the open end 521 to the closed end and the wall 523 has an interior surface 524. A tissue containment chamber is defined by the wall 523 and the closed end 522. The petals of the tissue guard are adapted to protect at least part of the wall of the tissue containment bag. The tissue guard has an exterior to protect the interior surface defining a passage for receiving an instrument for acting on tissue 529. One such instrument is a manual instrument such as a scalpel.

Figure 104:
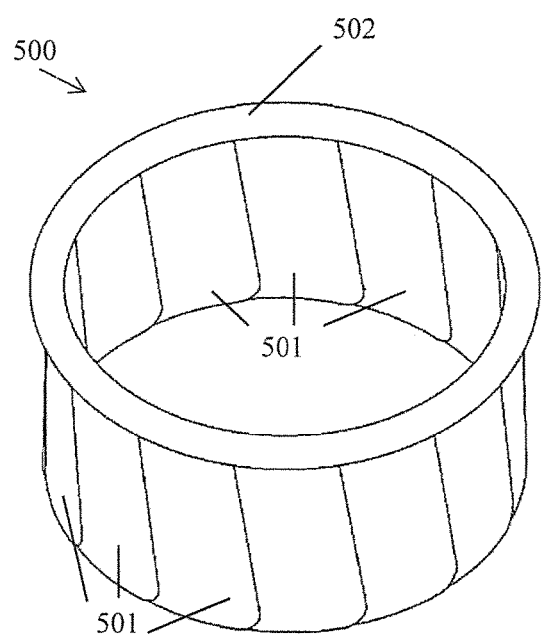
FIGS. 104 and 105 are views of another guard according to the invention.
Figure 105:
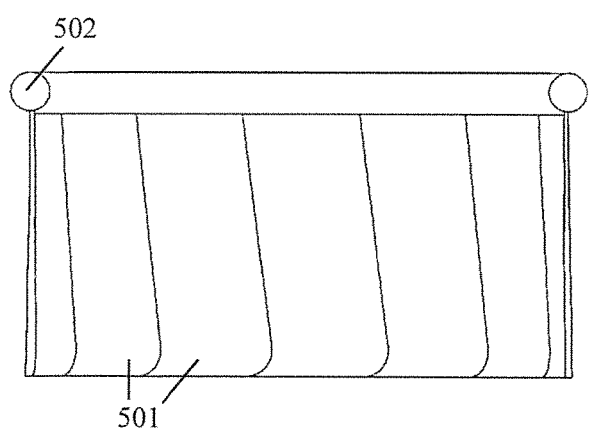

Referring to FIGS. 104 to 106, there is illustrated a tissue guard 500 comprising a plurality of petals 501 which in this case are fixed to an independent ring 502 or equivalent. The ring 502 and the petal components 501 are free to float up and down within the sleeve portions 514, 515 of the base retractor. The ring 502 can be rigid or semi-rigid, as can the petals 501. The tissue guard may be assembled from different components and materials or be a one-piece mould design.

Referring to FIG. 107 the floating petal tissue guard protects in a similar way to a guard that is fixed to the inner proximal ring 512 of the base retractor. When the sleeve of the base retractor is retracted the petal ring 502 is forced to be seated between the proximal ring 512 of the retainer and the abdomen and the petals 501 are passively retracted to the incision walls by the sleeve portions 514, 515. One advantage of the floating design is that the rigid mounting ring 502 for the petals 501 can be inwardly offset in diameter from the diameter of the inner proximal ring 512 of the retractor and therefore not obstruct the proximal ring 512 seating directly onto the abdomen. The petal ring 502 can be sized more appropriately to the incisional orifice size. FIG. 108 shows this offset in diameter more clearly.

The petals may typically have a length in the range of 15 mm to 60 mm, usually from 25 mm to 40 mm. The thickness of the petals may typically be in the range of from 0.1 mm to 1.5 mm, usually from 0.2 mm to 0.5 mm. The petals may be of any suitable material such as a cut resistant material which may be a semi-rigid material, for example, a rubber or plastics such as polycarbonate, polyurethane, polyethylene and the like.

The petal mounting ring typically has a diameter in the range of from 40 mm to 80 mm, usually from 50 mm to 70 mm.

Referring to FIGS. 109 to 112 a petal 501 may have numerous different shapes and profiles. There may be at least one section 530 which is wider than the rest of the petal in order to facilitate the overlap at rest. The petal 501 may have a taper 531 at its distal end to allow the petal to bend/flow around the bend at the narrowest point of the incision without obstructing adjacent petals 501.

Figure 113:
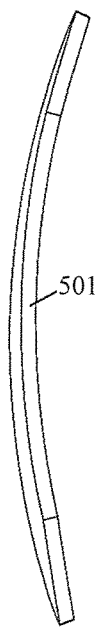
FIG. 113 is a top view of a petal.

The individual petals may be cut from a flat sheet or may have a pre-determined shape set into each petal such as shown in FIG. 113 (from a top view). A pre-shaped (curved/bent) petal may be preferred in order to bias the petal 501 to conform to the incision walls. The shaping may be achieved by moulding.

Figure 114:
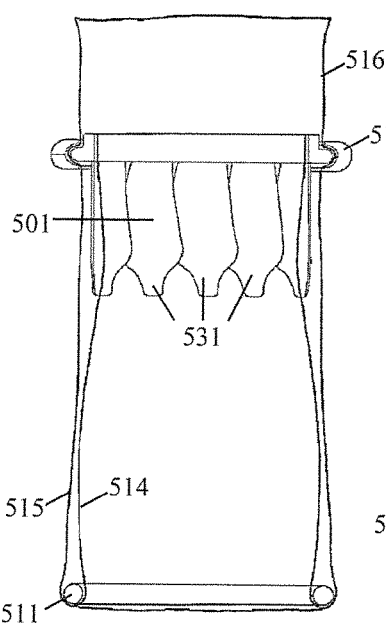
FIGS. 114 and 115 illustrate a guard comprising tapered petals, in use.
Figure 115:
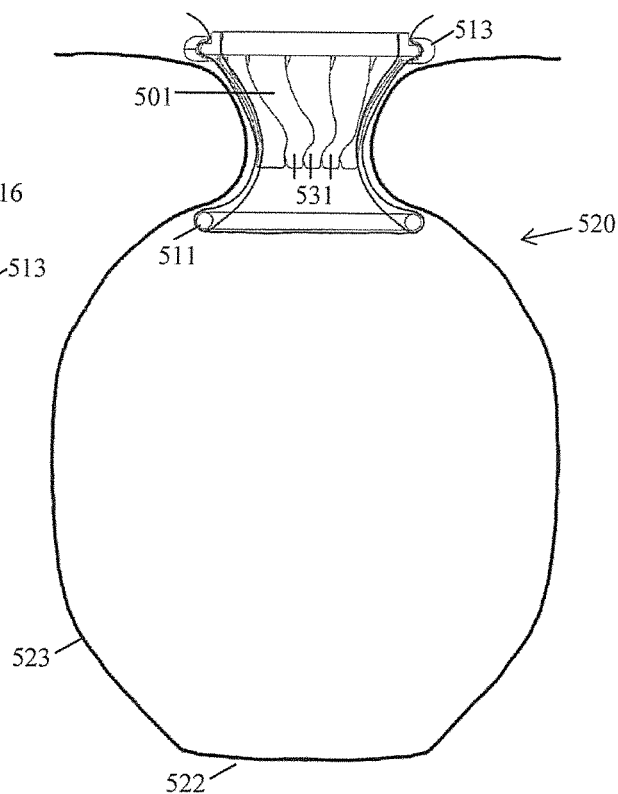

FIGS. 114 and 115 show how a tapered 531 petal profile 501 maximizes incision coverage without excessive obstruction of adjacent petals 501 at the narrowest part of the incision, thus increasing protected areas and not taking up excessive space in the incision. The petal length is such that the petal reaches, at a minimum, at or near the centre of the incision from the rigid mount ring 502 or inner proximal ring 512.

The sleeve of the base retractor may have a split-sleeve portion whereby the sleeve is split in one or more places along the long edge of the sleeve in order to remove excess sleeve from the incision area following retraction.

Figure 116:
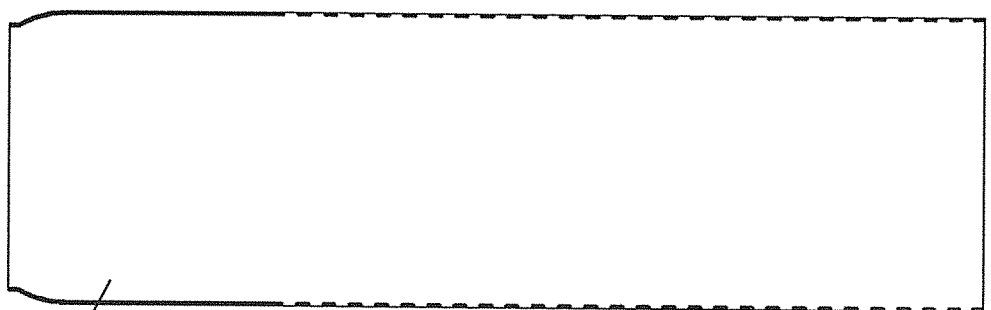
FIGS. 116 and 117 illustrate a base retractor with a split sleeve.
Figure 117:
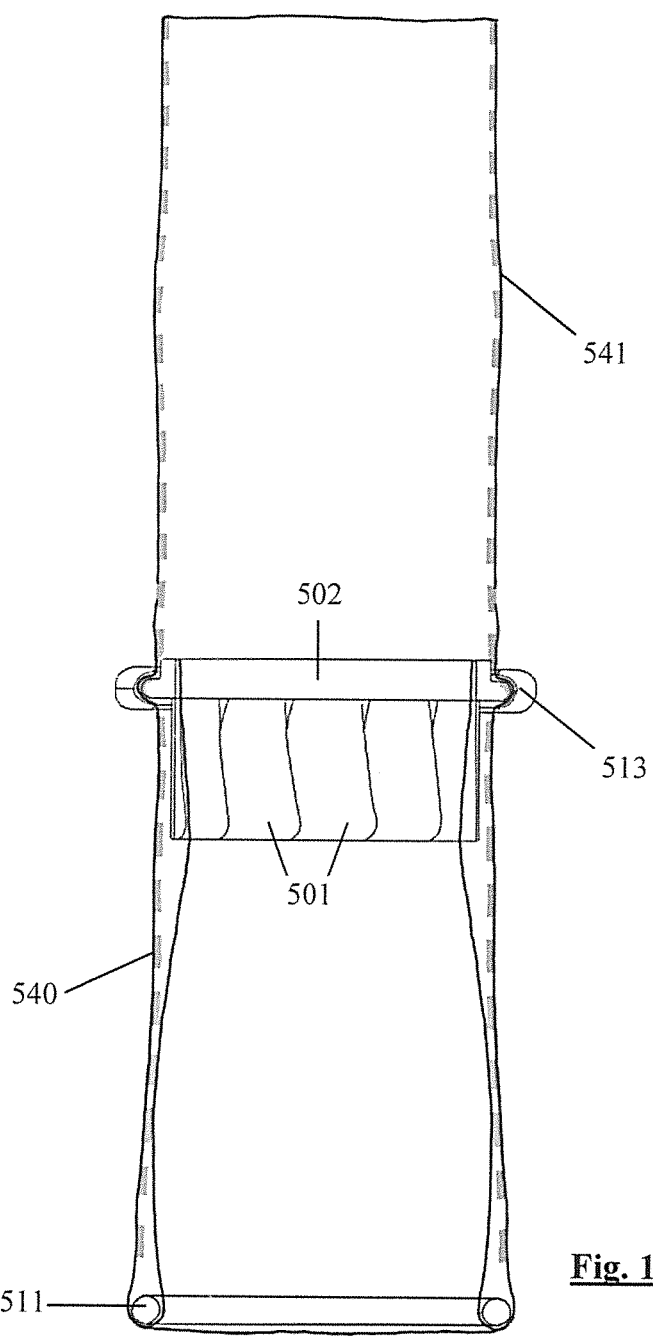

FIGS. 116 and 117 show a split sleeve 540. The split may be provided by performing and intermittent weld 541 along the long edge, or part thereof, in order to create a structured but perforated sleeve that is optimized for splitting. The sleeve may have a solid continuous weld along some portion of the total length or one or both sides.

Figure 118:
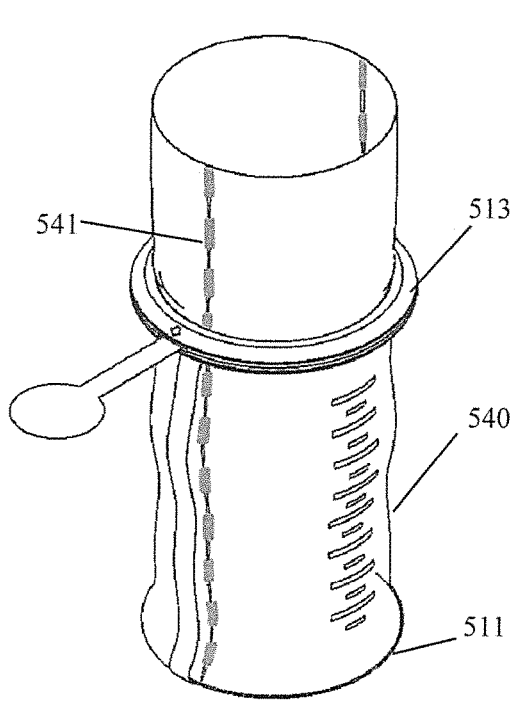
FIGS. 118 to 121 are images showing the split sleeve retractor in different configurations of use.
Figure 119:
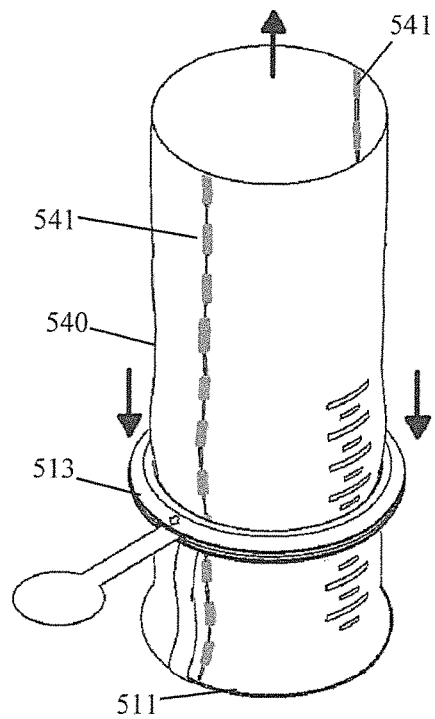
Figure 120:
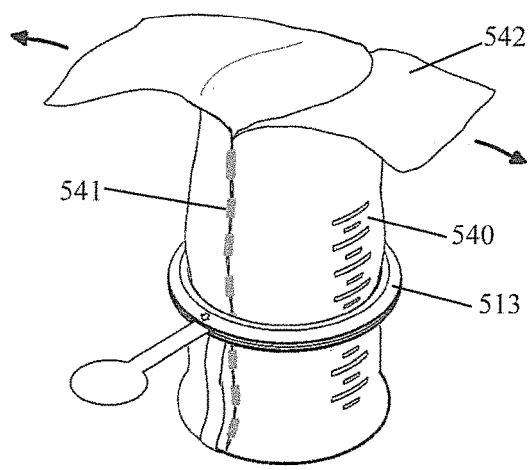
Figure 121:
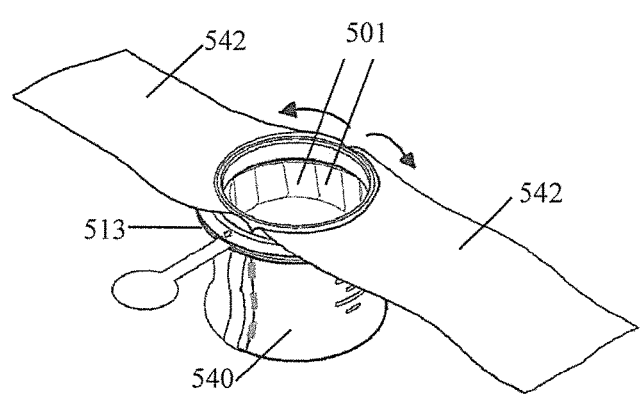

FIGS. 118 to 120 illustrate a split-sleeve 540 in use. An intermittent weld 541 along a section of the sleeve can be seen. Following retraction, the sleeve 540 may readily be split by pulling apart. When the sleeve 540 is split as far down as the outer proximal ring 513 the sleeve 540 may be completely removed from the operating area. This sleeve portion 542 can be available to readjustment of retraction at a later stage.

The system may be provided with a bag for containment of tissue.

The tissue containment bag may in some cases generally cylindrical having a length in the range of from 250 mm to 500 mm and a diameter in the range of from 50 mm to 250 mm.

The bag may be of a suitable material such as polyurethane, polyethylene or a thermoplastic elastomer.

Figure 122:
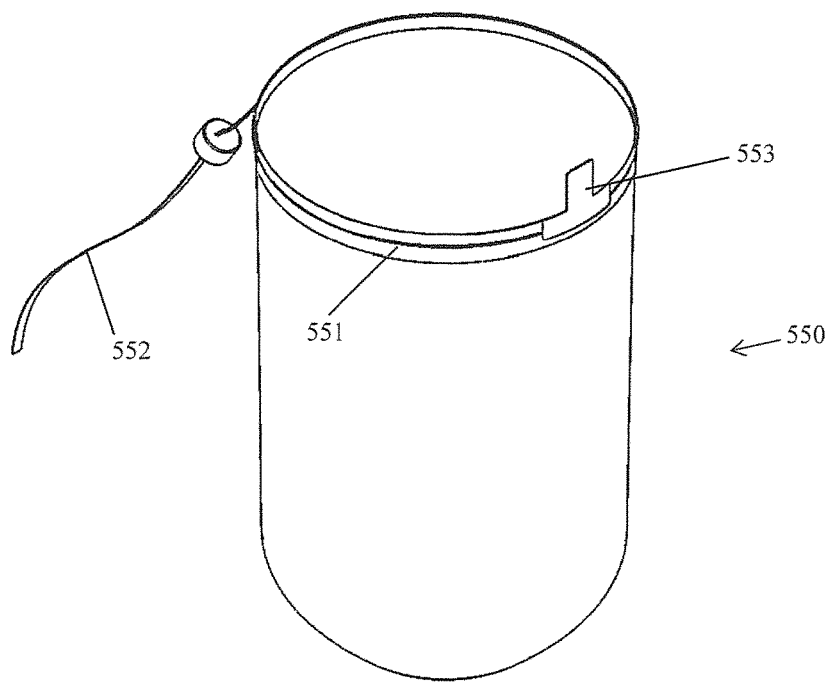
FIG. 122 is an isometric view of a containment bag.
Figure 123:
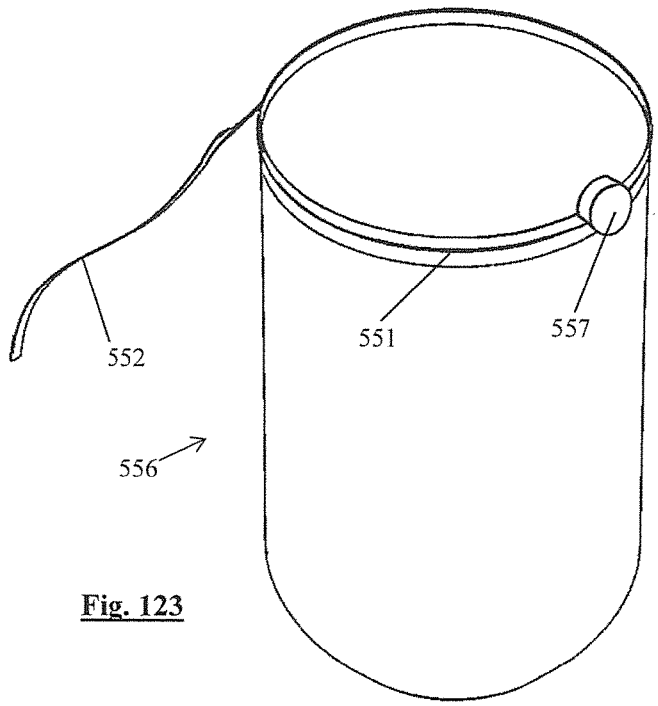
FIG. 123 is an isometric view of another containment bag.

FIGS. 122 and 123 show a tissue containment bag 550 that may be rolled up tightly and inserted into a tube that will fit into a 12 mm trocar (13 mm O.D, 12 mm I.D). The bag has an opening nitinol ring 551 entrapped in a proximal cuff 562 created circumferentially at the top of the bag. It has removal tether 552 and distal tab 553.

FIG. 123 shows a bag 556 in which the distal tab and sealing bung (on the tether) are replaced by a distal bung 557. The distal bung 557 provides a seal for the introducer tube used for insertion and would also have markings on it to indicate the correct orientation for upright placement of the bag.

FIG. 124 shows a bag 560 that is substantially rectangular in shape when flat and may have a distal end that tapers 561 to a width narrower than the opposite open end 566. A proximal cuff 562 is created at the top of the bag by folding the bag back on itself and welding across to create a loop. The cuff 562 is used to house a Nitinol hoop 551. At the distal end of the bag, another cuff or channel 563 may be created across the bag by welding, through which a rolling element such as a pin 568 may be inserted for the purpose of rolling the bag for insertion into an introducer tube Referring to FIG. 125 the proximal cuff 562 (for Nitinol ring 551) can be seen, created in this instance on a single flat sheet 570 one at a time, by folding the bag sheet back on itself and welding. This represents one half of the end product bag.

Referring to FIGS. 126 to 128, by placing two identical sheets 571, 572 on top of each other and welding the edges up to the bottom of the cuff, a bag can be created with open loops at the top.

FIG. 129 is a section through an upper portion of a tissue containment bag showing the loops on either side (circumferential) that contain the Nitinol ring 551.

FIG. 130 is an enlarged view of a cuff 562 with a nitinol ring 551 contained within. The cuff 562 is purposely oversized with respect to the diameter of the Nitinol ring 551. This facilitates a bunching of the bag when pulled relative to the Nitinol wire ring 551 and therefore facilitates closure of the bag as seen in FIGS. 131 and 132 in use. The ring is relatively thin which facilitates ease of gripping by an instrument such as a grasper. This is important to facilitate manipulation by a clinician, in use.

FIGS. 133 and 134 show the distal cuff or channel 563 created at the bottom end of the bag.

As shown in FIGS. 135 and 136, a rolling rod/pin 568 can be inserted through this channel 563 and used to initiate a tight rolling of the bag sufficient for insertion into the introducer tube. FIG. 136 shows a section through a tightly rolled bag on a rolling pin 568.

Figure 137:
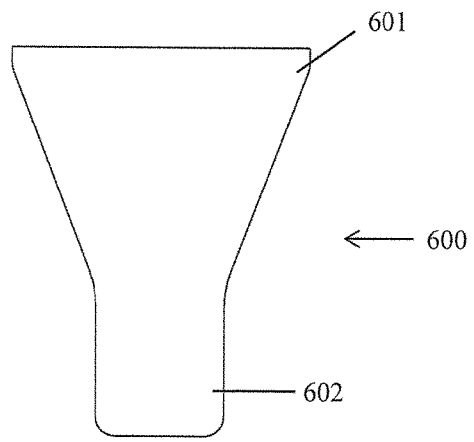
FIG. 137 illustrates a profile of a petal.

FIG. 137 illustrates the profile of a petal 600 in which the petal is widest at the top or proximal end 601 and narrower at the bottom or distal end 602. The narrower portion 602 at the distal end allows the petal to bend/flow around the bend at the narrowest section of the incision without obstructing adjacent petals.

Figure 138:
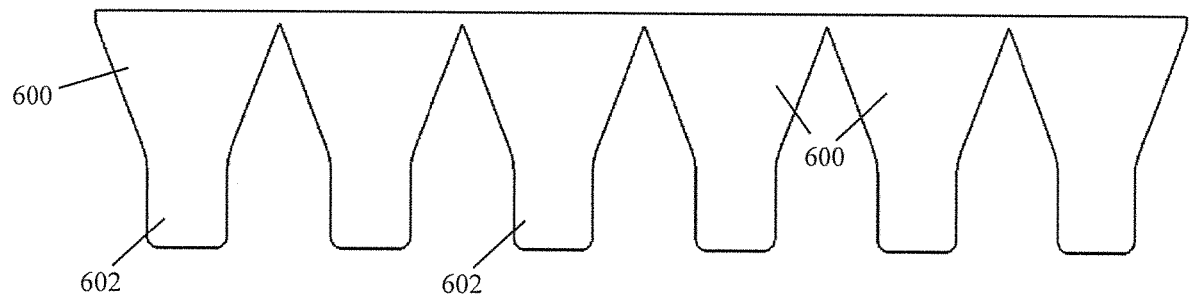
FIG. 138 illustrates a blank comprising a plurality of petals.

FIG. 138 illustrates a blank 605 in which a number of petals 600 are formed, for example by stamping. The blank is a single sheet which may be configured in a circular orientation. This provides a substantial manufacturing benefit. There may be a minimum of two petals up to possibly 12 or more in one sheet.

Figures 139, 140:
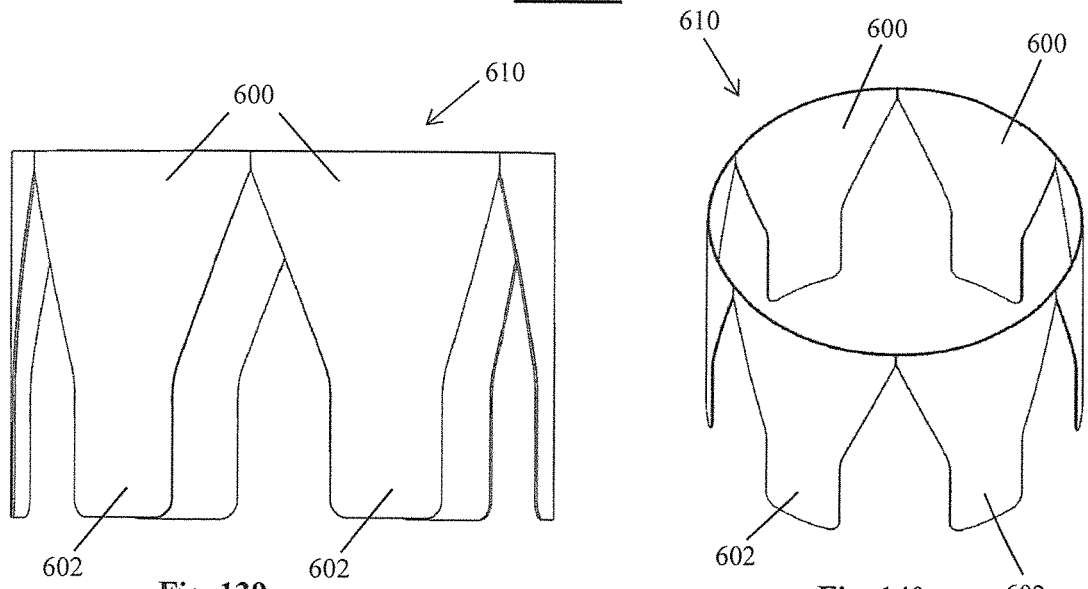
FIGS. 139 and 140 illustrate a protector/guard which is made using the blank of FIG. 138.

FIGS. 139 and 140 illustrate a protector guard 610 which is made using the blank of FIG. 138.

Figure 141:
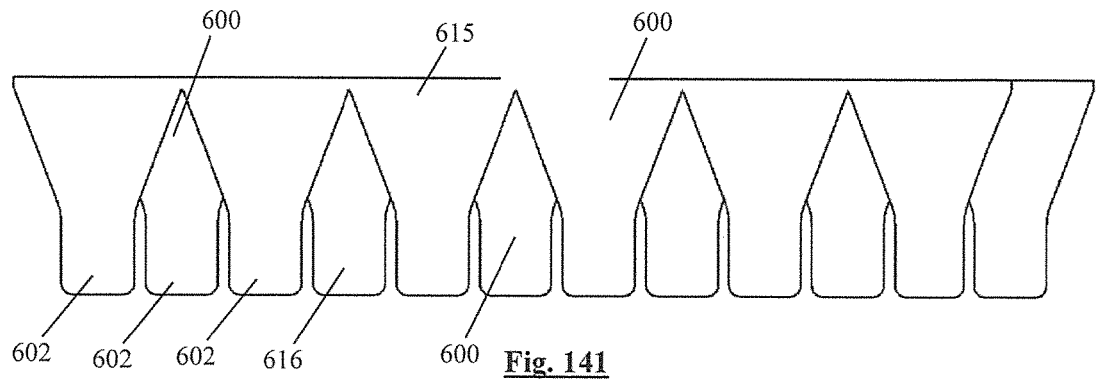
FIG. 141 illustrates an overlap of petals achieved by using two blanks in which the petals are offset.
Figures 144, 145:
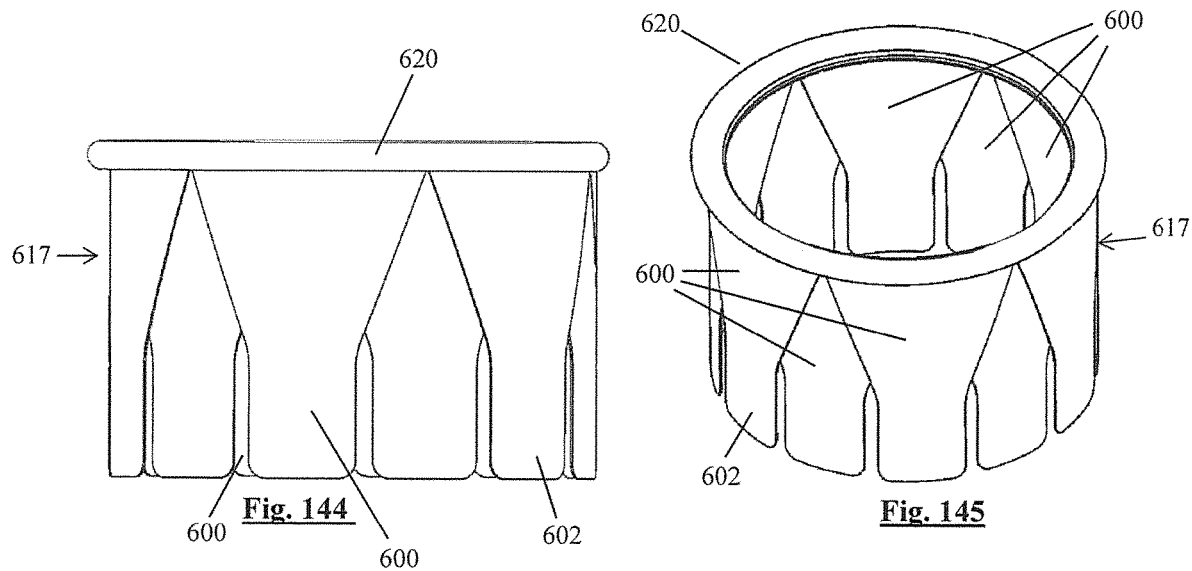
FIGS. 144 and 145 illustrate the blanks of FIG. 141 mounted to a common ring.
Figure 146:
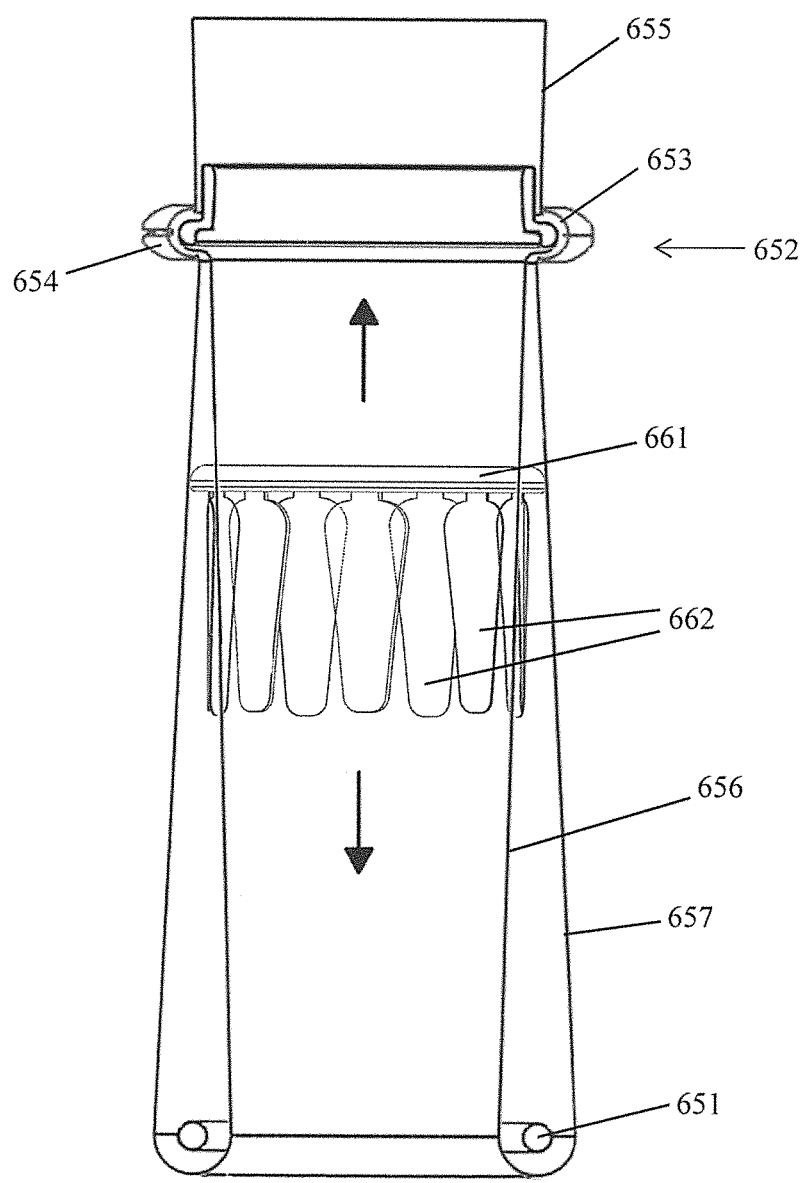
FIG. 146 illustrates a guard and a retractor.

FIG. 141 illustrates an overlap of petals which may be achieved by placing an identical or similar array 615 of petals on top of, and offset from, a first array 616 as illustrated in FIG. 140 and then configuring to a circle as shown in FIGS. 145 and 146 to provide a protector/guard 617 with overlapped petals. In this case the overlap may be achieved through a two layer arrangement rather than an immediate overlap to adjacent petals 600.

Figures 142, 143:
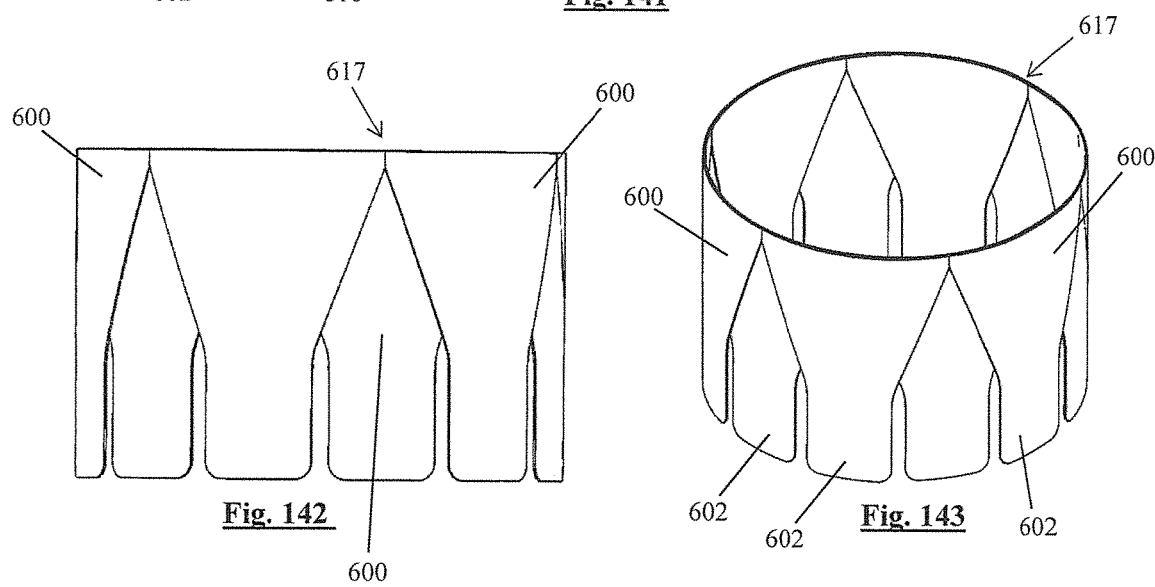
FIGS. 142 and 143 illustrate a tissue protector/guard made using the blanks of FIG. 141.

In use, when flexed by the base retractor and/or incision the narrower lower portion 602 of the petals 600 conform to the incision. FIGS. 142 and 143 show the mounting of the petal arrangement to a ring 620 which may be rigid or semi-rigid.

The invention provides an apparatus comprising a retractor and a guard device for placement in an opening such as an incision or a natural body opening such as the vagina. The retractor having an insertion configuration and a retracting configuration. The guard device has an insertion configuration and a deployed configuration and is movable by the retractor from the insertion configuration to the deployed configuration as the retractor is moved to the retracting configuration.

FIG. 146 illustrates an apparatus of the invention which comprises a retractor and a guard device. In this case the retractor comprises a distal member 651, a proximal member 652 and a retracting sleeve. The sleeve extends at least between the distal member 651, which may comprise a flexible O-ring and the proximal member 652 which may comprise a proximal mounting ring 653. In this case, there is also a guide member 654 for a proximal portion 655 of the sleeve. A first sleeve portion 656 extends distally from the proximal mounting ring 653 to the distal ring 651. The sleeve is wrapped around the distal ring 651 and a second sleeve portion 657 extends proximally from the distal ring 651 to the guide member 654. The proximal portion 655 of the sleeve is pulled upwardly to shorten an axial extent of the sleeve between the distal ring 651 and the proximal mounting ring 653 and thereby exert a retracting force.

The guard device 660 comprises a mounting ring 661 which is located between the inner and outer sleeve portions 656, 657. As the proximal portion 655 of the sleeve is pulled upwardly, the guard mounting ring 661 is also pulled upwardly. The guard device comprises a plurality of individual petals 662 which are at least partially flexible.

In use, when the retractor sleeve is pulled upwardly to retract on incision, the retractor sleeve also automatically moves the petals 662. The retractor sleeve and the incision exert a circumferential force on the petals 662 and increase the overlap and resize the guard. The device is shown in use in FIGS. 93 to 95. The petals 662 are configured and sized to extend from the proximal ring of the retractor to a minimum of the narrowest part of an incision. By using multiple overlapped petals, the total overlap is spread across a multitude of overlap areas and thereby the total diameter change can be achieved with minimal effort.

The petal device provides a multitude of overlapped areas. The petal device can also function as a full retractor system. The device is configured to reach a minimum at the midpoint/narrowest point in the incision. The device accommodates full range of abdomen thickness. There is minimal encroachment into the working diameter due to sleeve pushing the guard flush to the incision.

The use of the retractor and guide apparatus within a containment bag is described above and illustrated, for example, in FIGS. 102 to 103.

Figure 147:
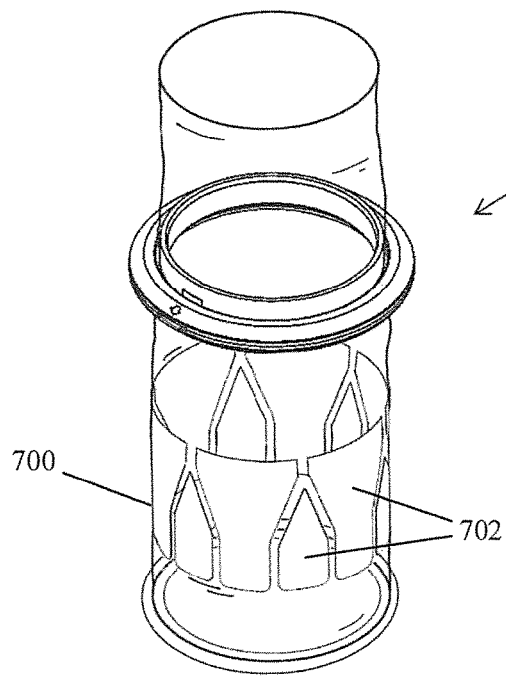
FIGS. 147 and 148 illustrate a guard of the invention mounted in or on a double sleeve retractor.
Figure 148:
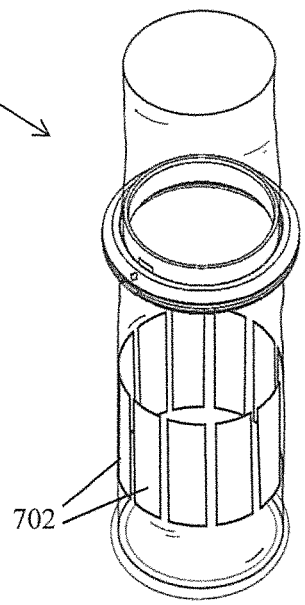

FIGS. 147 and 148 illustrate a guard 700 in association with a double sleeve retractor 701. In this case protection petals 702 may be bonded partially or completely to one or both layers of the retractor sleeve. This arrangement provides protection without a requirement for a separate floating guard.

Figure 149:
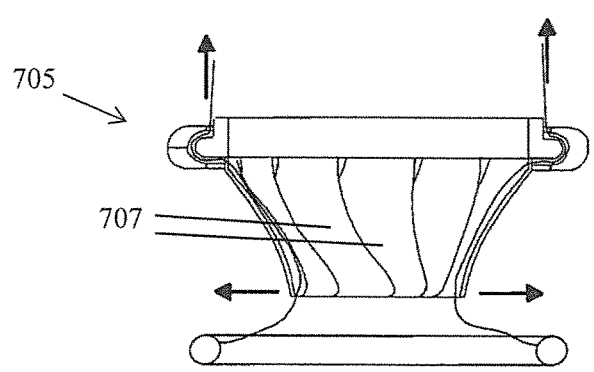
FIGS. 149 and 150 illustrate a guard of the invention mounted in or on a single sleeve retractor.
Figure 150:
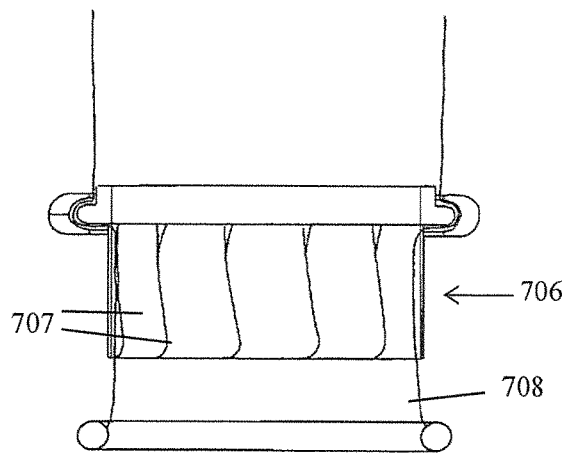

FIGS. 149 and 150 illustrate a single sleeve retractor 705 and a guard 706 of the invention. In this configuration guard petals 707 are outside the single sleeve 708 and biased inwardly. This allows the petals 707 to more easily enter an incision and then the petals are spread open to line the incision by actuation of the sleeve component to retract an opening such as an incision.

Figure 151:
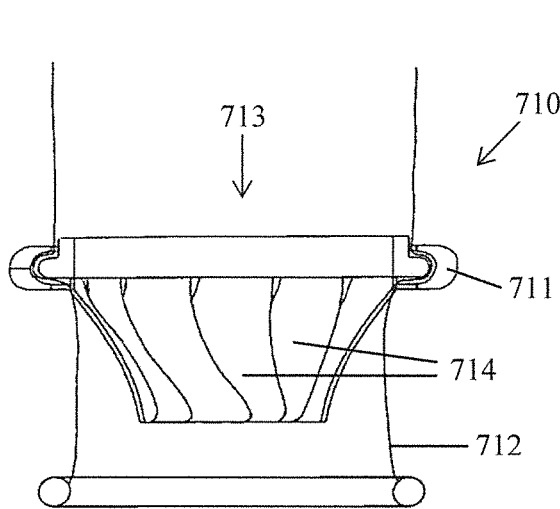
FIGS. 151 to 153 illustrate a guard of the invention inside the sleeve of a single sleeve retractor.
Figure 152:
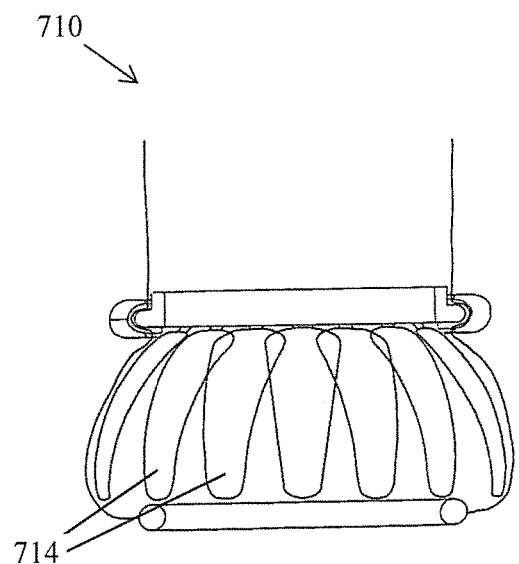
Figure 153:
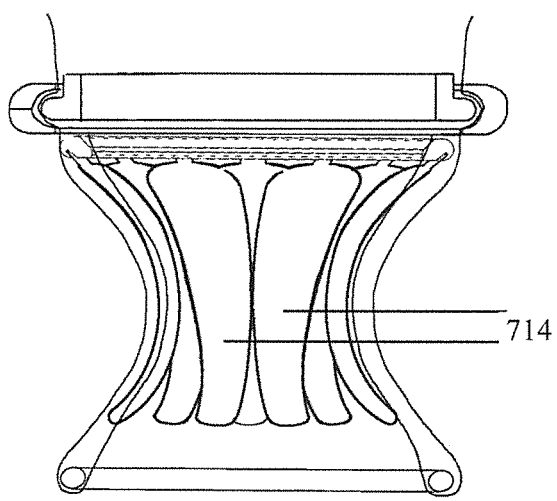

FIGS. 151 to 153 illustrate a combined retractor and guard 710 which comprises a retractor 711 having a single sleeve 712 and a guard 713 having a plurality of petals 714. In this case the guard petals 714 are inside the sleeve 712 of the retractor.

In one case (FIG. 152), the petals 714 are biased more outwardly (biased to open) so that they automatically expand to line the incision after being inserted to the incision.

Figure 154:
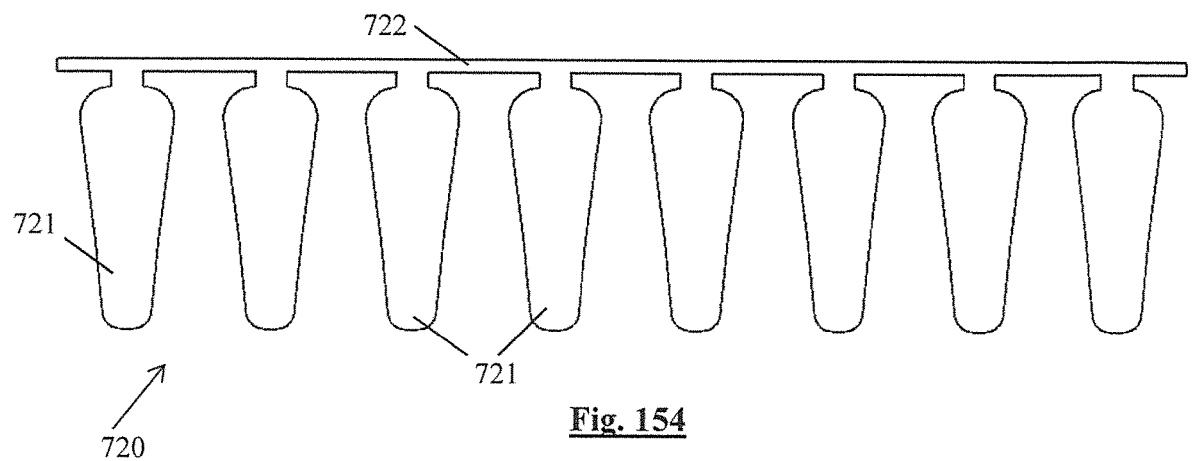
FIG. 154 shows a multi-petal guard blank before forming.
Figure 155:
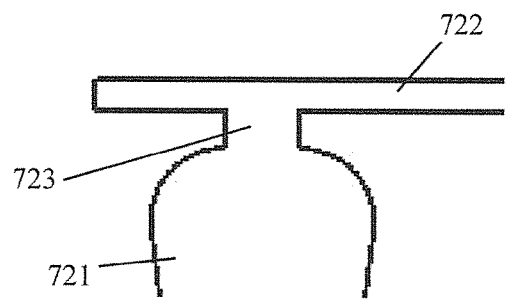
FIG. 155 is an enlarged view of a neck region of a petal.

Referring to FIG. 154 there is illustrated a blank 720 comprising a plurality of petals 721 (in this case 8 petals) which are attached to an upper linking part 722 by a narrowed neck 723. The neck 723 (which is also shown in FIG. 155) can vary in width in relation to the petal body. The petal body includes a wider upper portion and a narrower lower portion as described above. The inclusion of the narrow neck element increases the petal's freedom to rotate about this point when mounted in a circular mount ring.

Figure 156:
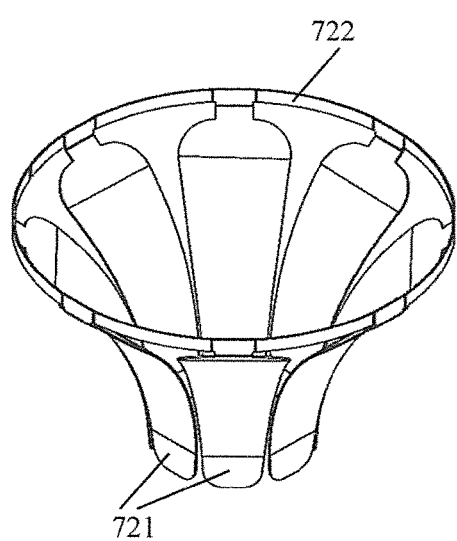
FIGS. 156 and 157 illustrate a guard formed using the multi-petal blank of FIG. 154.
Figure 157:
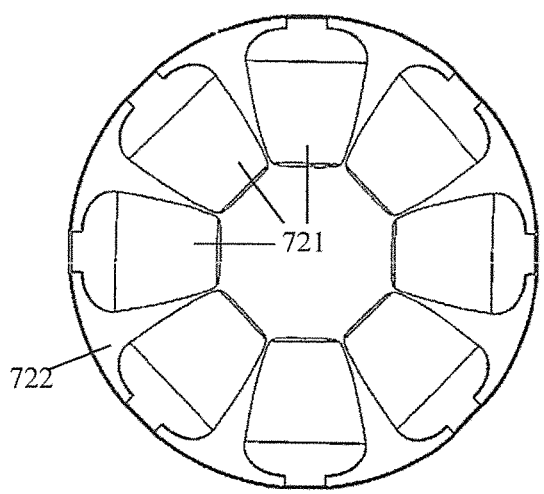

FIGS. 156 and 157 illustrate the configuration of the petals of FIG. 154 into a circular shape.

Figure 158:
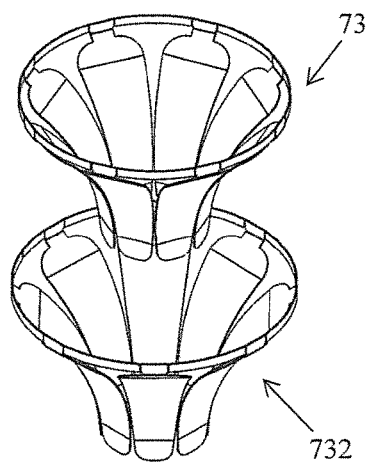
FIGS. 158 to 160 illustrate a guard comprising two layers of petals.
Figure 159:
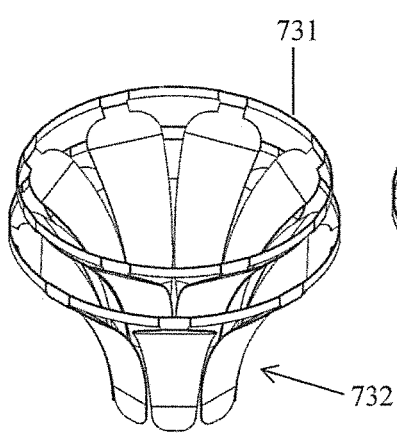
Figure 160:
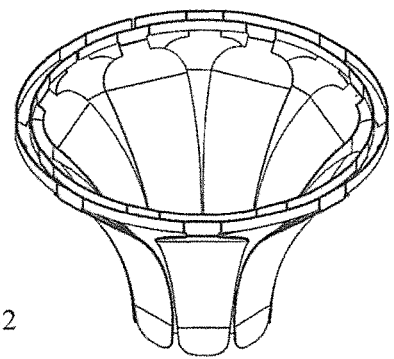

In some cases there may be more than one layer of petals. For example, there may be two layers of petals arranged in any desired configuration. For example there may be two layers of petals arranged one within another. One such arrangement is illustrated in FIGS. 158 to 160 in which two layers 730, 731 of the singular petal profile are layered concentrically and offset by one full petal section the result is an overlapped configuration where full coverage/protection is achieved.

Figure 161:
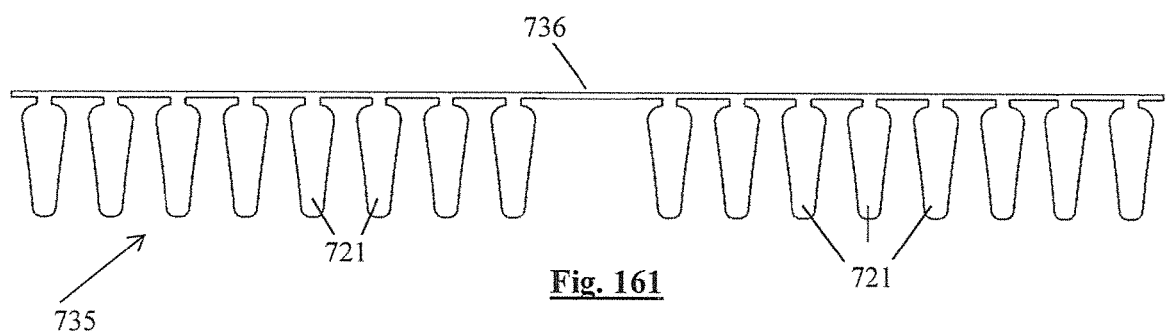
FIG. 161 illustrates a single multi-petal blank that may be used to form the guard of FIGS. 158 to 160.

This layered petal arrangement can be achieved using a single petal profile or blank 135 as shown in FIG. 161 in which all 16 petals are stamped out with an appropriate offset 736 in the middle. In this way the layers of petals can be mounted con-centrically during assembly.

Figure 162:
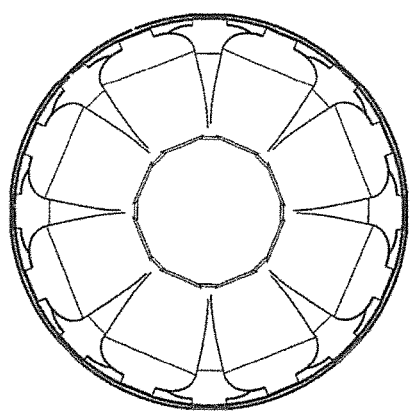
FIGS. 162 and 163 illustrate a two layer guard mounted to a mounting ring.
Figure 163:
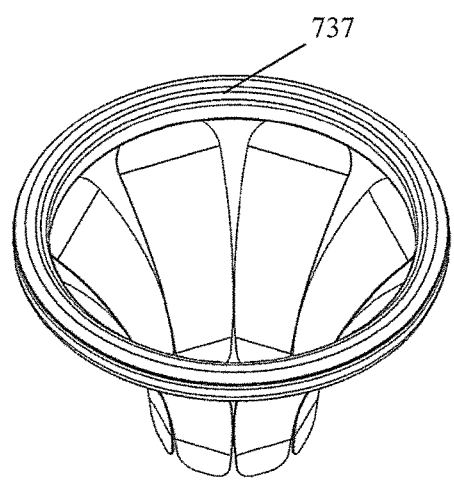

Referring to FIGS. 162 and 163 when configured into a circular shape the layered petal arrangement can be mounted into a rigid/semi-rigid/flexible mounting ring 737.

Figure 164:
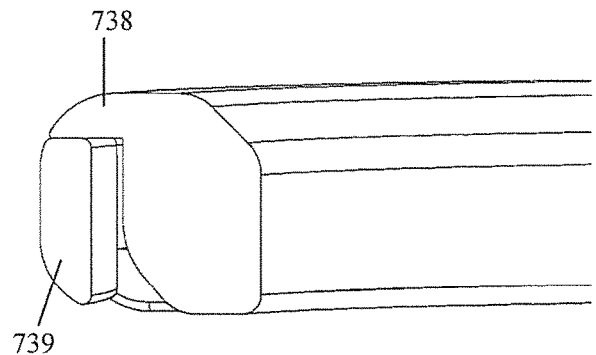
FIGS. 164 and 165 illustrate details of a mounting ring for the guard.
Figure 165:
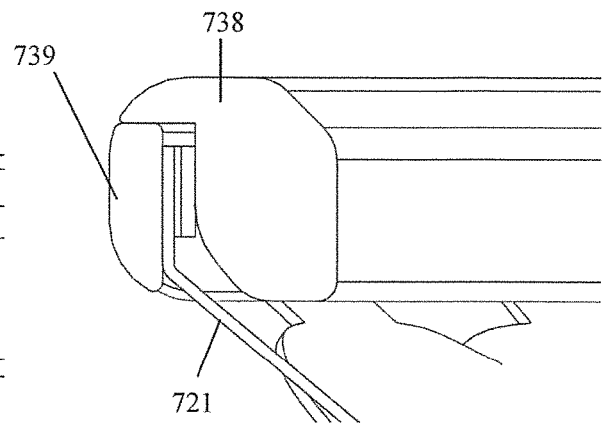

Referring to FIGS. 164 and 165 the mounting ring 737 may comprise two parts 738, 739 such as, an upper and lower component which sandwich the petals 721 into assembly whilst providing the freedom for the petals 721 to bend inwards at the petal neck 723.

Figure 166:
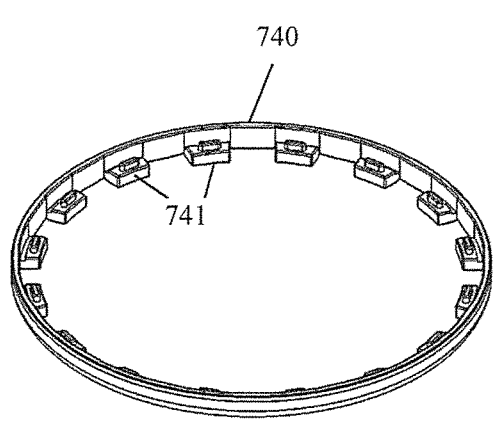
FIGS. 166 and 167 illustrate a mounting ring with features to which the guard petals may be mounted.
Figure 167:
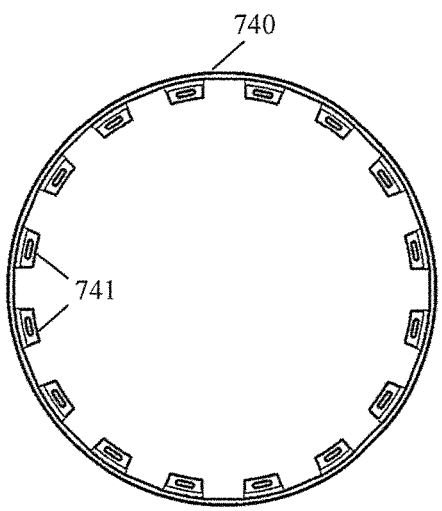
Figure 168:
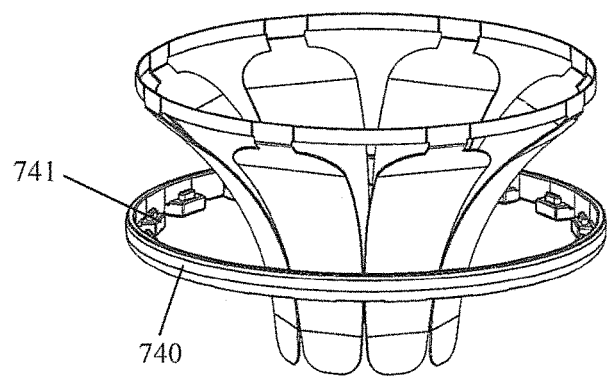
FIGS. 168 to 171 illustrate the petals being mounted on an inner ring.
Figure 169:
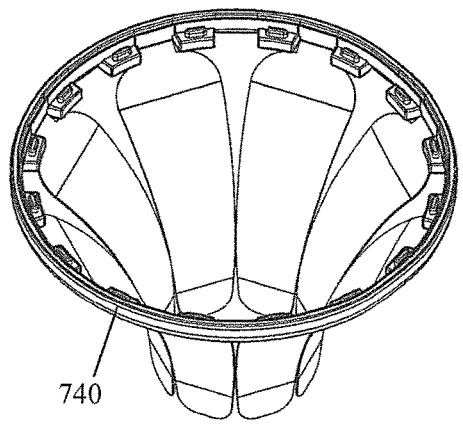
Figure 170:
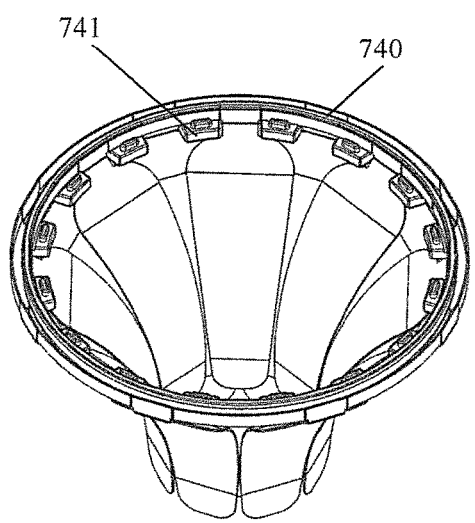
Figure 171:
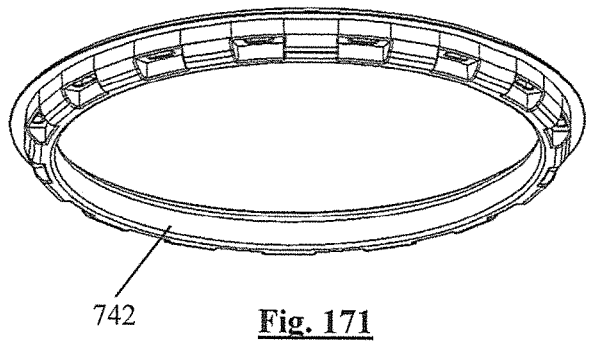

Referring to FIGS. 166 and 167 the array of petals 721 can be mounted to an inner mounting ring 740 which has inner extension features 741 to facilitate correct location of the petal arrays so that the petals 721 overlapped and offset configuration.

Figure 172:
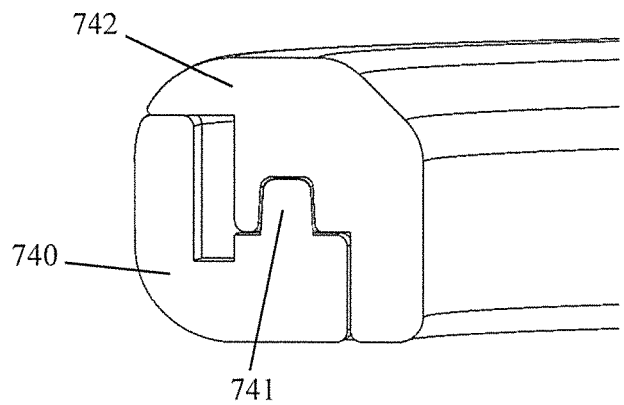
FIG. 172 illustrates the assembly of an outer ring to the inner ring.

FIGS. 178 to 172 illustrate the mounting of the petal array to the inner mounting ring 740 before an upper mounting ring 742 is assembled on top to capture the petals in place.

Petals can be unbonded within this assembly. The upper and lower mounting rings may be used to secure the petals in place.

The male and female engagement features which aid in assembly of the upper and lower mounting rings 740, 742 are shown particularly in FIG. 172.

Figure 173:
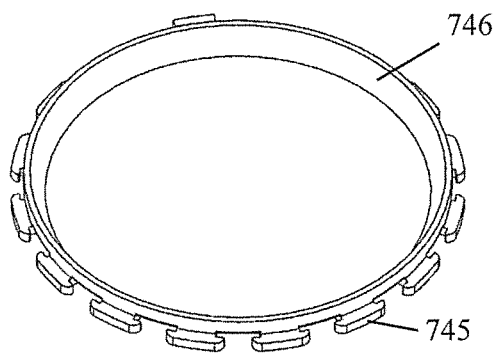
FIGS. 173 to 175 illustrate the mounting of guard petals to an inner mounting ring and an outer ring which is engaged with the inner ring to capture the guard therebetween.
Figure 174:
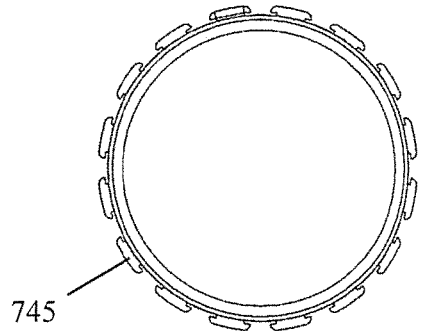
Figure 175:
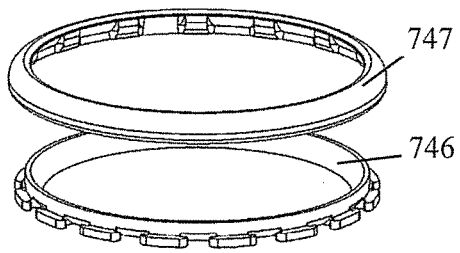
Figure 176:
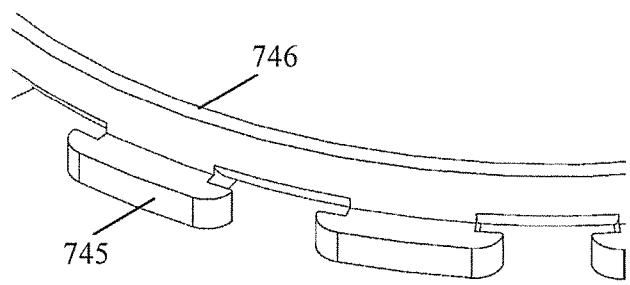

FIGS. 173 to 175 illustrate another embodiment in which the petals are mounted on features 745 on the outside of the mounting ring 746 lower before an upper mounting ring 747 is assembled on top to capture the petals.

The mounting features on the mounting ring may be configured for engagement such as snap fitting engagement with the neck region of the petals. One such configuration is illustrated in FIGS. 177 and 178. Engagement features 750 on the mount ring 751 extending feature on one or both sides as shown allow for a snap assembly where the gap between the two bump features is narrower that the petal neck. The neck deflects slightly during assembly to click into place and remain there securely.

FIG. 179 illustrates petals 755, 756 overlapped front and back in an alternating manner.

FIG. 180 illustrates petals 755 overlapped in a continuous, same direction manner.

FIG. 181 illustrates petals 760 having a long neck 761 that may be looped around a ring and bonded to itself to facilitate attachment to the mounting ring.

FIG. 182 shows petals 762, 763 of varying lengths.

FIG. 183 illustrates individual petals 765 with a neck portion 766 that can be inserted and bonded into dedicated slots 767 in a mounting ring.

Figures 185, 186:
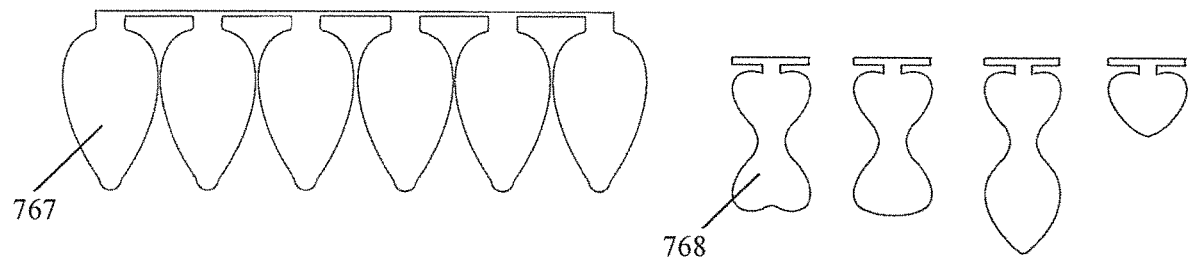

FIGS. 184 to 186 illustrate various petal shapes 766, 767, 768 having wider lower portions that may provide further protection distal to the narrowest point of the incision.

Figures 187, 188:
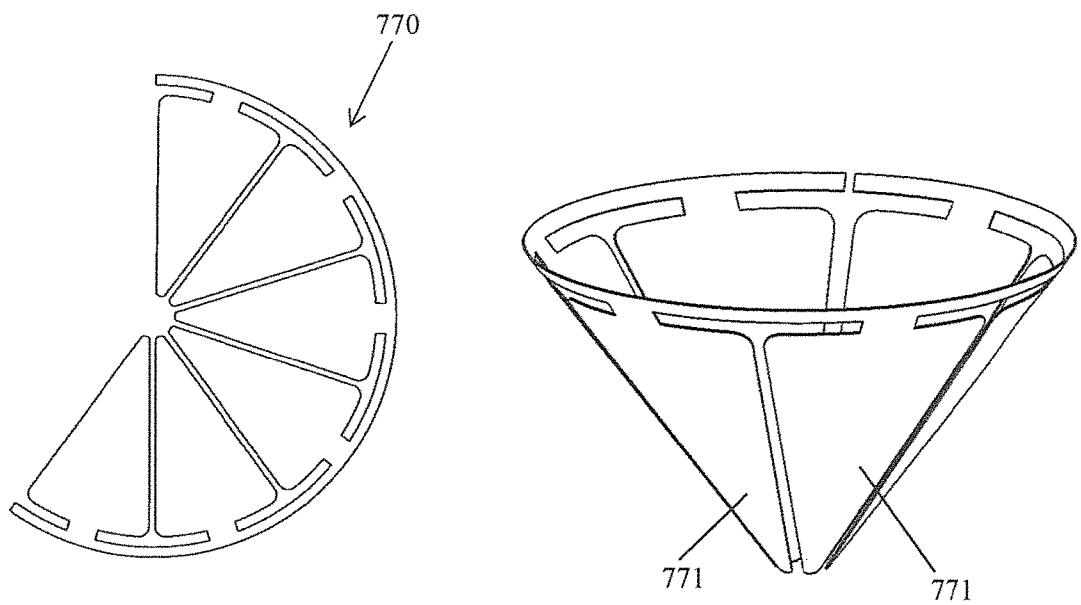
FIGS. 187 to 188 illustrate a petal configuration.
Figure 193:
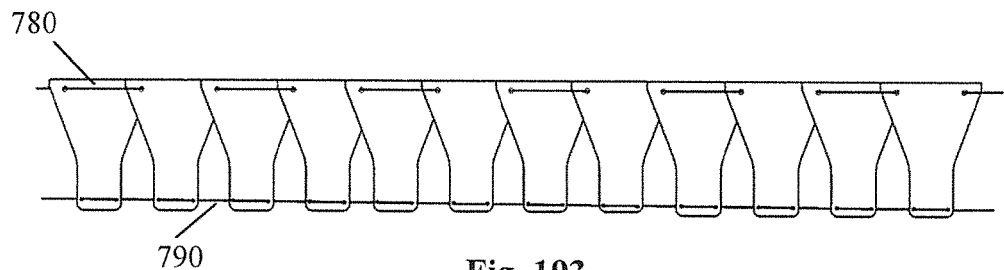
FIGS. 193 to 196 illustrate the mounting of petals to both proximal and distal wires.
Figure 194:
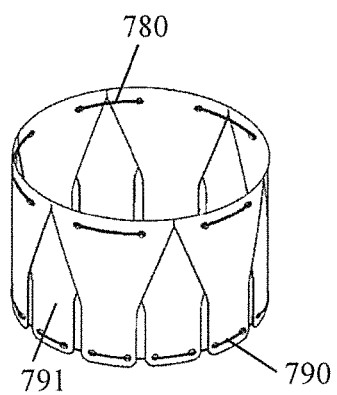
Figure 195:
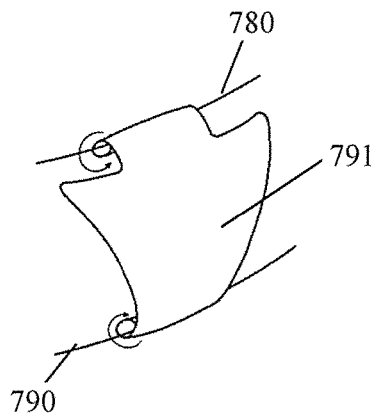
Figure 196:
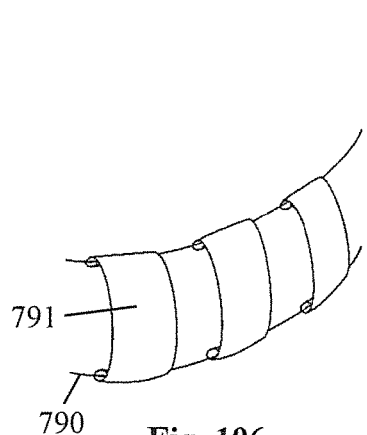
Figure 197:
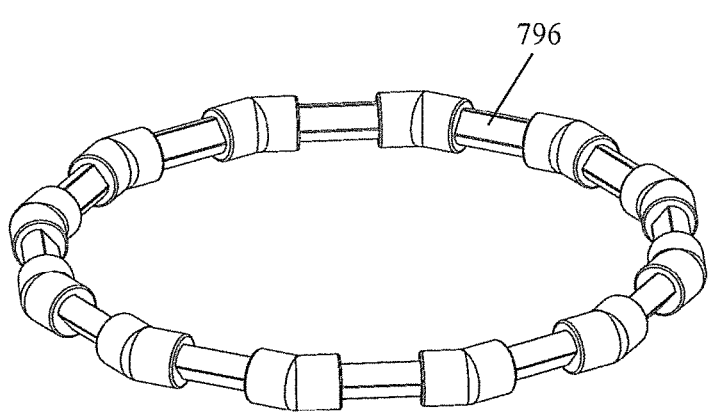
FIGS. 197 to 202 illustrate a mounting ring with features for mounting individual petals.
Figure 198:
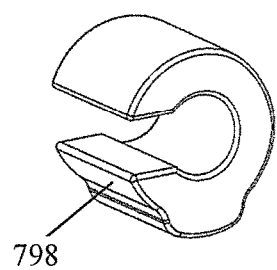
Figure 199:
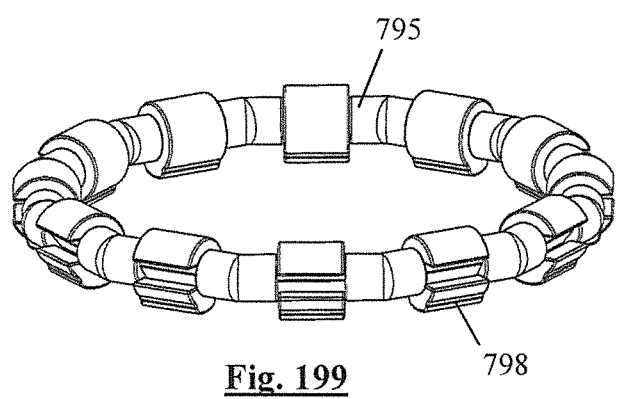
Figure 200:
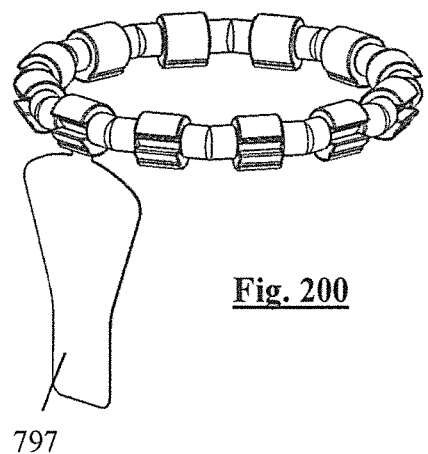

FIGS. 187 and 188 shows a petal configuration 770 that can be cut in such a way that, when assembled to a circular shape, the petals 771 are automatically biased inward and mountable at an angle to the mount ring.

It can be beneficial to mount the petals at an angle to the mounting ring so that the amount that petals are required to bend as they are introduced into an incision is reduced. The stress while bending is greatly reduced by using a narrow connection (neck) as described above but an angular mounting to the ring may also achieve similar results.

This angular petal projection from a mounting ring 772 can be seen particularly in FIG. 189.

Referring to FIGS. 190 and 191 there is illustrated another guard in which a flexible metal (or plastic) wire 780 is threaded through individual petals 781 which are overlapped. This provides the guard with another degree of freedom versus a rigid ring and at the same time facilitates rotation of the petals 781 about the wire 780.

Referring to FIG. 192 petals 785 in this case have a hoop 786 cast or moulded into their shape and this hoop 786 is used for mounting the petals 785 onto the wire 787.

Referring to FIGS. 193 to 196 there is illustrated another guard in which there is also a distal wire ring 790 threaded through the distal portion of the petals to give the guard more structure distally and to prevent petals 791 from inverting or sliding excessively.

FIGS. 197 to 202 show an example guard in which a mounting ring 795 has dedicated connection points 796 to mount individual petals 797 on individual clips 798, about which they can rotate freely.

Figure 201:
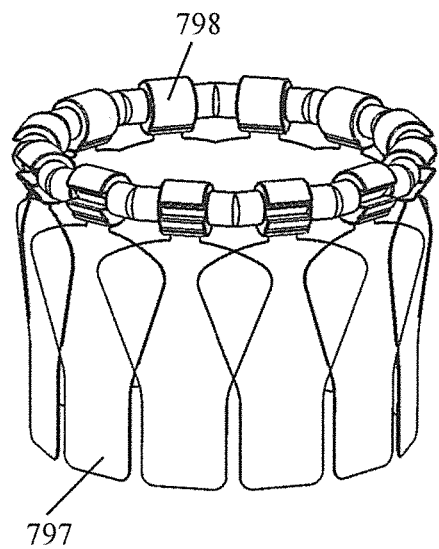

Referring to FIG. 201 shows a full assembly and illustrates the resulting overlap of the petals 797.

Figure 202:
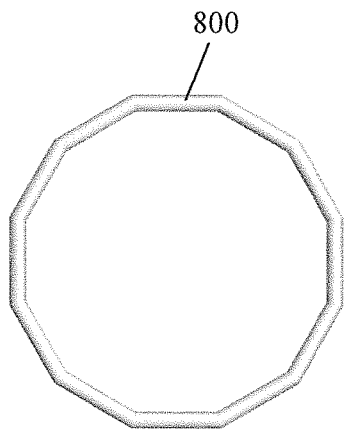
Figure 203:
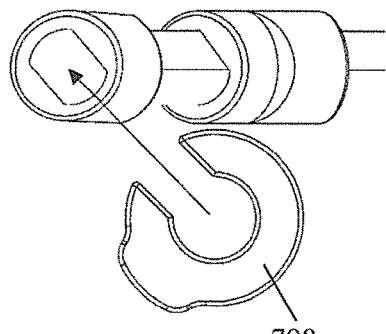
FIGS. 203 to 206 illustrate the mounting of petals to a mounting ring using clip features.
Figure 204:
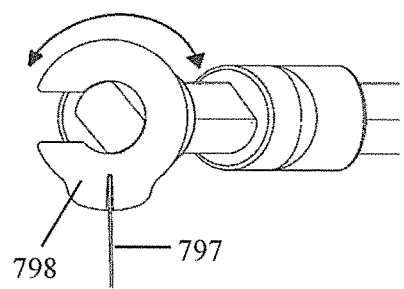
Figure 205:
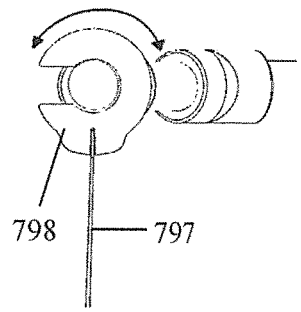
Figure 206:
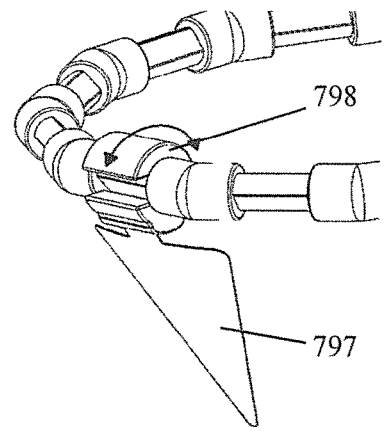

Referring to FIG. 202 a mounting ring 800 may comprise many small straight sections rather than an exactly circular ring. This facilitates less interference between petals.

FIGS. 203 to 206 illustrate one example of the clip 798 attaching to the flat section of the ring and then rotating about it.

In some cases the mounting ring may have a groove or slot or a plurality of such slots or grooves for mounting the petals to the ring.

Figure 207:
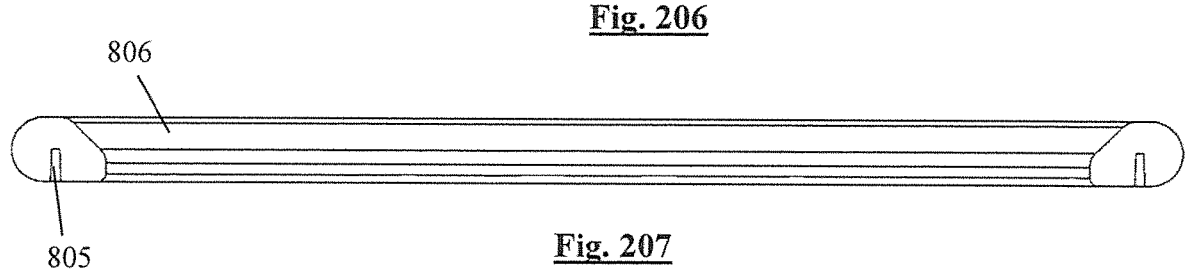
FIGS. 207 to 209 illustrate a mounting ring with a slot for mounting petals.
Figure 208:
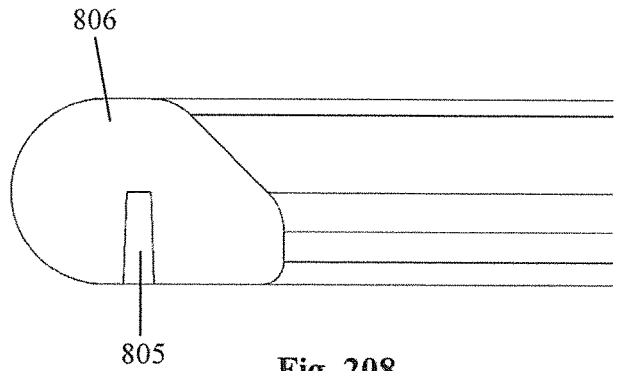
Figure 209:
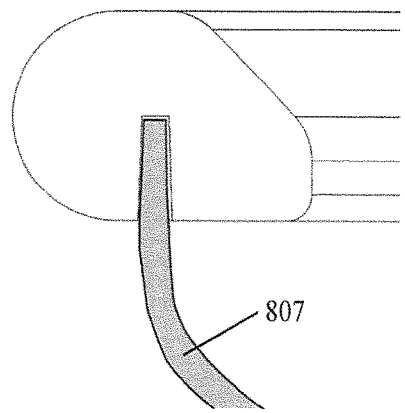

FIGS. 207 to 209 illustrate a slot 805 perpendicular to the ring 806 to mount the petals 807. As shown in FIG. 209, the petal in this case bends in towards the incision after exiting the mount ring 806.

Figure 210:
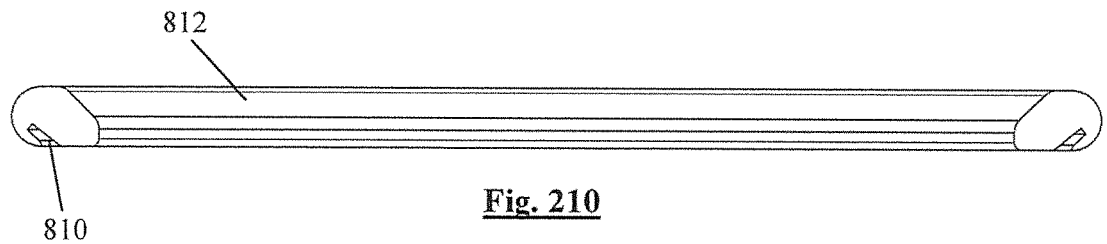
FIGS. 210 to 212 show another mounting ring with an angled mounting slot.
Figure 211:
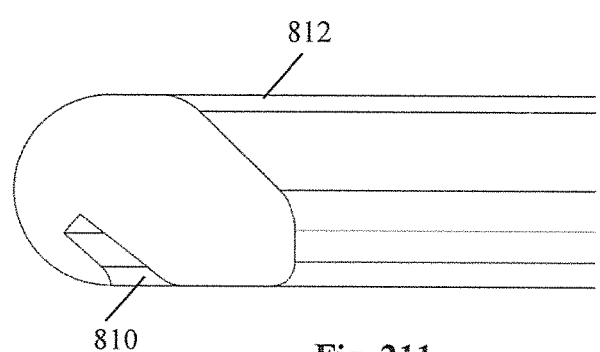
Figure 212:
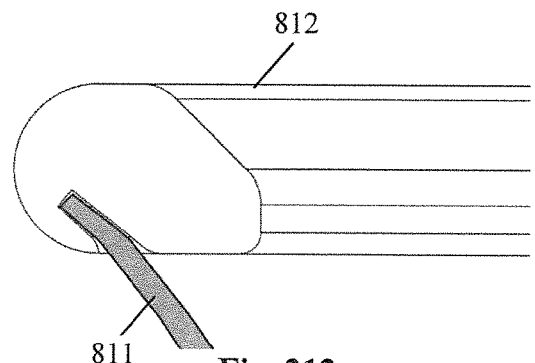

Referring to FIGS. 210 to 212 in this case an angled slot 810 in the ring ensures that the petals 811 need not bend excessively upon leaving the mount ring 812.

Figure 213:
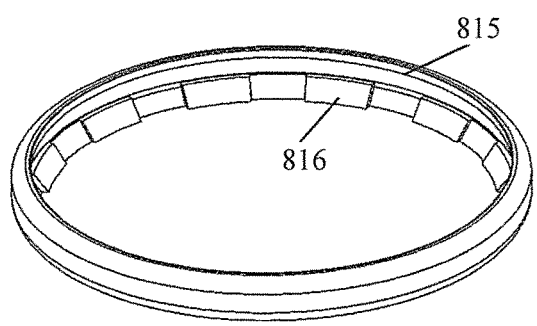
FIGS. 213 and 214 illustrate another mounting ring with angled features.
Figure 214:
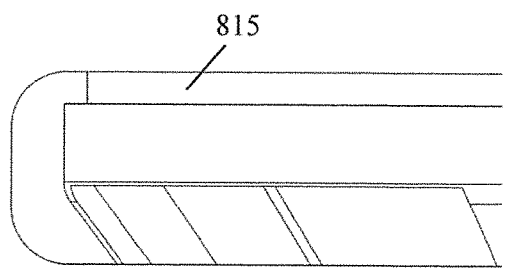

Referring to FIGS. 213 and 214 in this case the mount ring 815 has an angled feature 816 which biases the petals to bend inwardly without the need to build this angle into the petal itself. In this case, an otherwise straight petal is flexed to bias inward by the angled feature 816 in the mount ring 815.

Figure 215:
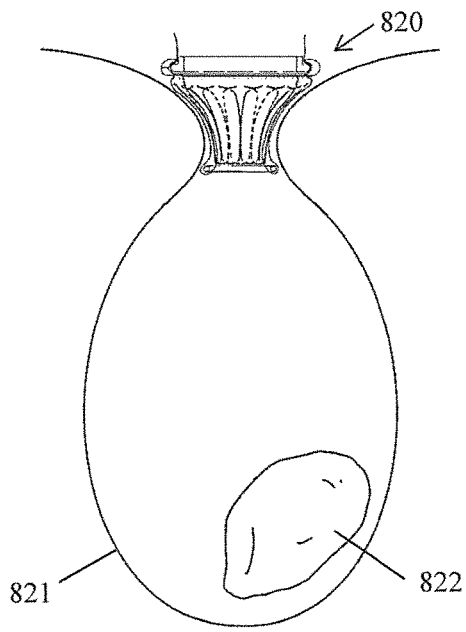
FIGS. 215 and 216 illustrate a guard of the invention in situ in a tissue collection bag.
Figure 216:
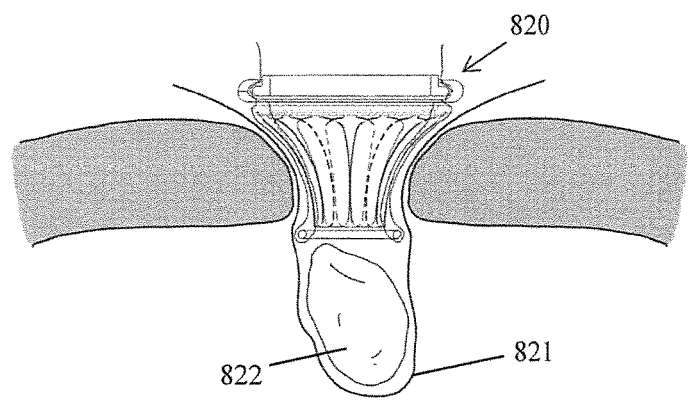

FIGS. 215 and 216 illustrate a guard 820 in situ within a bag 821 with a specimen 822 in place. The bag 821 is pulled up around the guard 820 to hold tissue 822 up against the incision, ready for morcellation.

FIGS. 217 to 220 illustrate a guard 820, a retractor and a tissue containment bag 821, in use.

Figure 217:
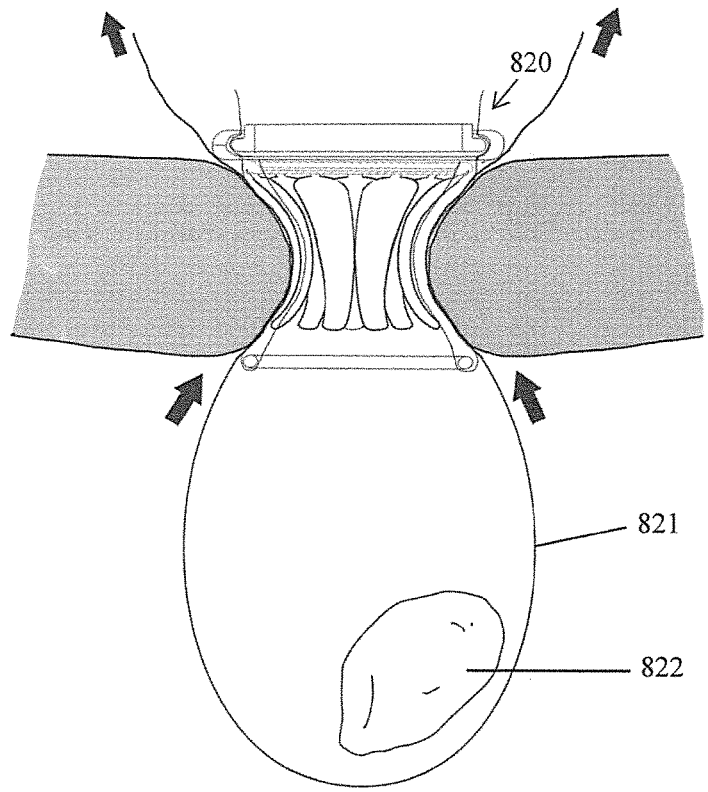
Figure 219:
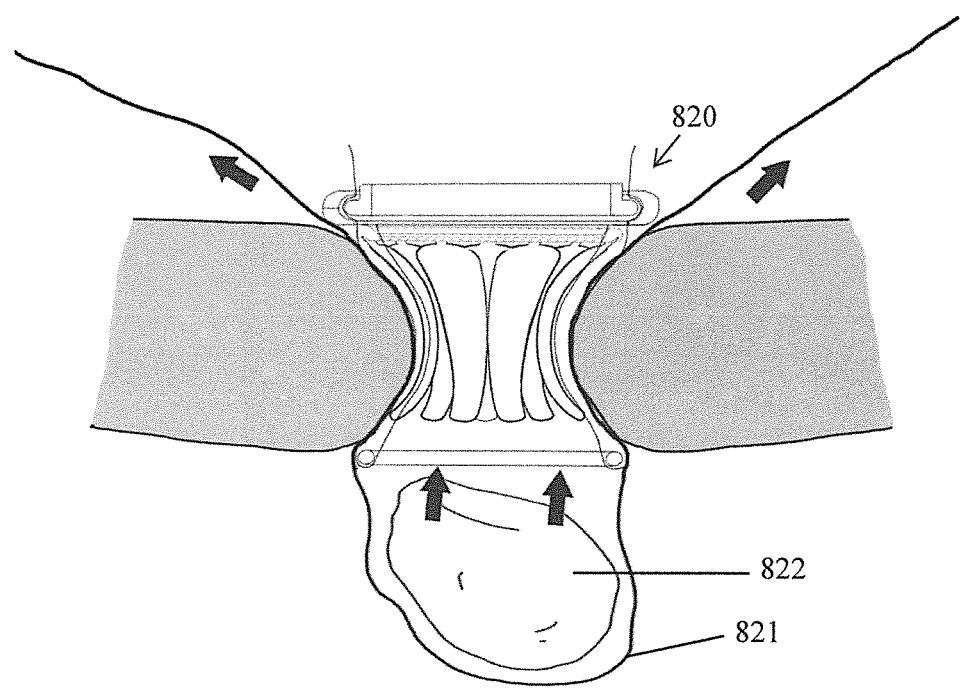

In FIGS. 217 and 219 the arrows indicate that the bag 821 is free to move around the guard retractor in order to remove excess bag material and to bring the tissue 822 towards the incision. The amount of friction present between the guard, bag, and incision holds the bag material in place following removal, thus keeping the tissue in position.

Figure 218:
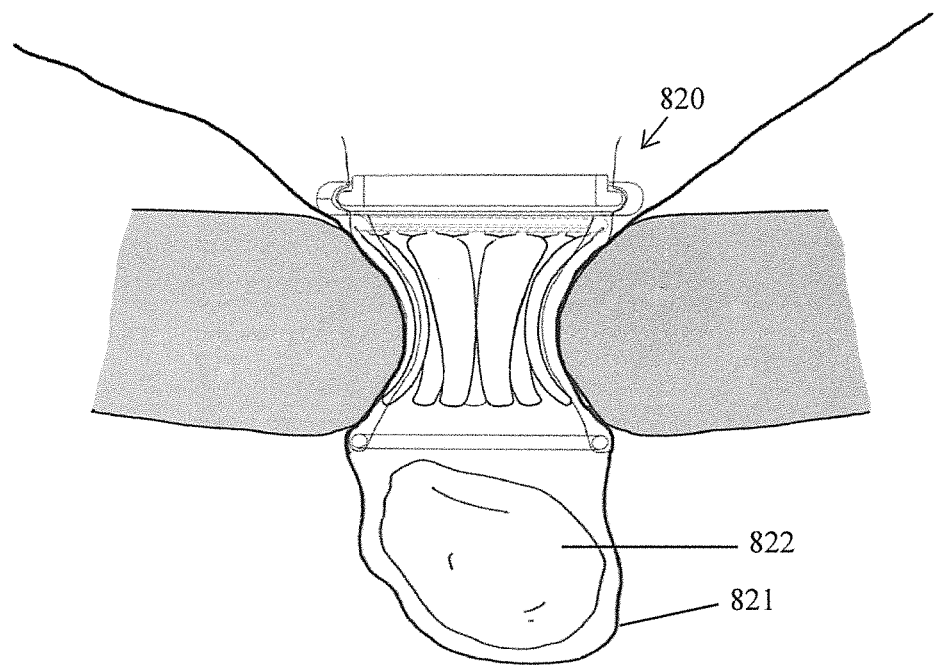

FIG. 218 shows the petals extending beyond 50% of incision depth, in place in a bag in an abdomen.

FIG. 220 illustrates that when tissue 222 is pulled up against the underside of a deployed and retracted guard, the upward force on the lower portion of the petals in the guard creates a 'shoe-horn' effect to aid in the retraction of the incision and removal of the tissue.

The arrows indicate that the upward force pushes the end of the petals laterally, and this dissipates the lateral force up the petal and encourages the incision to maximum retraction for optimal tissue removal.

FIGS. 221 to 224 are views from within a bag looking up at the distal ring positioned on the underside of the incision. FIG. 221 shows a typical view for a slightly thicker abdomen where petals 825 come just around the narrowest part of the incision. FIG. 223 is in a typical view for a thinner abdomen, the petals 825 reach as far as the distal ring and partially wrap around it, where required.

Figure 224:
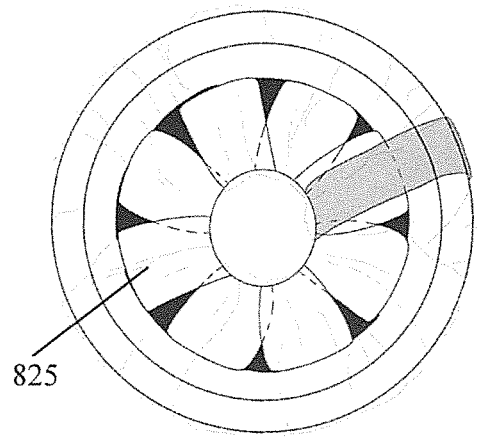

FIG. 224 illustrates colour being used to differentiate the two layers of petals to create a visible contrast in order to see the petals 825 more clearly.

Figure 225:
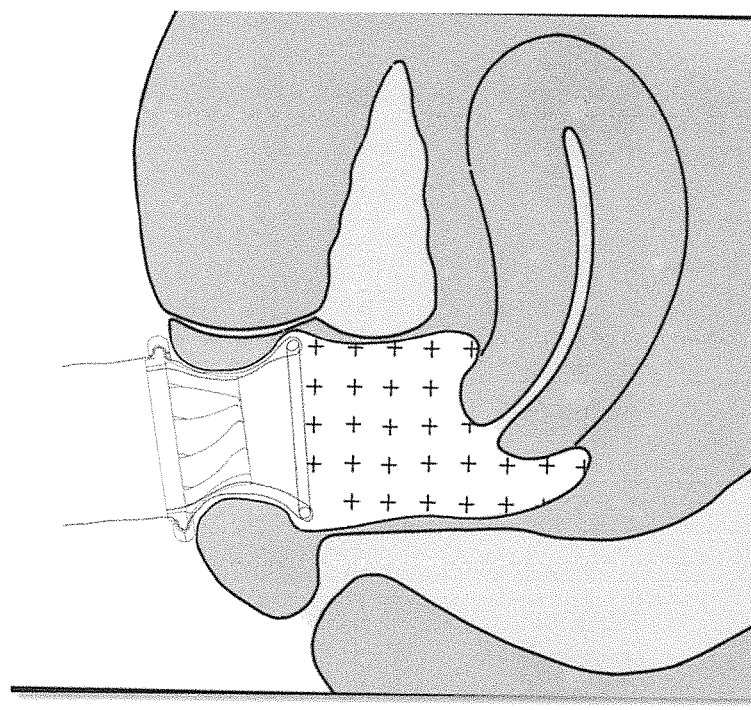
Figure 226:
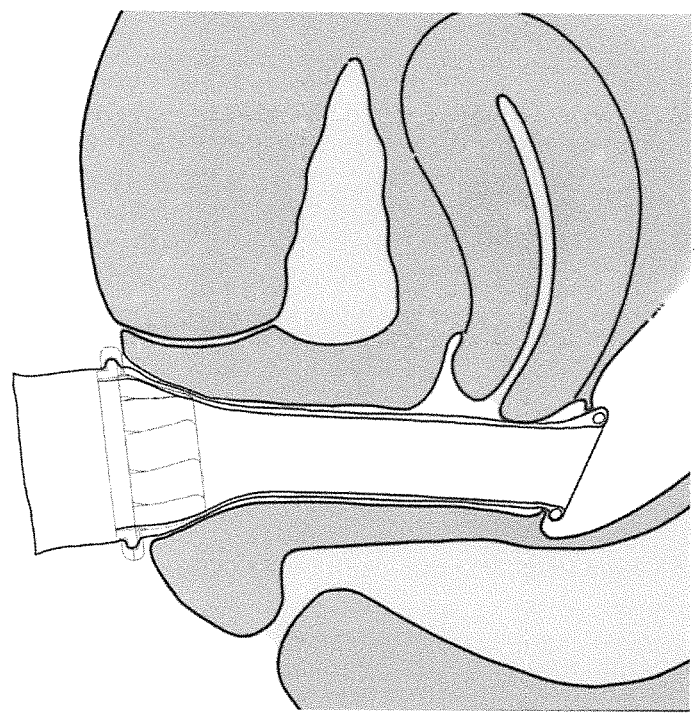

FIGS. 225 and 226 show an example of the device used through natural orifice, in this case a vagina. The base retractor guard can be used in the vaginal opening as shown in FIG. 225 or a distal ring inserted through a colpotomy at the back of the vaginal cavity as shown FIG. 226.

Figure 227:
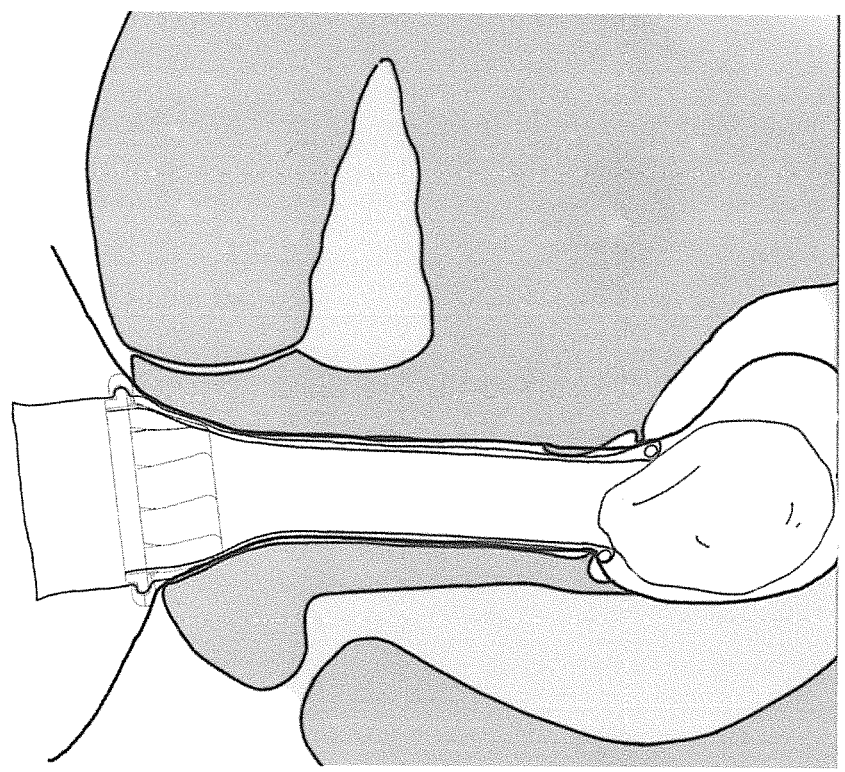
Figure 228:
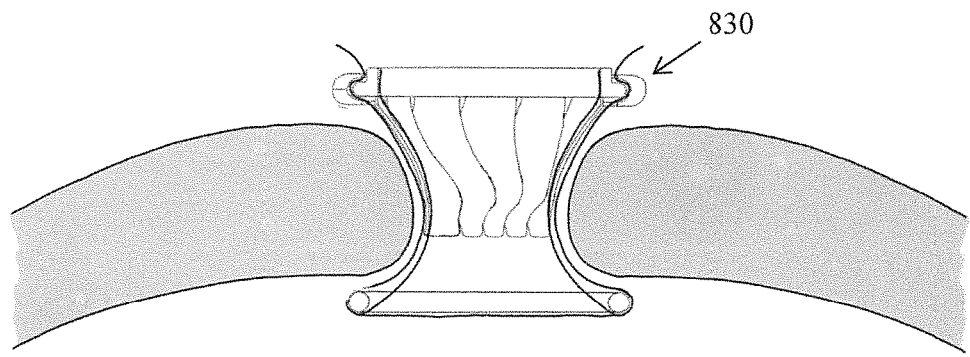
Figures 229, 230:
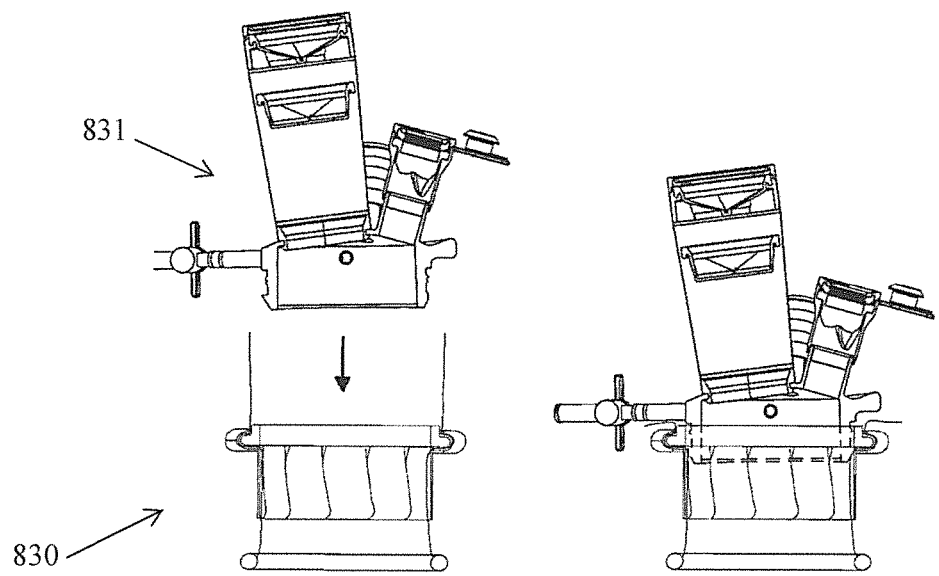
Figure 231:
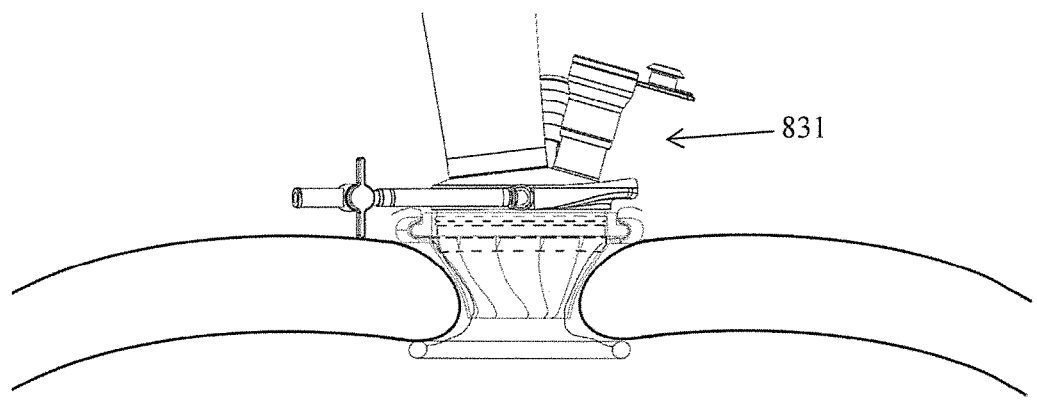

FIG. 227 illustrates a containment bag in situ during a transvaginal procedure.

It will be appreciated that the guard can be used with a bag in situ or as a means to protect the natural orifice itself during extraction/morcellation.

FIGS. 228 to 231 show the use of a guard retractor 830 as a stand-alone incision protector without a bag component.

The guard retractor may be used in conjunction with a single port boot device 831 for single port procedures with an extra level of protection for the incision from instruments.

FIGS. 232 and 233 further illustrate the guard of FIGS. 114 and 115 showing the guard, in use.

FIGS. 234 and 235 show a bag element 840 with distal tab loop 841 configuration whereby the loop is used to pull the bag element out of its introducer tube laparoscopically using a grasper 842 or similar.

Figure 236:
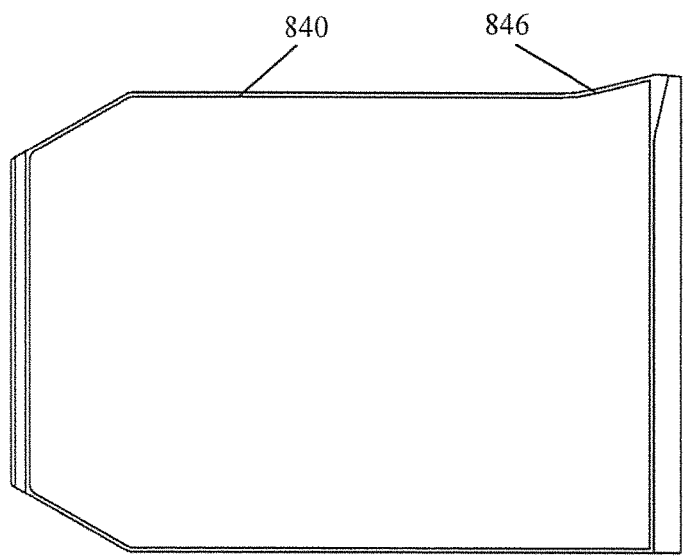
Figure 237:
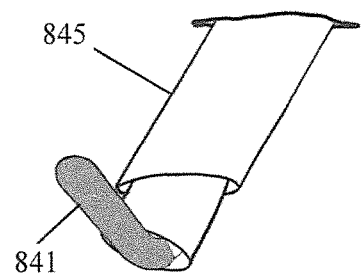
Figure 238:
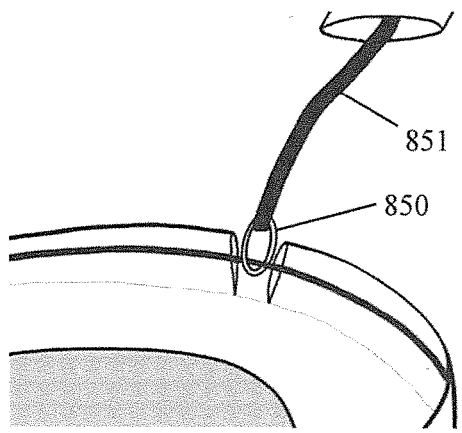
Figure 239:
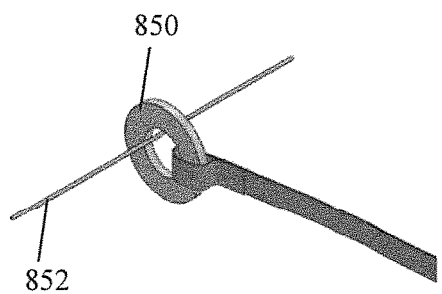
Figure 240:
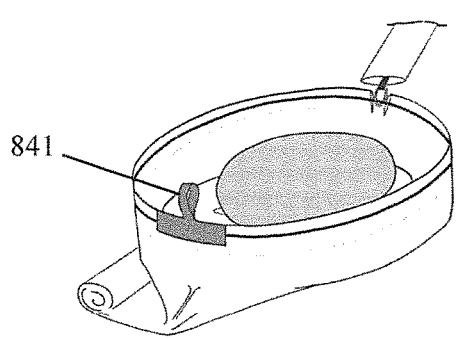
Figure 241:
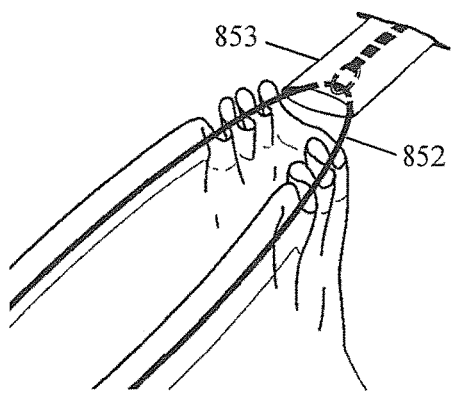
Figure 242:
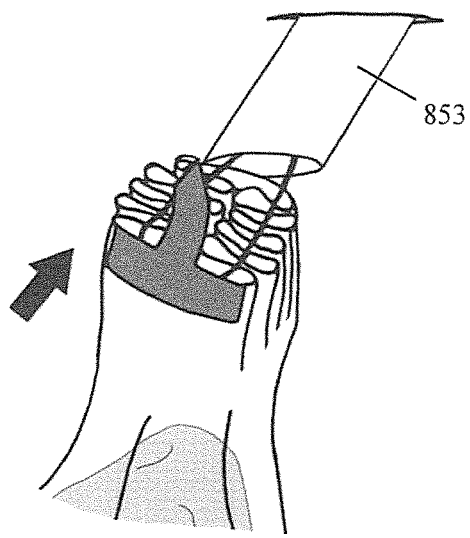
Figure 243:
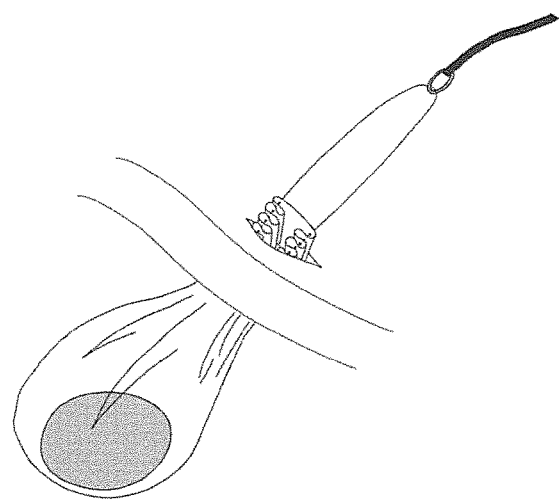

FIGS. 236 and 237 show a flat bag view of a bag in which there is a taper 846 near the top opening at one end. This taper facilitates an offset to the rolled body of bag when loaded into the introducer tube 845. The tab 841 can be seen in FIG. 237 exiting the tube 845 to indicate orientation without being obstructed by a rolled up bag.

Referring to FIGS. 238 to 243 there is illustrated a pull ring feature 850 of the bag, which is to be closed laparoscopically by pulling the ring 850 out through a trocar 851. The ring feature 850 is in this case a washer-like component between a bag tether 851 and a bag opening ring 852.

The ring 850 acts a buffer component to prevent the nitinol bay opening ring 852 becoming caught on the end of a trocar 853 when attempting to close the bag by pulling on the tether 851.

The washer component 850 centres the nitinol ring 852 within the trocar end orifice and therefore maximise the bend radius of the nitinol ring 852, thus reducing the force to close bag and also to reduce incidences of getting caught.

The washer-like component 850 can be round or lozenge shape or and shape with curved edges to sufficiently offset the wire during closure.

Figure 244:
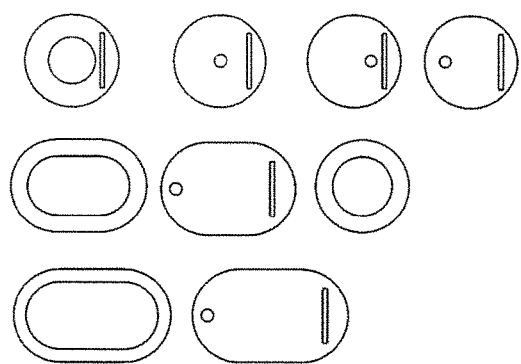

Referring to FIG. 244 there is illustrated an array of possible components in which the length, inner diameter size, location of wire and tether holes are varied.

The invention is not limited to the embodiments hereinbefore described, which may be varied in construction and detail.

The invention claimed is:

1. An apparatus for placement in a body opening including an incision or a natural body opening comprising:
   a retractor including a sleeve having an insertion configuration and a retracting configuration; and
   a guard device having an insertion configuration and a deployed configuration, the guard device being movable by the retractor from the insertion configuration to the deployed configuration as the retractor is moved to the retracting configuration, wherein at least a portion of the guard device is disposed between an outer surface and an inner surface of the sleeve, and wherein the guard device comprises a plurality of petals, wherein adjacent petals from the plurality of petals are overlapped in the insertion configuration, and wherein an amount of overlap of adjacent petals decreases as the retractor is moved from the insertion configuration to the retracting configuration.

2. The apparatus as claimed in claim 1, wherein the retractor comprises a distal retractor member and a proximal retractor member and wherein the guard device in the deployed configuration is located between the distal retractor member and the proximal retractor member.

3. The apparatus as claimed in claim 2, wherein the guard device is axially movable relative to the distal retractor member and/or the proximal retractor member on movement towards the deployed configuration.

4. The apparatus as claimed in claim 1, wherein the sleeve extends in two layers between the distal retractor member and the proximal retractor member to form a pocket between the two layers of the sleeve, and wherein the guard is located between the two layers of the sleeve.

5. The apparatus as claimed in claim 4, wherein the sleeve is wrapped around the distal retractor member.

6. The apparatus as claimed in claim 1, wherein the retractor further comprises:
   a distal member;
   a proximal member, wherein the sleeve extends at least between the distal member and the proximal member;
   a guide member for a proximal portion of the sleeve;
   a first sleeve portion extending distally from the proximal member to the distal member; and
   a second sleeve portion extending proximally from the distal member to the guide member.

7. The apparatus as claimed in claim, 6 wherein the guard device comprises a mounting ring which is located between the first and second sleeve portions.

8. The apparatus as claimed in claim 7, wherein the sleeve comprises a proximal portion for pulling the sleeve upwardly to shorten an axial extent between the distal member and the proximal member.

9. The apparatus as claimed in claim 8, wherein the mounting ring is movable upwardly as the sleeve is pulled upwardly.

10. The apparatus as claimed in claim 1, wherein each petal of the plurality of petals includes a proximal end and a distal end, wherein the distal end of each of the plurality of petals is configured to move radially outward from a longitudinal axis of the retractor as the retractor is moved from the insertion configuration to the retracting configuration.

11. The apparatus as claimed in claim 1, wherein each petal of the plurality of petals are arranged in a first layer of petals and at least one additional layer of petals, wherein the petals of the first layer are overlapped with the petals of the at least one additional layer of petals.

12. The apparatus as claimed in claim 11, wherein each of the petals of the plurality of petals includes a proximal neck, and wherein the proximal neck is configured to provide an inflection region to facilitate radial movement of the petal.

13. The apparatus as claimed in claim 11, wherein the guard device further includes a guard ring, and a proximal portion of the plurality of petals are connected to the guard ring.

14. The apparatus as claimed in claim 13, wherein the guard ring is moveable relative to the sleeve.

15. An apparatus for placement in a body opening comprising:
   a retractor including a retractor sleeve; and
   a guard device having an insertion configuration and a retracting configuration, wherein the guard device includes a plurality of elongated members connected to a proximal ring, wherein an inner surface of distal ends of each of the plurality of elongated members contacts the retractor sleeve, and wherein the retractor sleeve is configured to move the guard device between the insertion configuration and the retracting configuration by shortening the length of the retractor sleeve until a proximal ring of the retractor is positioned adjacent an outer surface of the body and a distal ring of the retractor is positioned against an inner surface of the body.

16. The apparatus of claim 15, wherein the distal end of each of the plurality of petal members moves radially outward from a longitudinal axis of the retractor as the guard device transitions between the insertion configuration and the retracting configuration.

17. The method of claim 16, wherein the proximal ring is moveable relative to a portion of the retractor sleeve.

18. A method for placing an apparatus in a body opening, the method comprising:

inserting a retractor into the body opening, wherein the retractor includes a sleeve attached to a guard device having a plurality of elongated members; and shortening a length of the retractor sleeve to cause a distal end of each the plurality of petals to expand radially outward.

\* \* \* \* \*